US007038014B2

(12) United States Patent
Harris et al.

(10) Patent No.: US 7,038,014 B2
(45) Date of Patent: May 2, 2006

(54) POLYCATION-SENSING RECEPTOR IN AQUATIC SPECIES AND METHODS OF USE THEREOF

(75) Inventors: H. William Harris, Dover, MA (US); Edward M. Brown, Milton, MA (US); Steven C. Hebert, Wellesley, MA (US)

(73) Assignee: Brigham and Women's Hospital, Boston, MA (US)

( * ) Notice: Subject to any disclaimer, the term of this patent is extended or adjusted under 35 U.S.C. 154(b) by 576 days.

(21) Appl. No.: 10/016,496

(22) Filed: Dec. 10, 2001

(65) Prior Publication Data

US 2003/0166908 A1 Sep. 4, 2003

Related U.S. Application Data

(60) Division of application No. 09/715,538, filed on Nov. 17, 2000, now abandoned, which is a division of application No. 09/162,021, filed on Sep. 28, 1998, now Pat. No. 6,337,391, which is a continuation-in-part of application No. PCT/US97/05031, filed on Mar. 27, 1997, which is a continuation-in-part of application No. 08/622,738, filed on Mar. 27, 1996, now abandoned.

(51) Int. Cl.
*C07K 14/435* (2006.01)
*C07H 21/04* (2006.01)
*C12N 15/00* (2006.01)

(52) U.S. Cl. ............... 530/350; 530/300; 536/23.1; 435/7.1; 435/69.1; 435/235.1; 435/325; 435/375; 435/320.1

(58) Field of Classification Search .......... 530/300, 530/350; 536/23.5; 435/7.1, 69.1, 235.1, 435/325, 375, 320.1
See application file for complete search history.

(56) References Cited

U.S. PATENT DOCUMENTS

| | | | |
|---|---|---|---|
| 3,777,709 A | 12/1973 | Anderson et al. | |
| 4,703,008 A | 10/1987 | Lin | 435/240.2 |
| 5,688,938 A | 11/1997 | Brown et al. | |
| 6,463,882 B1 | 10/2002 | Harris et al. | |
| 6,564,747 B1 | 5/2003 | Harris et al. | |
| 2003/0051269 A1 | 3/2003 | Harris et al. | |
| 2003/0082574 A1 | 5/2003 | Harris et al. | |
| 2003/0124090 A1 | 7/2003 | Harris et al. | |
| 2003/0124657 A1 | 7/2003 | Harris et al. | |

FOREIGN PATENT DOCUMENTS

| | | |
|---|---|---|
| WO | WO 97/35977 | 10/1997 |
| WO | WO 98/15627 | 4/1998 |
| WO | WO 02/30215 A2 | 4/2002 |

OTHER PUBLICATIONS

Uniprot-03 database, Accession No. P41180, Feb. 1, 1995.*
Uniprot-03 database, Accession No. P35384, Jun. 1, 1994.*
Uniprot-03 database, Accession No. P48442, Feb. 1, 1996.*
Baum, M., et al., "Recent Insights Into the coordinate regulation of body water and divalent mineral ion metabolism," *Am. J. Medical Sciences*, 316(5): 321-328 (1998).
Baum, M.A. et al., "An apical extracellular calcium/polyvalent cation sensing receptor (CaR) present in the osmoregulatory organs of salt water (SW) and fresh water (FW) fish likely plays a role in salinity adaptation," *J. of the Am. Soc. of Neurology* 7(9):1276 (1996).
Elger, E. B. et al, "Effect of adrenergic blockage with Bretylium and Phentolamine on Glomerular Filtration Rate in the Rainbow Trout, *Salmo Gairdneri* rich, adapting to Saline Water," *Comparative Biochemistry and Physiology*, 75C: 253-258 (1983).
Folmar, Leroy, C. and Dickhoff, W. W., "The Parr—Smolt Transformation (Smoltification) and Seawater Adaption in Salmonids," *Aquaculture*, 21: 1-37 (1982).
Solanki, T. G. et al., "Changes in the Mucous Cells of the Gills Buccal Cavity and Epidermis of the Nine-Spined Stickleback Pungitius—Pungitius Induced by Transferring the Fish to Sea Water," *Journal of Fish Biology*, 21(5):563-576 (1982).
Clark, M.S., et al., "Sparus aurata mRNA for extracellular calcium sensing receptor precursor (casr gene)," *EMBL Database Accession No.: AJ289717* (Jun. 9, 2001).
Clark, M.S., et al., "Calcitonin: Characterisation and Expression in a Telecost Fish, *Fugu rubripes*," *Journal of Molecular Endorocrinology*, 28: 111-123 (2002).

(Continued)

*Primary Examiner*—Joseph Murphy
*Assistant Examiner*—Nirmal S. Basi
(74) *Attorney, Agent, or Firm*—Hamilton, Brook, Smith & Reynolds, P.C.

(57) ABSTRACT

Polycation-sensing receptors present in aquatic species and methods of regulating polycation-sensing receptor-mediated functions in aquatic species are described.

8 Claims, 42 Drawing Sheets

OTHER PUBLICATIONS

Aida, K., et al., "Molecular Cloning of a Putative $Ca^{2+}$ Sensing Receptor cDNA from Human Kidney," *Biochemical and Biophysical Research Communications*, 214(2) :524-529 (1995).

Brown, E.M., et al., "Cloning and Characterization of an Extracellular $Ca^{2+}$-Sensing Receptor from Bovine Parathyroid," *Nature*, 366:757-580 (1993).

Brown, E.M., et al., "Calcium-Ion-Sensing Cell-Surface Receptors," *The New England Journal of Medicine*, 333(4) :234-240 (1995).

Darnell, J., et al., "The Plasma Membrane," Chapter 13 in *Molecular Cell Biology*, 516-520 (1990).

Davenport, J., "Synopsis of Biological Data on the Lumpsucker," *Food and Agriculture Organization of the United Nations*, Synopsis No. 147 pp. 1-19 (1985).

Du, S.J., et al., "Growth Enhancement in Transgenic Atlantic Salmon by the Use of an "All Fish " Chimeric Growth Hormone Gene Construct," *Bio/Technology* 10:176-181 (1992).

Evans, D.H., "Osmotic and Ionic Regulation," Chapter 11 in *The Physiology of Fishes*, (CRC Press, Boca Raton, FL) pp. 315-341 (1993).

Evans, G.H., et al., "Association of Magnesium Deficiency with the Blood Pressure-Lowering Effects of Calcium," *Journal of Hypertension*, 8(4) :327-337 (1990).

Prenkel, Y., et al., "Hypocalciuria of Preeclampsia Is Independent of Parathyroid Hormone Level," *Obstetrics & Gynecology*, 77(5) :689-691.

Gamba, G., et al., Primary Structure and Functional Expression of a cDNA Encoding the Thiazide-Sensitive, Electroneutral Sodium-Chloride Cotransporter, *Proc. Natl. Acad. Sci.* 90:2749-2753 (1993).

Gardner, W.D. and Osburn, W.A., "Structure of the Human Body," *Genitourinary System* pp. 365-366 (1967).

Garrett, J.E., et al., "Molecular Cloning and Functional Expression of Human Parathyroid Calcium Receptor cDNAs," *The Journal of Biological Chemistry*, 270(21) :12919-12925 (1995).

Hedemann, L., et al., "The Familial Magnesium-losing Kidney," *Acta Med Scand* 219(1) :133-6 (1986).

Hew, D.L., et al., "Antifreeze Protein Gene Transfer in Atlantic Salmon," *Molecular Marine Biology and Biotechnology* 1(4/5) :309-317 (1992).

Lonning, S., et al., "A Comparative Study of Pelagic and Demersal Eggs from Common Marine Fishes in Northern Norway," *Sarsia*, 73:49-60 (1988).

Norris, D.O., "Endocrine Regulation of Iono-Osmotic Balance in Teleosts," Chpater 16 in *Vertebrate Endocrinology*, Lea and Fabiger, eds. (Philadelphia, PA) pp. 425-443 (1985).

Plotkin, M.D., et al., "Localization of the Thiazide Sensitive NA-CL Cotransporter (TSC) in the Mammalian Kidney," *J. Am. Soc. Nephrol.*, 6:349A (1995).

Ramos, L.S., et al., "Urinary Calcium As an Early Marker for Preeclampsia," *Obstetrics & Gynecology*, 77(5) :685-688 (1991).

Riccardi, D., et al., "Cloning and Functional Expression of a Rat Kidney Extracellular Calcium/Polyvalent Cation-Sensing Receptor," *Proc. Natl. Acad. Sci. USA* 92:131-135 (1995).

Roberts, J.M., "Prevention or Early Treatment of Preeclampsia," *The New England Journal of Medicine* 337: 124-125 (1997).

Rokaw, M., et al., "Rapamycin (RAP) Stimulates Sodium Transport in A6 Cells Through Inhibition of Protein Kinase C (PKC), "*J. Am. Soc. Nephrol* 6:349A (1995).

Renfro, J.L., "Water and Ion Transport by the Urinary Bladder of the Teleost *Pseudopleuronectes Americanus*," *American Journal of Physiology* 228(1):52-61 (1975).

Sands, A.T., et al., "High Susceptibility to Ultraviolet-Induced arcinogenesis in Mice Lacking XPC," *Nature* 377: 162-165 (1995).

Sands, J.M., et al., "Apical Extracellular Calcium/jPolyvalent Cation-sensing Receptor Regulates Vasopressin-elicited Water Permeability in Rat Kidney Inner Medullary Collecting Duct," *J. Clin. Invest*. 99(6):1399-1405 (1997).

Siner, J., "Cloning of an Aquaporin Homologue Present in Water Channel Containing Endosomes of Toad Urinary Bladder," *Am. J. Physiol*. 270:C372-C381 (1996).

Targovnik, J.H., et al., "Regulation of Parathyroid Hormone Secretion in Vitro: Quantitative Aspects of Calcium and Magnesium Ion Control," *Endocrinology* 88:1477-1482 (1971).

Taufield, P.A., et al., "Hypocalciuria in Preeclampsia," *N Engl J Med* 316(12) :715-718 (1987).

Yamagami, K., et al., "Molecular and Cellular Basis of Formation, Hardening, and Breakdown of the Egg Envelope in Fish," *International Review of Cytology*, 136:51-92 (1992).

Veillette, P.A., et al., "Cortisol Mediates the Increase in Intestinal Fluid Absorption in Atlantic Salmon during Parr-Smolt Transformation," *General and Comparative Endocrinology* 97:250-258 (1995).

Zadunaisky, J.A., et al., "Osmolarity and Cell Volume Changes of Chloride Cells: The Nature of the Rapid Signal for Adaption to Salinities of *Fundulus heteroclitus*," *Bull. MDI Biol. Lab.*, 32:152-156 (1992).

Cole, et al., "Isolation and Characterization of Pleurociden, an Antimicrobial Peptide in the Skin Secretions of Winter Flounder," *J. Biol. Chem*. 272:12008-12013 (1997).

Forster, R. P., et al., "Formation of excretory products," Chapter 5 of Fish Physiology, Academic Press, New York, NY, pp. 313-345 (1969).

Elger, E.B. et al., "Adaption of renal function to hypotonic medium in winter flounder," *J. Comp. Physio*. B157:21-30 (1987).

Bai, M., et al., "Expression and characterization of inactivating and activating mutations in human $Ca^{2+}$ Sensing Receptor," *J. Biol. Chem*., 32:19537-19545 (1996).

Brown, E.M., et al., "A Comparison of the effects of divalent and trivalent cations on parathyroid hormones release," *Endocrinol*., 127:1064-1071 (1990).

Ward, P.T. et al., "Disulfide Bonds in the Extracellular Caldium-Polyvalent Cation-Sensing Receptor Correlate with Dimer Formation and its Response to divalent cations in Vitro," *Am Soc. Biochem. Mol. Bio*., 272:23; 14478-14483 (1998).

Naito, T. et al., "Putative pheromone receptors related to the $Ca^{2+}$-sensing receptor in *Fugu*," *Proc. Natl. Acad. Sci.*, 95:5178-5181 (Apr. 1998).

J. Nearing, et al., "Cloning and Expression of a Homologue of the Calcium (Ca2+) /Polyvalent Cation Receptor (CaR) Protein That Acts as a Magnesium (Mg2+) Sensor in Dogfish Shark (*Aqualus acanthias* ) Kidney," ASN 30th Annual Meeting, Nov. 2-5, 1997.

Ryba, N.J., et al., "A New *Multigene* Family of Putative Pheromone Receptors," *Neuron*, 19(2) :371-379 (1997).

* cited by examiner

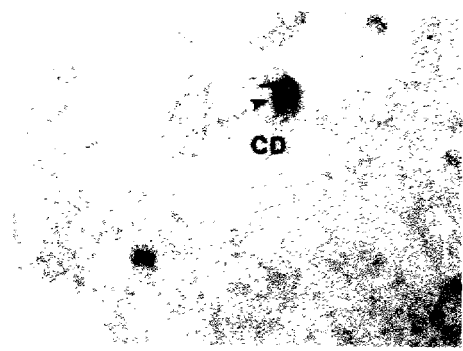
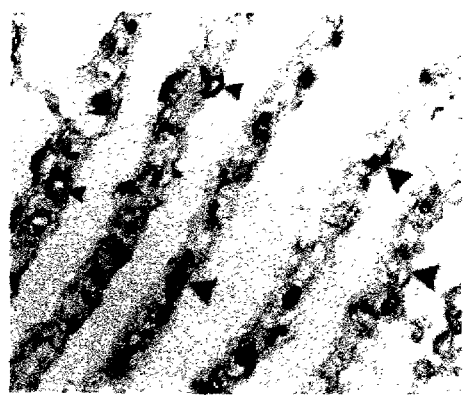
FIG.2A　　　　　　　FIG.2B
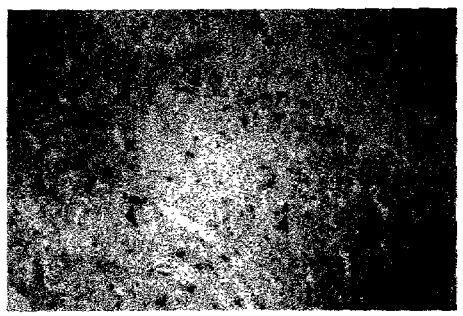
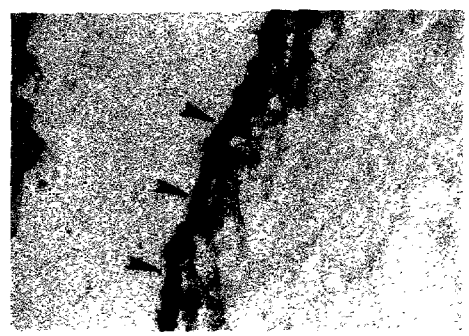
FIG.2C　　　　　　　FIG.2D
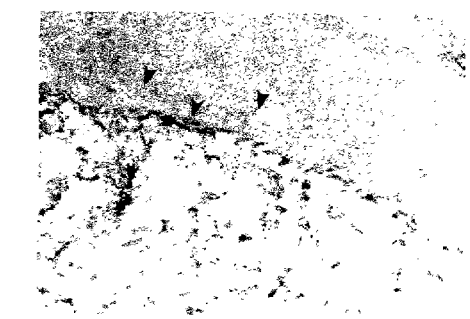
FIG.2E　　　　　　　FIG.2F

Polynucleotide SEQ ID NO: 1;  Polypeptide SEQ ID NO: 2

```
aattccgttg ctgtcggttc agtccaagtc tcctccagtg caaaatgaga aatggtggtc  60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcacccct tcttggagca tacgatcaac cctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcaca atg gct cag ctt cac tgc caa ctc tta ttc ttg   471
                    Met Ala Gln Leu His Cys Gln Leu Leu Phe Leu
                     1               5                       10 gga ttt aca ctc cta cag tcg tac aat gtc tca ggg tat ggt cca aac   519
Gly Phe Thr Leu Leu Gln Ser Tyr Asn Val Ser Gly Tyr Gly Pro Asn
            15                  20                  25 caa agg gcc cag aag aaa gga gac atc ata ctg gga ggt ctc ttc cca   567
Gln Arg Ala Gln Lys Lys Gly Asp Ile Ile Leu Gly Gly Leu Phe Pro
        30                  35                  40 ata cac ttt gga gta gcc gcc aag gat cag gac tta aaa tcg aga ccg   615
Ile His Phe Gly Val Ala Ala Lys Asp Gln Asp Leu Lys Ser Arg Pro
    45                  50                  55 gag gcg aca aaa tgt att cgg tac aat ttt cga ggc ttc cga tgg ctc   663
Glu Ala Thr Lys Cys Ile Arg Tyr Asn Phe Arg Gly Phe Arg Trp Leu
60                  65                  70                  75 cag gcg atg ata ttc gca att gaa gag att aac aac agt atg act ttc   711
Gln Ala Met Ile Phe Ala Ile Glu Glu Ile Asn Asn Ser Met Thr Phe
                80                  85                  90 ctg ccc aat atc acc ctg gga tat cgc ata ttt gac acg tgt aac acc   759
Leu Pro Asn Ile Thr Leu Gly Tyr Arg Ile Phe Asp Thr Cys Asn Thr
            95                  100                 105 gtg tcc aag gcg cta gag gca aca ctc agc ttt gtg gcc cag aac aaa   807
Val Ser Lys Ala Leu Glu Ala Thr Leu Ser Phe Val Ala Gln Asn Lys
        110                 115                 120 atc gac tcg ctg aac tta gat gag ttc tgt aac tgc tct gac cat atc   855
Ile Asp Ser Leu Asn Leu Asp Glu Phe Cys Asn Cys Ser Asp His Ile
    125                 130                 135 cca tcc aca ata gca gtg gtc ggg gca acc ggg tca gga atc tcc acg   903
Pro Ser Thr Ile Ala Val Val Gly Ala Thr Gly Ser Gly Ile Ser Thr
140                 145                 150                 155 gct gtg gcc aat cta ttg gga tta ttt tac att cca cag gtc agc tat   951
Ala Val Ala Asn Leu Leu Gly Leu Phe Tyr Ile Pro Gln Val Ser Tyr
                160                 165                 170 gcc tcc tcg agc agg ctg ctc agc aac aag aat gag tac aag gcc ttc   999
Ala Ser Ser Ser Arg Leu Leu Ser Asn Lys Asn Glu Tyr Lys Ala Phe
            175                 180                 185 ctg agg acc atc ccc aat gat gag caa cag gcc acg gcc atg gcc gag  1047
Leu Arg Thr Ile Pro Asn Asp Glu Gln Gln Ala Thr Ala Met Ala Glu
        190                 195                 200
```

FIG. 4A

Polynucleotide SEQ ID NO: 1; Polypeptide SEQ ID NO: 2 (CONTINUED)

```
atc atc gag cac ttc cag tgg aac tgg gtg gga acc ctg gca gcc gac    1095
Ile Ile Glu His Phe Gln Trp Asn Trp Val Gly Thr Leu Ala Ala Asp
    205             210                 215 gat gac tat ggc cgc cca ggc att gac aag ttc cgg gag gag gcc gtt    1143
Asp Asp Tyr Gly Arg Pro Gly Ile Asp Lys Phe Arg Glu Glu Ala Val
220             225                 230                 235 aag agg gac atc tgt att gac ttc agt gag atg atc tct cag tac tac    1191
Lys Arg Asp Ile Cys Ile Asp Phe Ser Glu Met Ile Ser Gln Tyr Tyr
                240                 245                 250 acc cag aag cag ttg gag ttc atc gcc gac gtc atc cag aac tcc tcg    1239
Thr Gln Lys Gln Leu Glu Phe Ile Ala Asp Val Ile Gln Asn Ser Ser
            255                 260                 265 gcc aag gtc atc gtg gtc ttc tcc aat ggc ccc gac ctg gag ccg ctc    1287
Ala Lys Val Ile Val Val Phe Ser Asn Gly Pro Asp Leu Glu Pro Leu
        270                 275                 280 atc cag gag ata gtt cgg aga aac atc acc gat cgg atc tgg ctg gcc    1335
Ile Gln Glu Ile Val Arg Arg Asn Ile Thr Asp Arg Ile Trp Leu Ala
    285                 290                 295 agc gag gct tgg gcc agc tct tcg ctc att gcc aag cca gag tac ttc    1383
Ser Glu Ala Trp Ala Ser Ser Ser Leu Ile Ala Lys Pro Glu Tyr Phe
300                 305                 310                 315 cac gtg gtc ggc ggc acc atc ggc ttc gct ctc agg gcg ggg cgt atc    1431
His Val Val Gly Gly Thr Ile Gly Phe Ala Leu Arg Ala Gly Arg Ile
                320                 325                 330 cca ggg ttc aac aag ttc ctg aag gag gtc cac ccc agc agg tcc tcg    1479
Pro Gly Phe Asn Lys Phe Leu Lys Glu Val His Pro Ser Arg Ser Ser
            335                 340                 345 gac aat ggg ttt gtc aag gag ttc tgg gag gag acc ttc aac tgc tac    1527
Asp Asn Gly Phe Val Lys Glu Phe Trp Glu Glu Thr Phe Asn Cys Tyr
        350                 355                 360 ttc acc gag aag acc ctg acg cag ctg aag aat tcc aag gtg ccc tcg    1575
Phe Thr Glu Lys Thr Leu Thr Gln Leu Lys Asn Ser Lys Val Pro Ser
    365                 370                 375 cac gga ccg gcg gct caa ggg gac ggc tcc aag gcg ggg aac tcc aga    1623
His Gly Pro Ala Ala Gln Gly Asp Gly Ser Lys Ala Gly Asn Ser Arg
380                 385                 390                 395 cgg aca gcc cta cgc cac ccc tgc act ggg gag gag aac atc acc agc    1671
Arg Thr Ala Leu Arg His Pro Cys Thr Gly Glu Glu Asn Ile Thr Ser
                400                 405                 410 gtg gag acc ccc tac ctg gat tat aca cac ctg agg atc tcc tac aat    1719
Val Glu Thr Pro Tyr Leu Asp Tyr Thr His Leu Arg Ile Ser Tyr Asn
            415                 420                 425 gta tac gtg gcc gtc tac tcc att gct cac gcc ctg caa gac atc cac    1767
Val Tyr Val Ala Val Tyr Ser Ile Ala His Ala Leu Gln Asp Ile His
        430                 435                 440
```

FIG. 4B

Polynucleotide SEQ ID NO: 1;  Polypeptide SEQ ID NO: 2 (CONTINUED)

```
tct tgc aaa ccc ggc acg ggc atc ttt gca aac gga tct tgt gca gat    1815
Ser Cys Lys Pro Gly Thr Gly Ile Phe Ala Asn Gly Ser Cys Ala Asp
    445             450                 455 att aaa aaa gtt gag gcc tgg cag gtc ctc aac cat ctg ctg cat ctg    1863
Ile Lys Lys Val Glu Ala Trp Gln Val Leu Asn His Leu Leu His Leu
460             465                 470                 475 aag ttt acc aac agc atg ggt gag cag gtt gac ttt gac gat caa ggt    1911
Lys Phe Thr Asn Ser Met Gly Glu Gln Val Asp Phe Asp Asp Gln Gly
                480                 485                 490 gac ctc aag ggg aac tac acc att atc aac tgg cag ctc tcc gca gag    1959
Asp Leu Lys Gly Asn Tyr Thr Ile Ile Asn Trp Gln Leu Ser Ala Glu
            495                 500                 505 gat gaa tcg gtg ttg ttc cat gag gtg ggc aac tac aac gcc tac gct    2007
Asp Glu Ser Val Leu Phe His Glu Val Gly Asn Tyr Asn Ala Tyr Ala
        510                 515                 520 aag ccc agt gac cga ctc aac atc aac gaa aag aaa atc ctc tgg agt    2055
Lys Pro Ser Asp Arg Leu Asn Ile Asn Glu Lys Lys Ile Leu Trp Ser
    525                 530                 535 ggc ttc tcc aaa gtg gtt cct ttc tcc aac tgc agt cga gac tgt gtg    2103
Gly Phe Ser Lys Val Val Pro Phe Ser Asn Cys Ser Arg Asp Cys Val
540                 545                 550                 555 ccg ggc acc agg aag ggg atc atc gag ggg gag ccc acc tgc tgc ttt    2151
Pro Gly Thr Arg Lys Gly Ile Ile Glu Gly Glu Pro Thr Cys Cys Phe
                560                 565                 570 gaa tgc atg gca tgt gca gag gga gag ttc agt gat gaa aac gat gca    2199
Glu Cys Met Ala Cys Ala Glu Gly Glu Phe Ser Asp Glu Asn Asp Ala
            575                 580                 585 agt gcg tgt aca aag tgc ccg aat gat ttc tgg tcg aat gag aac cac    2247
Ser Ala Cys Thr Lys Cys Pro Asn Asp Phe Trp Ser Asn Glu Asn His
        590                 595                 600 acg tcg tgc atc gcc aag gag atc gag tac ctg tcg tgg acg gag ccc    2295
Thr Ser Cys Ile Ala Lys Glu Ile Glu Tyr Leu Ser Trp Thr Glu Pro
    605                 610                 615 ttc ggg atc gct ctg acc atc ttc gcc gta ctg ggc atc ctg atc acc    2343
Phe Gly Ile Ala Leu Thr Ile Phe Ala Val Leu Gly Ile Leu Ile Thr
620                 625                 630                 635 tcc ttc gtg ctg ggg gtc ttc atc aag ttc agg aac act ccc atc gtg    2391
Ser Phe Val Leu Gly Val Phe Ile Lys Phe Arg Asn Thr Pro Ile Val
                640                 645                 650 aag gcc acc aac cgg gag ttg tcc tac ctg ctg ctc ttc tcc ctc atc    2439
Lys Ala Thr Asn Arg Glu Leu Ser Tyr Leu Leu Leu Phe Ser Leu Ile
            655                 660                 665 tgc tgc ttc tcc agc tcg ctc atc ttc atc ggc gag ccc agg gac tgg    2487
Cys Cys Phe Ser Ser Ser Leu Ile Phe Ile Gly Glu Pro Arg Asp Trp
        670                 675                 680
```

FIG. 4C

Polynucleotide SEQ ID NO: 1; Polypeptide SEQ ID NO: 2 (CONTINUED)

```
acc tgt cgg ctc cgc caa ccg gcc ttt ggc atc agc ttc gtc ctg tgc    2535
Thr Cys Arg Leu Arg Gln Pro Ala Phe Gly Ile Ser Phe Val Leu Cys
685                 690                 695 atc tcc tgc atc ctg gtg aag acc aac cgg gtg ctg ctg gtc ttc gag    2583
Ile Ser Cys Ile Leu Val Lys Thr Asn Arg Val Leu Leu Val Phe Glu
700                 705                 710                 715 gcc aag atc ccc acc agc ctc cac cgc aag tgg gtg ggc ctc aac ctg    2631
Ala Lys Ile Pro Thr Ser Leu His Arg Lys Trp Val Gly Leu Asn Leu
            720                 725                 730 cag ttc ctc ctg gtc ttc ctc tgc atc ctg gtg caa atc gtc acc tgc    2679
Gln Phe Leu Leu Val Phe Leu Cys Ile Leu Val Gln Ile Val Thr Cys
                735                 740                 745 atc atc tgg ctc tac acc gcg cct ccc tcc agc tac agg aac cat gag    2727
Ile Ile Trp Leu Tyr Thr Ala Pro Pro Ser Ser Tyr Arg Asn His Glu
            750                 755                 760 ctg gag gac gag gtc atc ttc atc acc tgc gac gag ggc tcg ctc atg    2775
Leu Glu Asp Glu Val Ile Phe Ile Thr Cys Asp Glu Gly Ser Leu Met
765                 770                 775 gcg ctg ggc ttc ctc atc ggc tac acc tgc ctc ctc gcc gcc atc tgc    2823
Ala Leu Gly Phe Leu Ile Gly Tyr Thr Cys Leu Leu Ala Ala Ile Cys
780                 785                 790                 795 ttc ttc ttc gcc ttc aag tcc cgt aag ctg ccg gag aac ttc aac gag    2871
Phe Phe Phe Ala Phe Lys Ser Arg Lys Leu Pro Glu Asn Phe Asn Glu
                800                 805                 810 gct aag ttc atc acc ttc agc atg ttg atc ttc ttc atc gtc tgg atc    2919
Ala Lys Phe Ile Thr Phe Ser Met Leu Ile Phe Phe Ile Val Trp Ile
            815                 820                 825 tcc ttc atc ccc gcc tat gtc agc acc tac ggc aag ttt gtg tcg gcc    2967
Ser Phe Ile Pro Ala Tyr Val Ser Thr Tyr Gly Lys Phe Val Ser Ala
            830                 835                 840 gtg gag gtg att gcc atc ctg gcc tcc agc ttc ggg ctg ctg ggc tgc    3015
Val Glu Val Ile Ala Ile Leu Ala Ser Ser Phe Gly Leu Leu Gly Cys
845                 850                 855 att tac ttc aac aag tgt tac atc atc ctg ttc aag ccg tgc cgt aac    3063
Ile Tyr Phe Asn Lys Cys Tyr Ile Ile Leu Phe Lys Pro Cys Arg Asn
860                 865                 870                 875 acc atc gag gag gtg cgc tgc agc acg gcg gcc cac gcc ttc aag gtg    3111
Thr Ile Glu Glu Val Arg Cys Ser Thr Ala Ala His Ala Phe Lys Val
            880                 885                 890 gcg gcc cgg gcc acc ctc cgg cgc agc gcc gcg tct cgc aag cgc tcc    3159
Ala Ala Arg Ala Thr Leu Arg Arg Ser Ala Ala Ser Arg Lys Arg Ser
            895                 900                 905 agc agc ctg tgc ggc tcc acc atc tcc tcg ccc gcc tcg tcc acc tgc    3207
Ser Ser Leu Cys Gly Ser Thr Ile Ser Ser Pro Ala Ser Ser Thr Cys
                910                 915                 920
```

FIG. 4D

Polynucleotide SEQ ID NO: 1;  Polypeptide SEQ ID NO: 2 (CONTINUED)

```
ggg ccg ggc ctc acc atg gag atg cag cgc tgc agc acg cag aag gtc   3255
Gly Pro Gly Leu Thr Met Glu Met Gln Arg Cys Ser Thr Gln Lys Val
925                 930                 935 agc ttc ggc agc ggc acc gtc acc ctg tcg ctc agc ttc gag gag aca   3303
Ser Phe Gly Ser Gly Thr Val Thr Leu Ser Leu Ser Phe Glu Glu Thr
940                 945                 950                 955 ggc cga tac gcc acc ctc agc cgc acg gcc cgc agc agg aac tcg gcg   3351
Gly Arg Tyr Ala Thr Leu Ser Arg Thr Ala Arg Ser Arg Asn Ser Ala
                960                 965                 970 gat ggc cgc agc ggc gac gac ctg cca tct aga cac cac gac cag ggc   3399
Asp Gly Arg Ser Gly Asp Asp Leu Pro Ser Arg His His Asp Gln Gly
                975                 980                 985 ccg cct cag aaa tgc gag ccc cag ccc gcc aac gat gcc cga tac aag   3447
Pro Pro Gln Lys Cys Glu Pro Gln Pro Ala Asn Asp Ala Arg Tyr Lys
            990                 995                 1000 gcg gcg ccg acc aag ggc acc cta gag tcg ccg ggc ggc agc aag gag   3495
Ala Ala Pro Thr Lys Gly Thr Leu Glu Ser Pro Gly Gly Ser Lys Glu
        1005                1010                1015 cgc ccc aca act atg gag gaa acc taa tccaactcct ccatcaaccc         3542
Arg Pro Thr Thr Met Glu Glu Thr
1020                1025 caagaacatc ctccacggca gcaccgtcga caactgacat caactcctaa ccggtggctg 3602
cccaacctct cccctctccg gcactttgcg ttttgctgaa gattgcagca tctgcagttc 3662
cttttatccc tgattttctg acttggatat ttactagtgt gcgatggaat atcacaacat 3722
aatgagttgc acaattaggt gagcagagtt gtgtcaaagt atctgaacta tctgaagtat 3782
ctgaactact ttattctctc gaattgtatt acaaacattt gaagtatttt tagtgacatt 3842
atgttctaac attgtcaaga taatttgtta caacatataa ggtaccacct gaagcagtga 3902
ctgagattgc cactgtgatg acagaactgt tttataacat ttatcattga aacctggatt 3962
gcaacaggaa tataatgact gtaacaaaaa aattgttgat tatcttaaaa atgcaaattg 4022
taatcagatg tgtaaaattg gtaattactt ctgtacatta aatgcatatt tcttgataaa 4082
aaaaaaaaaa aaaaaaaaaa aaaaaaaaaa aaaagcggcc cgacagcaac gg          4134
```

FIG. 4E

Polynucleotide SEQ ID NO: 1; Polypeptide SEQ ID NO: 2

```
aattccgttg ctgtcggttc agtccaagtc tcctccagtg caaaatgaga aatggtggtc  60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcaccctt tcttggagca tacgatcaac cctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcaca atg gct cag ctt cac tgc caa ctc tta ttc ttg  471
               Met Ala Gln Leu His Cys Gln Leu Leu Phe Leu
                 1               5                  10 gga ttt aca ctc cta cag tcg tac aat gtc tca ggg tat ggt cca aac  519
Gly Phe Thr Leu Leu Gln Ser Tyr Asn Val Ser Gly Tyr Gly Pro Asn
         15                  20                  25 caa agg gcc cag aag aaa gga gac atc ata ctg gga ggt ctc ttc cca  567
Gln Arg Ala Gln Lys Lys Gly Asp Ile Ile Leu Gly Gly Leu Phe Pro
     30                  35                  40 ata cac ttt gga gta gcc gcc aag gat cag gac tta aaa tcg aga ccg  615
Ile His Phe Gly Val Ala Ala Lys Asp Gln Asp Leu Lys Ser Arg Pro
         45                  50                  55 gag gcg aca aaa tgt att cgg tac aat ttt cga ggc ttc cga tgg ctc  663
Glu Ala Thr Lys Cys Ile Arg Tyr Asn Phe Arg Gly Phe Arg Trp Leu
 60                  65                  70                  75 cag gcg atg ata ttc gca att gaa gag att aac aac agt atg act ttc  711
Gln Ala Met Ile Phe Ala Ile Glu Glu Ile Asn Asn Ser Met Thr Phe
             80                  85                  90 ctg ccc aat atc acc ctg gga tat cgc ata ttt gac acg tgt aac acc  759
Leu Pro Asn Ile Thr Leu Gly Tyr Arg Ile Phe Asp Thr Cys Asn Thr
         95                  100                 105 gtg tcc aag gcg cta gag gca aca ctc agc ttt gtg gcc cag aac aaa  807
Val Ser Lys Ala Leu Glu Ala Thr Leu Ser Phe Val Ala Gln Asn Lys
     110                 115                 120 atc gac tcg ctg aac tta gat gag ttc tgt aac tgc tct gac cat atc  855
Ile Asp Ser Leu Asn Leu Asp Glu Phe Cys Asn Cys Ser Asp His Ile
 125                 130                 135 cca tcc aca ata gca gtg gtc ggg gca acc ggg tca gga atc tcc acg  903
Pro Ser Thr Ile Ala Val Val Gly Ala Thr Gly Ser Gly Ile Ser Thr
140                  145                 150                 155 gct gtg gcc aat cta ttg gga tta ttt tac att cca cag gtc agc tat  951
Ala Val Ala Asn Leu Leu Gly Leu Phe Tyr Ile Pro Gln Val Ser Tyr
             160                 165                 170 gcc tcc tcg agc agg ctg ctc agc aac aag aat gag tac aag gcc ttc  999
Ala Ser Ser Ser Arg Leu Leu Ser Asn Lys Asn Glu Tyr Lys Ala Phe
         175                 180                 185 ctg agg acc atc ccc aat gat gag caa cag gcc acg gcc atg gcc gag 1047
Leu Arg Thr Ile Pro Asn Asp Glu Gln Gln Ala Thr Ala Met Ala Glu
     190                 195                 200
```

FIG. 5A

Polynucleotide SEQ ID NO: 1;  Polypeptide SEQ ID NO: 2 (CONTINUED)

```
atc atc gag cac ttc cag tgg aac tgg gtg gga acc ctg gca gcc gac      1095
Ile Ile Glu His Phe Gln Trp Asn Trp Val Gly Thr Leu Ala Ala Asp
    205             210                 215 gat gac tat ggc cgc cca ggc att gac aag ttc cgg gag gag gcc gtt      1143
Asp Asp Tyr Gly Arg Pro Gly Ile Asp Lys Phe Arg Glu Glu Ala Val
220                 225                 230                 235 aag agg gac atc tgt att gac ttc agt gag atg atc tct cag tac tac      1191
Lys Arg Asp Ile Cys Ile Asp Phe Ser Glu Met Ile Ser Gln Tyr Tyr
                240                 245                 250 acc cag aag cag ttg gag ttc atc gcc gac gtc atc cag aac tcc tcg      1239
Thr Gln Lys Gln Leu Glu Phe Ile Ala Asp Val Ile Gln Asn Ser Ser
            255                 260                 265 gcc aag gtc atc gtg gtc ttc tcc aat ggc ccc gac ctg gag ccg ctc      1287
Ala Lys Val Ile Val Val Phe Ser Asn Gly Pro Asp Leu Glu Pro Leu
        270                 275                 280 atc cag gag ata gtt cgg aga aac atc acc gat cgg atc tgg ctg gcc      1335
Ile Gln Glu Ile Val Arg Arg Asn Ile Thr Asp Arg Ile Trp Leu Ala
    285                 290                 295 agc gag gct tgg gcc agc tct tcg ctc att gcc aag cca gag tac ttc      1383
Ser Glu Ala Trp Ala Ser Ser Ser Leu Ile Ala Lys Pro Glu Tyr Phe
300                 305                 310                 315 cac gtg gtc ggc ggc acc atc ggc ttc gct ctc agg gcg ggg cgt atc      1431
His Val Val Gly Gly Thr Ile Gly Phe Ala Leu Arg Ala Gly Arg Ile
                320                 325                 330 cca ggg ttc aac aag ttc ctg aag gag gtc cac ccc agc agg tcc tcg      1479
Pro Gly Phe Asn Lys Phe Leu Lys Glu Val His Pro Ser Arg Ser Ser
            335                 340                 345 gac aat ggg ttt gtc aag gag ttc tgg gag gag acc ttc aac tgc tac      1527
Asp Asn Gly Phe Val Lys Glu Phe Trp Glu Glu Thr Phe Asn Cys Tyr
        350                 355                 360 ttc acc gag aag acc ctg acg cag ctg aag aat tcc aag gtg ccc tcg      1575
Phe Thr Glu Lys Thr Leu Thr Gln Leu Lys Asn Ser Lys Val Pro Ser
    365                 370                 375 cac gga ccg gcg gct caa ggg gac ggc tcc aag gcg ggg aac tcc aga      1623
His Gly Pro Ala Ala Gln Gly Asp Gly Ser Lys Ala Gly Asn Ser Arg
380                 385                 390                 395 cgg aca gcc cta cgc cac ccc tgc act ggg gag gag aac atc acc agc      1671
Arg Thr Ala Leu Arg His Pro Cys Thr Gly Glu Glu Asn Ile Thr Ser
                400                 405                 410 gtg gag acc ccc tac ctg gat tat aca cac ctg agg atc tcc tac aat      1719
Val Glu Thr Pro Tyr Leu Asp Tyr Thr His Leu Arg Ile Ser Tyr Asn
            415                 420                 425 gta tac gtg gcc gtc tac tcc att gct cac gcc ctg caa gac atc cac      1767
Val Tyr Val Ala Val Tyr Ser Ile Ala His Ala Leu Gln Asp Ile His
        430                 435                 440
```

FIG. 5B

Polynucleotide SEQ ID NO: 1;  Polypeptide SEQ ID NO: 2 (CONTINUED)

```
tct tgc aaa ccc ggc acg ggc atc ttt gca aac gga tct tgt gca gat    1815
Ser Cys Lys Pro Gly Thr Gly Ile Phe Ala Asn Gly Ser Cys Ala Asp
    445             450                 455 att aaa aaa gtt gag gcc tgg cag gtc ctc aac cat ctg ctg cat ctg    1863
Ile Lys Lys Val Glu Ala Trp Gln Val Leu Asn His Leu Leu His Leu
460             465                 470                 475 aag ttt acc aac agc atg ggt gag cag gtt gac ttt gac gat caa ggt    1911
Lys Phe Thr Asn Ser Met Gly Glu Gln Val Asp Phe Asp Asp Gln Gly
                480                 485                 490 gac ctc aag ggg aac tac acc att atc aac tgg cag ctc tcc gca gag    1959
Asp Leu Lys Gly Asn Tyr Thr Ile Ile Asn Trp Gln Leu Ser Ala Glu
        495                 500                 505 gat gaa tcg gtg ttg ttc cat gag gtg ggc aac tac aac gcc tac gct    2007
Asp Glu Ser Val Leu Phe His Glu Val Gly Asn Tyr Asn Ala Tyr Ala
        510                 515                 520 aag ccc agt gac cga ctc aac atc aac gaa aag aaa atc ctc tgg agt    2055
Lys Pro Ser Asp Arg Leu Asn Ile Asn Glu Lys Lys Ile Leu Trp Ser
    525                 530                 535 ggc ttc tcc aaa gtg gtt cct ttc tcc aac tgc agt cga gac tgt gtg    2103
Gly Phe Ser Lys Val Val Pro Phe Ser Asn Cys Ser Arg Asp Cys Val
540             545                 550                 555 ccg ggc acc agg aag ggg atc atc gag ggg gag ccc acc tgc tgc ttt    2151
Pro Gly Thr Arg Lys Gly Ile Ile Glu Gly Glu Pro Thr Cys Cys Phe
                560                 565                 570 gaa tgc atg gca tgt gca gag gga gag ttc agt gat gaa aac gat gca    2199
Glu Cys Met Ala Cys Ala Glu Gly Glu Phe Ser Asp Glu Asn Asp Ala
        575                 580                 585 agt gcg tgt aca aag tgc ccg aat gat ttc tgg tcg aat gag aac cac    2247
Ser Ala Cys Thr Lys Cys Pro Asn Asp Phe Trp Ser Asn Glu Asn His
        590                 595                 600 acg tcg tgc atc gcc aag gag atc gag tac ctg tcg tgg acg gag ccc    2295
Thr Ser Cys Ile Ala Lys Glu Ile Glu Tyr Leu Ser Trp Thr Glu Pro
    605                 610                 615 ttc ggg atc gct ctg acc atc ttc gcc gta ctg ggc atc ctg atc acc    2343
Phe Gly Ile Ala Leu Thr Ile Phe Ala Val Leu Gly Ile Leu Ile Thr
620             625                 630                 635 tcc ttc gtg ctg ggg gtc ttc atc aag ttc agg aac act ccc atc gtg    2391
Ser Phe Val Leu Gly Val Phe Ile Lys Phe Arg Asn Thr Pro Ile Val
                640                 645                 650 aag gcc acc aac cgg gag ttg tcc tac ctg ctg ctc ttc tcc ctc atc    2439
Lys Ala Thr Asn Arg Glu Leu Ser Tyr Leu Leu Leu Phe Ser Leu Ile
        655                 660                 665 tgc tgc ttc tcc agc tcg ctc atc ttc atc ggc gag ccc agg gac tgg    2487
Cys Cys Phe Ser Ser Ser Leu Ile Phe Ile Gly Glu Pro Arg Asp Trp
        670                 675                 680
```

FIG. 5C

Polynucleotide SEQ ID NO: 1;   Polypeptide SEQ ID NO: 2 (CONTINUED)

```
acc tgt cgg ctc cgc caa ccg gcc ttt ggc atc agc ttc gtc ctg tgc    2535
Thr Cys Arg Leu Arg Gln Pro Ala Phe Gly Ile Ser Phe Val Leu Cys
685                 690                 695 atc tcc tgc atc ctg gtg aag acc aac cgg gtg ctg ctg gtc ttc gag    2583
Ile Ser Cys Ile Leu Val Lys Thr Asn Arg Val Leu Leu Val Phe Glu
700                 705                 710                 715 gcc aag atc ccc acc agc ctc cac cgc aag tgg gtg ggc ctc aac ctg    2631
Ala Lys Ile Pro Thr Ser Leu His Arg Lys Trp Val Gly Leu Asn Leu
            720                 725                 730 cag ttc ctc ctg gtc ttc ctc tgc atc ctg gtg caa atc gtc acc tgc    2679
Gln Phe Leu Leu Val Phe Leu Cys Ile Leu Val Gln Ile Val Thr Cys
                735                 740                 745 atc atc tgg ctc tac acc gcg cct ccc tcc agc tac agg aac cat gag    2727
Ile Ile Trp Leu Tyr Thr Ala Pro Pro Ser Ser Tyr Arg Asn His Glu
            750                 755                 760 ctg gag gac gag gtc atc ttc atc acc tgc gac gag ggc tcg ctc atg    2775
Leu Glu Asp Glu Val Ile Phe Ile Thr Cys Asp Glu Gly Ser Leu Met
765                 770                 775 gcg ctg ggc ttc ctc atc ggc tac acc tgc ctc ctc gcc gcc atc tgc    2823
Ala Leu Gly Phe Leu Ile Gly Tyr Thr Cys Leu Leu Ala Ala Ile Cys
780                 785                 790                 795 ttc ttc ttc gcc ttc aag tcc cgt aag ctg ccg gag aac ttc aac gag    2871
Phe Phe Phe Ala Phe Lys Ser Arg Lys Leu Pro Glu Asn Phe Asn Glu
                800                 805                 810 gct aag ttc atc acc ttc agc atg ttg atc ttc ttc atc gtc tgg atc    2919
Ala Lys Phe Ile Thr Phe Ser Met Leu Ile Phe Phe Ile Val Trp Ile
            815                 820                 825 tcc ttc atc ccc gcc tat gtc agc acc tac ggc aag ttt gtg tcg gcc    2967
Ser Phe Ile Pro Ala Tyr Val Ser Thr Tyr Gly Lys Phe Val Ser Ala
            830                 835                 840 gtg gag gtg att gcc atc ctg gcc tcc agc ttc ggg ctg ctg ggc tgc    3015
Val Glu Val Ile Ala Ile Leu Ala Ser Ser Phe Gly Leu Leu Gly Cys
845                 850                 855 att tac ttc aac aag tgt tac atc atc ctg ttc aag ccg tgc cgt aac    3063
Ile Tyr Phe Asn Lys Cys Tyr Ile Ile Leu Phe Lys Pro Cys Arg Asn
860                 865                 870                 875 acc atc gag gag gtg cgc tgc agc acg gcg gcc cac gcc ttc aag gtg    3111
Thr Ile Glu Glu Val Arg Cys Ser Thr Ala Ala His Ala Phe Lys Val
            880                 885                 890 gcg gcc cgg gcc acc ctc cgg cgc agc gcg gct cgc aag cgc tcc        3159
Ala Ala Arg Ala Thr Leu Arg Arg Ser Ala Ala Ser Arg Lys Arg Ser
            895                 900                 905 agc agc ctg tgc ggc tcc acc atc tcc tcg ccc gcc tcg tcc acc tgc    3207
Ser Ser Leu Cys Gly Ser Thr Ile Ser Ser Pro Ala Ser Ser Thr Cys
                910                 915                 920
```

FIG. 5D

```
ggg ccg ggc ctc acc atg gag atg cag cgc tgc agc acg cag aag gtc      3255
Gly Pro Gly Leu Thr Met Glu Met Gln Arg Cys Ser Thr Gln Lys Val
    925             930             935 agc ttc ggc agc ggc acc gtc acc ctg tcg ctc agc ttc gag gag aca      3303
Ser Phe Gly Ser Gly Thr Val Thr Leu Ser Leu Ser Phe Glu Glu Thr
940             945             950                 955 ggc cga tac gcc acc ctc agc cgc acg gcc cgc agc agg aac tcg gcg      3351
Gly Arg Tyr Ala Thr Leu Ser Arg Thr Ala Arg Ser Arg Asn Ser Ala
                960             965             970 gat ggc cgc agc ggc gac gac ctg cca tct aga cac cac gac cag ggc      3399
Asp Gly Arg Ser Gly Asp Asp Leu Pro Ser Arg His His Asp Gln Gly
            975             980             985 ccg cct cag aaa tgc gag ccc cag ccc gcc aac gat gcc cga tac aag      3447
Pro Pro Gln Lys Cys Glu Pro Gln Pro Ala Asn Asp Ala Arg Tyr Lys
        990             995             1000 gcg gcg ccg acc aag ggc acc cta gag tcg ccg ggc ggc agc aag gag      3495
Ala Ala Pro Thr Lys Gly Thr Leu Glu Ser Pro Gly Gly Ser Lys Glu
    1005            1010            1015 cgc ccc aca act atg gag gaa acc taa tccaactcct ccatcaaccc            3542
Arg Pro Thr Thr Met Glu Glu Thr
1020            1025 caagaacatc ctccacggca gcaccgtcga caactgacat caactcctaa ccggtggctg    3602
cccaacctct cccctctccg gcactttgcg ttttgctgaa gattgcagca tctgcagttc    3662
cttttatccc tgatttctg acttggatat ttactagtgt gcgatggaat atcacaacat     3722
aatgagttgc acaattaggt gagcagagtt gtgtcaaact atctgaacta tctgaagtat    3782
ctgaactact ttattctctc gaattgtatt acaaacattt gaagtatttt tagtgacatt    3842
atgttctaac attgtcaaga taatttgtta caacatataa ggtaccacct gaagcagtga    3902
ctgagattgc cactgtgatg acagaactgt tttataacat ttatcattga aacctggatt    3962
gcaacaggaa tataatgact gtaacaaaaa aattgttgat tatcttaaaa atgcaaattg    4022
taatcagatg tgtaaaattg gtaattactt ctgtacatta aatgcatatt tcttgataaa    4082
aaaaaaaaaa aaaaaaaaaa aaaaaaaaaa aaaagcggcc cgacagcaac gg            4134
```

FIG. 5E

```
cta cta gtc ata tgg att gcg gcg gay gay gat tat ggc cgc cca ggg    48
Leu Leu Val Ile Trp Ile Ala Ala Asp Asp Asp Tyr Gly Arg Pro Gly
 1               5                  10                  15 ata gat aag ttt cga gaa gaa gct gaa gag agg gac atc tgc ata gat    96
Ile Asp Lys Phe Arg Glu Glu Ala Glu Glu Arg Asp Ile Cys Ile Asp
                 20                  25                  30 ttc aat gag atg att tct cag tac tat aca caa aaa gag ctg gag ttt   144
Phe Asn Glu Met Ile Ser Gln Tyr Tyr Thr Gln Lys Glu Leu Glu Phe
             35                  40                  45 att gca gat act att cag aat tcc tca gcc aaa gtg att gty gtc ttc   192
Ile Ala Asp Thr Ile Gln Asn Ser Ser Ala Lys Val Ile Xaa Val Phe
         50                  55                  60 tca aat ggc cct gac ttg gaa cca cta ata caa gag ata gtt cga cgg   240
Ser Asn Gly Pro Asp Leu Glu Pro Leu Ile Gln Glu Ile Val Arg Arg
 65                  70                  75                  80 aac ata act gat aga ata tgg cta gca agt gaa gcg tgg gct agt tcc   288
Asn Ile Thr Asp Arg Ile Trp Leu Ala Ser Glu Ala Trp Ala Ser Ser
                 85                  90                  95 tca ctg ata gcc aaa cca gaa tac ttc cat gtt gtt ggt gga acc att   336
Ser Leu Ile Ala Lys Pro Glu Tyr Phe His Val Val Gly Gly Thr Ile
            100                 105                 110 gga ttt gca cta aga gca gga cgc atc cca gga ttc cat gag ttt tta   384
Gly Phe Ala Leu Arg Ala Gly Arg Ile Pro Gly Phe His Glu Phe Leu
        115                 120                 125 aaa aag gtc cat ccc agc agg tcc tcc cac aat ggc ttt gtc aag gaa   432
Lys Lys Val His Pro Ser Arg Ser Ser His Asn Gly Phe Val Lys Glu
    130                 135                 140 ttc tgg gaa gaa aca ttt aat tgt tat ttc act gaa gaa tcc cta aca   480
Phe Trp Glu Glu Thr Phe Asn Cys Tyr Phe Thr Glu Glu Ser Leu Thr
145                 150                 155                 160 caa cta aag aat tgc aaa aca cca acc cat gga tta gca atg cac aat   528
Gln Leu Lys Asn Cys Lys Thr Pro Thr His Gly Leu Ala Met His Asn
                165                 170                 175 gac agt gcg aaa atg ggg cat tcc aca agg aca acg tta cga cct cca   576
Asp Ser Ala Lys Met Gly His Ser Thr Arg Thr Thr Leu Arg Pro Pro
            180                 185                 190
```

Polynucleotide SEQ ID NO: 3; Polypeptide SEQ ID NO: 4

FIG. 16A

```
tgc act gga gaa gag aat atc acg agt gtg gag acc cct tac ctg gat    624
Cys Thr Gly Glu Glu Asn Ile Thr Ser Val Glu Thr Pro Tyr Leu Asp
        195                 200                 205 tat act cac ctc cgt att tca tat aat gtg tat gtg gca gtg tat tcg    672
Tyr Thr His Leu Arg Ile Ser Tyr Asn Val Tyr Val Ala Val Tyr Ser
        210                 215                 220 att gct cac gct ctg cag gac atc tat gcc tgc aca cct ggg aag ggg    720
Ile Ala His Ala Leu Gln Asp Ile Tyr Ala Cys Thr Pro Gly Lys Gly
225                 230                 235                 240 att ttt gcg aac gga tca tgt gcc gat atc aaa aaa gtc gaa gcc tgg    768
Ile Phe Ala Asn Gly Ser Cys Ala Asp Ile Lys Lys Val Glu Ala Trp
                245                 250                 255 aat cca tat gac tag t                                              784
Asn Pro Tyr Asp
            260
```

Polynucleotide SEQ ID NO: 3;  Polypeptide SEQ ID NO: 4 (CONTINUED)

FIG. 16B

```
Leu Leu Val Ile Trp Ile-Ala Ala Asp Asp Asp Tyr Gly Arg Pro Gly
 1           5               10                      15
Ile Asp Lys Phe Arg Glu Glu Ala Glu Glu Arg Asp Ile Cys Ile Asp
            20                  25                  30
Phe Asn Glu Met Ile Ser Gln Tyr Tyr Thr Gln Lys Glu Leu Glu Phe
            35                  40                  45
Ile Ala Asp Thr Ile Gln Asn Ser Ser Ala Lys Val Ile Val Val Phe
 50                     55                  60
Ser Asn Gly Pro Asp Leu Glu Pro Leu Ile Gln Glu Ile Val Arg Arg
65                      70                  75                  80
Asn Ile Thr Asp Arg Ile Trp Leu Ala Ser Glu Ala Trp Ala Ser Ser
                85                  90                      95
Ser Leu Ile Ala Lys Pro Glu Tyr Phe His Val Val Gly Gly Thr Ile
                100                 105                 110
Gly Phe Ala Leu Arg Ala Gly Arg Ile Pro Gly Phe His Glu Phe Leu
                115                 120                 125
Lys Lys Val His Pro Ser Arg Ser Ser His Asn Gly Phe Val Lys Glu
        130                 135                 140
Phe Trp Glu Glu Thr Phe Asn Cys Tyr Phe Thr Glu Glu Ser Leu Thr
145                 150                 155                 160
Gln Leu Lys Asn Cys Lys Thr Pro Thr His Gly Leu Ala Met His Asn
                165                 170                 175
Asp Ser Ala Lys Met Gly His Ser Thr Arg Thr Thr Leu Arg Pro Pro
                180                 185                 190
Cys Thr Gly Glu Glu Asn Ile Thr Ser Val Glu Thr Pro Tyr Leu Asp
        195                 200                 205
Tyr Thr His Leu Arg Ile Ser Tyr Asn Val Tyr Val Ala Val Tyr Ser
        210                 215                 220
Ile Ala His Ala Leu Gln Asp Ile Tyr Ala Cys Thr Pro Gly Lys Gly
225                 230                 235                 240
Ile Phe Ala Asn Gly Ser Cys Ala Asp Ile Lys Lys Val Glu Ala Trp
                245                 250                 255
Asn Pro Tyr Asp
        260
```

Polypeptide SEQ ID NO: 4

FIG. 17

Polynucleotide SEQ ID NO: 3;  Polypeptide SEQ ID NO: 4

```
          10          20          30          40          50
           *           *           *           *           *
CTA CTA GTC ATA TGG ATT GCG GCG GAY GAY GAT TAT GGC CGC CCA GGG ATA GAT
GAT GAT CAG TAT ACC TAA CGC CGC CTR CTR CTA ATA CCG GCG GGT CCC TAT CTA
Leu Leu Val Ile Trp Ile Ala Ala Asp Asp Asp Tyr Gly Arg Pro Gly Ile Asp>
___a___a___a___a___a___a___a___a__ORF RF[1] ___a___a___a___a___a___a___a___>

60          70          80          90         100
           *           *           *           *           *
AAG TTT CGA GAA GAA GCT GAA GAG AGG GAC ATC TGC ATA GAT TTC AAT GAG ATG
TTC AAA GCT CTT CTT CGA CTT CTC TCC CTG TAG ACG TAT CTA AAG TTA CTC TAC
Lys Phe Arg Glu Glu Ala Glu Glu Arg Asp Ile Cys Ile Asp Phe Asn Glu Met>
___a___a___a___a___a___a___a___a__ORF RF[1] ___a___a___a___a___a___a___a___>

110         120         130         140         150         160
   *           *           *           *           *           *
ATT TCT CAG TAC TAT ACA CAA AAA GAG CTG GAG TTT ATT GCA GAT ACT ATT CAG
TAA AGA GTC ATG ATA TGT GTT TTT CTC GAC CTC AAA TAA CGT CTA TGA TAA GTC
Ile Ser Gln Tyr Tyr Thr Gln Lys Glu Leu Glu Phe Ile Ala Asp Thr Ile Gln>
___a___a___a___a___a___a___a___a__ORF RF[1] ___a___a___a___a___a___a___a___>

170         180         190         200         210
          *           *           *           *           *
AAT TCC TCA GCC AAA GTG ATT GTY GTC TTC TCA AAT GGC CCT GAC TTG GAA CCA
TTA AGG AGT CGG TTT CAC TAA CAR CAG AAG AGT TTA CCG GGA CTG AAC CTT GGT
Asn Ser Ser Ala Lys Val Ile Val Val Phe Ser Asn Gly Pro Asp Leu Glu Pro>
___a___a___a___a___a___a___a___a__ORF RF[1] ___a___a___a___a___a___a___a___>

220         230         240         250         260         270
   *           *           *           *           *           *
CTA ATA CAA GAG ATA GTT CGA CGG AAC ATA ACT GAT AGA ATA TGG CTA GCA AGT
GAT TAT GTT CTC TAT CAA GCT GCC TTG TAT TGA CTA TCT TAT ACC GAT CGT TCA
Leu Ile Gln Glu Ile Val Arg Arg Asn Ile Thr Asp Arg Ile Trp Leu Ala Ser>
___a___a___a___a___a___a___a___a__ORF RF[1] ___a___a___a___a___a___a___a___>

280         290         300         310         320
          *           *           *           *           *
GAA GCG TGG GCT AGT TCC TCA CTG ATA GCC AAA CCA GAA TAC TTC CAT GTT GTT
CTT CGC ACC CGA TCA AGG AGT GAC TAT CGG TTT GGT CTT ATG AAG GTA CAA CAA
Glu Ala Trp Ala Ser Ser Ser Leu Ile Ala Lys Pro Glu Tyr Phe His Val Val>
___a___a___a___a___a___a___a___a__ORF RF[1] ___a___a___a___a___a___a___a___>

330         340         350         360         370
   *           *           *           *           *
GGT GGA ACC ATT GGA TTT GCA CTA AGA GCA GGA CGC ATC CCA GGA TTC CAT GAG
CCA CCT TGG TAA CCT AAA CGT GAT TCT CGT CCT GCG TAG GGT CCT AAG GTA CTC
Gly Gly Thr Ile Gly Phe Ala Leu Arg Ala Gly Arg Ile Pro Gly Phe His Glu>
___a___a___a___a___a___a___a___a__ORF RF[1] ___a___a___a___a___a___a___a___>

380         390         400         410         420         430
  *           *           *           *           *           *
TTT TTA AAA AAG GTC CAT CCC AGC AGG TCC TCC CAC AAT GGC TTT GTC AAG GAA
AAA AAT TTT TTC CAG GTA GGG TCG TCC AGG AGG GTG TTA CCG AAA CAG TTC CTT
Phe Leu Lys Lys Val His Pro Ser Arg Ser Ser His Asn Gly Phe Val Lys Glu>
___a___a___a___a___a___a___a___a__ORF RF[1] ___a___a___a___a___a___a___a___>

440         450         460         470         480
          *           *           *           *           *
TTC TGG GAA GAA ACA TTT AAT TGT TAT TTC ACT GAA GAA TCC CTA ACA CAA CTA
AAG ACC CTT CTT TGT AAA TTA ACA ATA AAG TGA CTT CTT AGG GAT TGT GTT GAT
Phe Trp Glu Glu Thr Phe Asn Cys Tyr Phe Thr Glu Glu Ser Leu Thr Gln Leu>
___a___a___a___a___a___a___a___a__ORF RF[1] ___a___a___a___a___a___a___a___>
```

FIG. 18A

Polynucleotide SEQ ID NO: 3;  Polypeptide SEQ ID NO: 4 (CONTINUED)

```
        490         500         510         520         530         540
         *           *           *           *           *           *
   AAG AAT TGC AAA ACA CCA ACC CAT GGA TTA GCA ATG CAC AAT GAC AGT GCG AAA
   TTC TTA ACG TTT TGT GGT TGG GTA CCT AAT CGT TAC GTG TTA CTG TCA CGC TTT
   Lys Asn Cys Lys Thr Pro Thr His Gly Leu Ala Met His Asn Asp Ser Ala Lys>
   ___a___a___a___a___a___a___a__ORF RF[1] ___a___a___a___a___a___a___a___>

550         560         570         580         590
           *           *           *           *           *
     ATG GGG CAT TCC ACA AGG ACA ACG TTA CGA CCT CCA TGC ACT GGA GAA GAG AAT
     TAC CCC GTA AGG TGT TCC TGT TGC AAT GCT GGA GGT ACG TGA CCT CTT CTC TTA
     Met Gly His Ser Thr Arg Thr Thr Leu Arg Pro Pro Cys Thr Gly Glu Glu Asn>
     ___a___a___a___a___a___a___a__ORF RF[1] ___a___a___a___a___a___a___a___>

600         610         620         630         640
          *           *           *           *           *
    ATC ACG AGT GTG GAG ACC CCT TAC CTG GAT TAT ACT CAC CTC CGT ATT TCA TAT
    TAG TGC TCA CAC CTC TGG GGA ATG GAC CTA ATA TGA GTG GAG GCA TAA AGT ATA
    Ile Thr Ser Val Glu Thr Pro Tyr Leu Asp Tyr Thr His Leu Arg Ile Ser Tyr>
    ___a___a___a___a___a___a___a__ORF RF[1] ___a___a___a___a___a___a___a___>

650         660         670         680         690         700
    *           *           *           *           *           *
   AAT GTG TAT GTG GCA GTG TAT TCG ATT GCT CAC GCT CTG CAG GAC ATC TAT GCC
   TTA CAC ATA CAC CGT CAC ATA AGC TAA CGA GTG CGA GAC GTC CTG TAG ATA CGG
   Asn Val Tyr Val Ala Val Tyr Ser Ile Ala His Ala Leu Gln Asp Ile Tyr Ala>
   ___a___a___a___a___a___a___a__ORF RF[1] ___a___a___a___a___a___a___a___>

710         720         730         740         750
           *           *           *           *           *
     TGC ACA CCT GGG AAG GGG ATT TTT GCG AAC GGA TCA TGT GCC GAT ATC AAA AAA
     ACG TGT GGA CCC TTC CCC TAA AAA CGC TTG CCT AGT ACA CGG CTA TAG TTT TTT
     Cys Thr Pro Gly Lys Gly Ile Phe Ala Asn Gly Ser Cys Ala Asp Ile Lys Lys>
     ___a___a___a___a___a___a___a__ORF RF[1] ___a___a___a___a___a___a___a___>

760         770         780
       *           *           *
   GTC GAA GCC TGG AAT CCA TAT GAC TAGT
   CAG CTT CGG ACC TTA GGT ATA CTG ATCA
   Val Glu Ala Trp Asn Pro Tyr Asp>
   ___a___a__ORF RF[1] ___a___a___>
```

FIG. 18B

```
tt ctg aca ata ttt gct gtg cta gga ata ctg atc act tcc ttt gtt      47
   Leu Thr Ile Phe Ala Val Leu Gly Ile Leu Ile Thr Ser Phe Val
     1               5                  10                  15 ttg gga gta ttc att aag ttc aga aat act cct att gtg aaa gcc act      95
Leu Gly Val Phe Ile Lys Phe Arg Asn Thr Pro Ile Val Lys Ala Thr
                 20                  25                  30 aac aga gaa ctc tcc tat ctc ctc ctc ttc tcc tta atc tgc tgt ttc     143
Asn Arg Glu Leu Ser Tyr Leu Leu Leu Phe Ser Leu Ile Cys Cys Phe
             35                  40                  45 tcc agc tca ttg atc ttc att gga gaa ccc aaa gat tgg acc tgc aga     191
Ser Ser Ser Leu Ile Phe Ile Gly Glu Pro Lys Asp Trp Thr Cys Arg
         50                  55                  60 ctg cgt caa cct gca ttt gga atc agc ttt gtg ctg tgc att tct tgc     239
Leu Arg Gln Pro Ala Phe Gly Ile Ser Phe Val Leu Cys Ile Ser Cys
     65                  70                  75 att ctg gtg aaa act aat cgt gta cta ttg gtc ttt gag gcc aag atc     287
Ile Leu Val Lys Thr Asn Arg Val Leu Leu Val Phe Glu Ala Lys Ile
 80                  85                  90                  95 cca act agc ctc cat cga aag tgg gtg ggc ctc aat ttg caa ttc tta     335
Pro Thr Ser Leu His Arg Lys Trp Val Gly Leu Asn Leu Gln Phe Leu
                100                 105                 110 ctg gtt ttc ctc tgt att ctt gtg caa att gtt act tgt gtc atc tgg     383
Leu Val Phe Leu Cys Ile Leu Val Gln Ile Val Thr Cys Val Ile Trp
            115                 120                 125 ctt tac aca gca ccc cct tcg agc tac aga aat cat gaa cta gaa gat     431
Leu Tyr Thr Ala Pro Pro Ser Ser Tyr Arg Asn His Glu Leu Glu Asp
        130                 135                 140 gaa atc att ttt att aca tgt gat gaa ggt tcc tta atg gca ctt ggt     479
Glu Ile Ile Phe Ile Thr Cys Asp Glu Gly Ser Leu Met Ala Leu Gly
145                 150                 155 ttt ctc att ggt tac aca tgc ctc ctt gct gcc att tgc ttc ttt ttt     527
Phe Leu Ile Gly Tyr Thr Cys Leu Leu Ala Ala Ile Cys Phe Phe Phe
160                 165                 170                 175 gcc ttt aag tct cgc aaa ctc cca gag aac ttc aat gag gcc aaa ttt     575
Ala Phe Lys Ser Arg Lys Leu Pro Glu Asn Phe Asn Glu Ala Lys Phe
                180                 185                 190 att acc ttc agc atg ctg ata tt                                      598
Ile Thr Phe Ser Met Leu Ile
                195
```

Polynucleotide SEQ ID NO: 5; Polypeptide SEQ ID NO: 6

FIG. 19

```
Leu Thr Ile Phe Ala Val Leu Gly Ile Leu Ile Thr Ser Phe Val Leu
 1               5              10              15
Gly Val Phe Ile Lys Phe Arg Asn Thr Pro Ile Val Lys Ala Thr Asn
             20              25              30
Arg Glu Leu Ser Tyr Leu Leu Leu Phe Ser Leu Ile Cys Cys Phe Ser
         35              40              45
Ser Ser Leu Ile Phe Ile Gly Glu Pro Lys Asp Trp Thr Cys Arg Leu
     50              55              60
Arg Gln Pro Ala Phe Gly Ile Ser Phe Val Leu Cys Ile Ser Cys Ile
65              70              75              80
Leu Val Lys Thr Asn Arg Val Leu Leu Val Phe Glu Ala Lys Ile Pro
             85              90              95
Thr Ser Leu His Arg Lys Trp Val Gly Leu Asn Leu Gln Phe Leu Leu
            100             105             110
Val Phe Leu Cys Ile Leu Val Gln Ile Val Thr Cys Val Ile Trp Leu
            115             120             125
Tyr Thr Ala Pro Pro Ser Ser Tyr Arg Asn His Glu Leu Glu Asp Glu
        130             135             140
Ile Ile Phe Ile Thr Cys Asp Glu Gly Ser Leu Met Ala Leu Gly Phe
145             150             155             160
Leu Ile Gly Tyr Thr Cys Leu Leu Ala Ala Ile Cys Phe Phe Phe Ala
            165             170             175
Phe Lys Ser Arg Lys Leu Pro Glu Asn Phe Asn Glu Ala Lys Phe Ile
            180             185             190
Thr Phe Ser Met Leu Ile
            195
```

Polypeptide SEQ ID NO: 6

FIG. 20

Polynucleotide SEQ ID NO: 5;   Polypeptide SEQ ID NO: 6

```
             10          20          30          40          50
              *           *           *           *           *
TT CTG ACA ATA TTT GCT GTG CTA GGA ATA CTG ATC ACT TCC TTT GTT TTG GGA
AA GAC TGT TAT AAA CGA CAC GAT CCT TAT GAC TAG TGA AGG AAA CAA AAC CCT
   Leu Thr Ile Phe Ala Val Leu Gly Ile Leu Ile Thr Ser Phe Val Leu Gly>
   ___a___a___a___a___a___a___ORF RF[3] _a___a___a___a___a___a___a___>

60          70          80          90         100
           *           *           *           *           *
GTA TTC ATT AAG TTC AGA AAT ACT CCT ATT GTG AAA GCC ACT AAC AGA GAA CTC
CAT AAG TAA TTC AAG TCT TTA TGA GGA TAA CAC TTT CGG TGA TTG TCT CTT GAG
Val Phe Ile Lys Phe Arg Asn Thr Pro Ile Val Lys Ala Thr Asn Arg Glu Leu>
___a___a___a___a___a___a___a__ORF RF[3] ___a___a___a___a___a___a___a___>

110         120         130         140         150         160
    *           *           *           *           *           *
TCC TAT CTC CTC CTC TTC TCC TTA ATC TGC TGT TTC TCC AGC TCA TTG ATC TTC
AGG ATA GAG GAG GAG AAG AGG AAT TAG ACG ACA AAG AGG TCG AGT AAC TAG AAG
Ser Tyr Leu Leu Leu Phe Ser Leu Ile Cys Cys Phe Ser Ser Ser Leu Ile Phe>
___a___a___a___a___a___a___a__ORF RF[3] ___a___a___a___a___a___a___a___>

170         180         190         200         210
           *           *           *           *           *
ATT GGA GAA CCC AAA GAT TGG ACC TGC AGA CTG CGT CAA CCT GCA TTT GGA ATC
TAA CCT CTT GGG TTT CTA ACC TGG ACG TCT GAC GCA GTT GGA CGT AAA CCT TAG
Ile Gly Glu Pro Lys Asp Trp Thr Cys Arg Leu Arg Gln Pro Ala Phe Gly Ile>
___a___a___a___a___a___a___a__ORF RF[3] ___a___a___a___a___a___a___a___>

220         230         240         250         260
       *           *           *           *           *
AGC TTT GTG CTG TGC ATT TCT TGC ATT CTG GTG AAA ACT AAT CGT GTG CTA TTG
TCG AAA CAC GAC ACG TAA AGA ACG TAA GAC CAC TTT TGA TTA GCA CAC GAT AAC
Ser Phe Val Leu Cys Ile Ser Cys Ile Leu Val Lys Thr Asn Arg Val Leu Leu>
___a___a___a___a___a___a___a__ORF RF[3] ___a___a___a___a___a___a___a___>

70         280         290         300         310         320
    *           *           *           *           *           *
GTC TTT GAG GCC AAG ATC CCA ACT AGC CTC CAT CGA AAG TGG GTG GGC CTC AAT
CAG AAA CTC CGG TTC TAG GGT TGA TCG GAG GTA GCT TTC ACC CAC CCG GAG TTA
Val Phe Glu Ala Lys Ile Pro Thr Ser Leu His Arg Lys Trp Val Gly Leu Asn>
___a___a___a___a___a___a___a__ORF RF[3] ___a___a___a___a___a___a___a___>

330         340         350         360         370
          *           *           *           *           *
TTG CAA TTC TTA CTG GTT TTC CTC TGT ATT CTT GTG CAA ATT GTT ACT TGT GTC
AAC GTT AAG AAT GAC CAA AAG GAG ACA TAA GAA CAC GTT TAA CAA TGA ACA CAG
Leu Gln Phe Leu Leu Val Phe Leu Cys Ile Leu Val Gln Ile Val Thr Cys Val>
___a___a___a___a___a___a___a__ORF RF[3] ___a___a___a___a___a___a___a___>

380         390         400         410         420         430
  *           *           *           *           *           *
ATC TGG CTT TAC ACA GCA CCC CCT TCG AGC TAC AGA AAT CAT GAA CTA GAA GAT
TAG ACC GAA ATG TGT CGT GGG GGA AGC TCG ATG TCT TTA GTA CTT GAT CTT CTA
Ile Trp Leu Tyr Thr Ala Pro Pro Ser Ser Tyr Arg Asn His Glu Leu Glu Asp>
___a___a___a___a___a___a___a__ORF RF[3] ___a___a___a___a___a___a___a___>

440         450         460         470         480
          *           *           *           *           *
GAA ATC ATT TTT ATT ACA TGT GAT GAA GGT TCC TTA ATG GCA CTT GGT TTT CTC
CTT TAG TAA AAA TAA TGT ACA CTA CTT CCA AGG AAT TAC CGT GAA CCA AAA GAG
Glu Ile Ile Phe Ile Thr Cys Asp Glu Gly Ser Leu Met Ala Leu Gly Phe Leu>
___a___a___a___a___a___a___a__ORF RF[3] ___a___a___a___a___a___a___a___>
```

FIG. 21A

Polynucleotide SEQ ID NO: 5;  Polypeptide SEQ ID NO: 6 (CONTINUED)

```
       490         500         510         520         530
        *           *           *           *           *
ATT GGT TAC ACA TGC CTC CTT GCT GCC ATT TGC TTC TTT TTT GCC TTT AAG TCT
TAA CCA ATG TGT ACG GAG GAA CGA CGG TAA ACG AAG AAA AAA CGG AAA TTC AGA
Ile Gly Tyr Thr Cys Leu Leu Ala Ala Ile Cys Phe Phe Phe Ala Phe Lys Ser>
___a___a___a___a___a___a___a___a___a__ORF RF[3] ___a___a___a___a___a___a___a___>

540         550         560         570         580         590
 *           *           *           *           *           *
CGC AAA CTC CCA GAG AAC TTC AAT GAG GCC AAA TTT ATT ACC TTC AGC ATG CTG
GCG TTT GAG GGT CTC TTG AAG TTA CTC CGG TTT AAA TAA TGG AAG TCG TAC GAC
Arg Lys Leu Pro Glu Asn Phe Asn Glu Ala Lys Phe Ile Thr Phe Ser Met Leu>
___a___a___a___a___a___a___a___a__ORF RF[3] ___a___a___a___a___a___a___a___>
ATA TT
TAT AA
Ile>
___>
```

FIG. 21B

Polynucleotide SEQ ID NO: 7; Polypeptide SEQ ID NO: 8

```
  g ttg acc ata tgt gca gtg ctg ggt gtt gcc ytg acg ggc ttc gtg atg      49
    Leu Thr Ile Cys Ala Val Leu Gly Val Ala Xaa Thr Gly Phe Val Met
     1               5                  10                  15 gcc gtc ttt gtc cga ttc cgc aac acc cca ata gtg aaa gcc acg aac          97
Ala Val Phe Val Arg Phe Arg Asn Thr Pro Ile Val Lys Ala Thr Asn
                20                  25                  30 cga gaa ctg tcc tac gtc ctc ctg ttc tct ctc atc tgt tgc ttc tcc         145
Arg Glu Leu Ser Tyr Val Leu Leu Phe Ser Leu Ile Cys Cys Phe Ser
         35                  40                  45 agc tcc ctc atc ttc ata gga gag ccg cag gat tgg atg tgc cgc tta         193
Ser Ser Leu Ile Phe Ile Gly Glu Pro Gln Asp Trp Met Cys Arg Leu
             50                  55                  60 cgc caa ccg gcc ttt ggg atc agt ttt gtt ctc tgt atc tcg tgc atc         241
Arg Gln Pro Ala Phe Gly Ile Ser Phe Val Leu Cys Ile Ser Cys Ile
 65                  70                  75                  80 ctt gtg aaa aca aac cka gtc ctc ttg gtg ttt gaa gcc aag atc ccg         289
Leu Val Lys Thr Asn Xaa Val Leu Leu Val Phe Glu Ala Lys Ile Pro
                 85                  90                  95 aca agt ctc cat cgt aaa tgg tgg ggg tta aac cta cag ttc ctg ctg         337
Thr Ser Leu His Arg Lys Trp Trp Gly Leu Asn Leu Gln Phe Leu Leu
                100                 105                 110 gtg ttt ctg tgc aca ttt gtc caa gtc atg ata tgt gtg gtc tgg ctg         385
Val Phe Leu Cys Thr Phe Val Gln Val Met Ile Cys Val Val Trp Leu
             115                 120                 125 tac aac gcc cca cct tcc agt tac agg aat tat gac ata gat gag atg         433
Tyr Asn Ala Pro Pro Ser Ser Tyr Arg Asn Tyr Asp Ile Asp Glu Met
         130                 135                 140 att ttt atc aca tgt aat gaa ggc tct gta atg gct ctt ggg ttt ctt         481
Ile Phe Ile Thr Cys Asn Glu Gly Ser Val Met Ala Leu Gly Phe Leu
145                 150                 155                 160 att ggc tat aca tgc ctg ctg gcc gct ata tgt ttc ttc ttt gca ttc         529
Ile Gly Tyr Thr Cys Leu Leu Ala Ala Ile Cys Phe Phe Phe Ala Phe
                165                 170                 175 aaa tca cgg aaa ctt cca gaa aac ttc acc gag gct aag ttc atc act         577
Lys Ser Arg Lys Leu Pro Glu Asn Phe Thr Glu Ala Lys Phe Ile Thr
             180                 185                 190 ttt agt atg ctc ata tt                                                  594
Phe Ser Met Leu Ile
         195
```

FIG. 22

Leu Thr Ile Cys Ala Val Leu Gly Val Ala Leu Thr Gly Phe Val Met
1               5                   10                  15
Ala Val Phe Val Arg Phe Arg Asn Thr Pro Ile Val Lys Ala Thr Asn
            20                  25                  30
Arg Glu Leu Ser Tyr Val Leu Leu Phe Ser Leu Ile Cys Cys Phe Ser
        35                  40                  45
Ser Ser Leu Ile Phe Ile Gly Glu Pro Gln Asp Trp Met Cys Arg Leu
    50                  55                  60
Arg Gln Pro Ala Phe Gly Ile Ser Phe Val Leu Cys Ile Ser Cys Ile
65              70                  75                  80
Leu Val Lys Thr Asn Xaa Val Leu Leu Val Phe Glu Ala Lys Ile Pro
            85                  90                  95
Thr Ser Leu His Arg Lys Trp Trp Gly Leu Asn Leu Gln Phe Leu Leu
            100                 105                 110
Val Phe Leu Cys Thr Phe Val Gln Val Met Ile Cys Val Val Trp Leu
        115                 120                 125
Tyr Asn Ala Pro Pro Ser Ser Tyr Arg Asn Tyr Asp Ile Asp Glu Met
130                 135                 140
Ile Phe Ile Thr Cys Asn Glu Gly Ser Val Met Ala Leu Gly Phe Leu
145                 150                 155                 160
Ile Gly Tyr Thr Cys Leu Leu Ala Ala Ile Cys Phe Phe Phe Ala Phe
                165                 170                 175
Lys Ser Arg Lys Leu Pro Glu Asn Phe Thr Glu Ala Lys Phe Ile Thr
            180                 185                 190
Phe Ser Met Leu Ile
            195

Polypeptide SEQ ID NO: 8

FIG. 23

Polynucleotide SEQ ID NO: 7;    Polypeptide SEQ ID NO: 8

```
             10             20             30             40             50
              *              *              *              *              *
G TTG ACC ATA TGT GCA GTG CTG GGT GTT GCC YTG ACG GGC TTC GTG ATG GCC
C AAC TGG TAT ACA CGT CAC GAC CCA CAA CGG RAC TGC CCG AAG CAC TAC CGG
  Leu Thr Ile Cys Ala Val Leu Gly Val Ala Leu Thr Gly Phe Val Met Ala>
  ___a___a___a___a___a___a____ORF RF[2] _a___a___a___a___a___a___a___>

60             70             80             90            100
              *              *              *              *              *
GTC TTT GTC CGA TTC CGC AAC ACC CCA ATA GTG AAA GCC ACG AAC CGA GAA CTG
CAG AAA CAG GCT AAG GCG TTG TGG GGT TAT CAC TTT CGG TGC TTG GCT CTT GAC
Val Phe Val Arg Phe Arg Asn Thr Pro Ile Val Lys Ala Thr Asn Arg Glu Leu>
___a___a___a___a___a___a___a_ORF RF[2] ___a___a___a___a___a___a___a___>

110            120            130            140            150            160
              *              *              *              *              *              *
TCC TAC GTC CTC CTG TTC TCT CTC ATC TGT TGC TTC TCC AGC TCC CTC ATC TTC
AGG ATG CAG GAG GAC AAG AGA GAG TAG ACA ACG AAG AGG TCG AGG GAG TAG AAG
Ser Tyr Val Leu Leu Phe Ser Leu Ile Cys Cys Phe Ser Ser Ser Leu Ile Phe>
___a___a___a___a___a___a___a_ORF RF[2] ___a___a___a___a___a___a___a___>

170            180            190            200            210
              *              *              *              *              *
ATA GGA GAG CCG CAG GAT TGG ATG TGC CGC TTA CGC AAC CCG GCC TTT GGG ATC
TAT CCT CTC GGC GTC CTA ACC TAC ACG GCG AAT GCG TTG GCC GGG AAA CCC TAG
Ile Gly Glu Pro Gln Asp Trp Met Cys Arg Leu Arg Gln Pro Ala Phe Gly Ile>
___a___a___a___a___a___a___a_ORF RF[2] ___a___a___a___a___a___a___a___>

220            230            240            250            260
              *              *              *              *              *
AGT TTT GTT CTC TGT ATC TCG TGC ATC CTT GTG AAA ACA AAC CKA GTC CTC TTG
TCA AAA CAA GAG ACA TAG AGC ACG TAG GAA CAC TTT TGT TTG GMT CAG GAG AAC
Ser Phe Val Leu Cys Ile Ser Cys Ile Leu Val Lys Thr Asn Xxx Val Leu Leu>
___a___a___a___a___a___a___a_ORF RF[2] ___a___a___a___a___a___a___a___>

270            280            290            300            310            320
              *              *              *              *              *              *
GTG TTT GAA GCC AAG ATC CCG ACA AGT CTC CAT CGT AAA TGG TGG GGG TTA AAC
CAC AAA CTT CGG TTC TAG GGC TGT TCA GAG GTA GCA TTT ACC ACC CCC AAT TTG
Val Phe Glu Ala Lys Ile Pro Thr Ser Leu His Arg Lys Trp Trp Gly Leu Asn>
___a___a___a___a___a___a___a_ORF RF[2] ___a___a___a___a___a___a___a___>

330            340            350            360            370
              *              *              *              *              *
CTA CAG TTC CTG CTG GTG TTT CTG TGC ACA TTT GTC CAA GTC ATG ATA TGT GTG
GAT GTC AAG GAC GAC CAC AAA GAC ACG TGT AAA CAG GTT CAG TAC TAT ACA CAC
Leu Gln Phe Leu Leu Val Phe Leu Cys Thr Phe Val Gln Val Met Ile Cys Val>
___a___a___a___a___a___a___a_ORF RF[2] ___a___a___a___a___a___a___a___>

380            390            400            410            420            430
              *              *              *              *              *              *
GTC TGG CTG TAC AAC GCC CCA CCT TCC AGT TAC AGG AAT TAT GAC ATA GAT GAG
CAG ACC GAC ATG TTG CGG GGT GGA AGG TCA ATG TCC TTA ATA CTG TAT CTA CTC
Val Trp Leu Tyr Asn Ala Pro Pro Ser Ser Tyr Arg Asn Tyr Asp Ile Asp Glu>
___a___a___a___a___a___a___a_ORF RF[2] ___a___a___a___a___a___a___a___>

440            450            460            470            480
              *              *              *              *              *
ATG ATT TTT ATC ACA TGT AAT GAA GGC TCT GTA ATG GCT CTT GGG TTT CTT ATT
TAC TAA AAA TAG TGT ACA TTA CTT CCG AGA CAT TAC CGA GAA CCC AAA GAA TAA
Met Ile Phe Ile Thr Cys Asn Glu Gly Ser Val Met Ala Leu Gly Phe Leu Ile>
___a___a___a___a___a___a___a_ORF RF[2] ___a___a___a___a___a___a___a___>
```

FIG. 24A

Polynucleotide SEQ ID NO: 7;    Polypeptide SEQ ID NO: 8 (CONTINUED)

```
        490         500         510         520         530
         *           *           *           *           *
GGC TAT ACA TGC CTG CTG GCC GCT ATA TGT TTC TTC TTT GCA TTC AAA TCA CGG
CCG ATA TGT ACG GAC GAC CGG CGA TAT ACA AAG AAG AAA CGT AAG TTT AGT GCC
Gly Tyr Thr Cys Leu Leu Ala Ala Ile Cys Phe Phe Phe Ala Phe Lys Ser Arg>
___a___a___a___a___a___a___a___a__ORF RF[2] ___a___a___a___a___a___a___a___>

540         550         560         570         580         590
 *           *           *           *           *           *
AAA CTT CCA GAA AAC TTC ACC GAG GCT AAG TTC ATC ACT TTT AGT ATG CTC ATA
TTT GAA GGT CTT TTG AAG TGG CTC CGA TTC AAG TAG TGA AAA TCA TAC GAG TAT
Lys Leu Pro Glu Asn Phe Thr Glu Ala Lys Phe Ile Thr Phe Ser Met Leu Ile>
___a___a___a___a___a___a___a__ORF RF[2] ___a___a___a___a___a___a___a___>

```
tg tcg tgg acg gag ccc ttt ggg atc gcg ttg gcc ata tgt gca gcg      47
   Ser Trp Thr Glu Pro Phe Gly Ile Ala Leu Ala Ile Cys Ala Ala
    1               5                  10                  15 ctg ggt gtt gcc ttg acg ggc ttc gtg atg gcc gtc ttt atc aga ttc     95
Leu Gly Val Ala Leu Thr Gly Phe Val Met Ala Val Phe Ile Arg Phe
                 20                  25                  30 cgc aac acc cca ata gtg aag gcc acg aac cga gaa ctg tcc tat gtc    143
Arg Asn Thr Pro Ile Val Lys Ala Thr Asn Arg Glu Leu Ser Tyr Val
                 35                  40                  45 ctc ctg ttc tct ctc atc tgt tgc ttc tcc agt tcc ctc atc ttt att    191
Leu Leu Phe Ser Leu Ile Cys Cys Phe Ser Ser Ser Leu Ile Phe Ile
             50                  55                  60 gga gag ccg cag gat tgg atg tgt cgt tta cgc caa cct gcc ttt ggg    239
Gly Glu Pro Gln Asp Trp Met Cys Arg Leu Arg Gln Pro Ala Phe Gly
 65                  70                  75 atc agt ttt gtt ctc tgt atc tcc tgc atc ctt gtg aaa act aat aga    287
Ile Ser Phe Val Leu Cys Ile Ser Cys Ile Leu Val Lys Thr Asn Arg
 80                  85                  90                  95 gta ctc tta gta ttt gaa gcc aag atc ccc aca agt ctc cat cgt aaa    335
Val Leu Leu Val Phe Glu Ala Lys Ile Pro Thr Ser Leu His Arg Lys
                100                 105                 110 tgg tgg ggg tta aac ctt cag ttt ttg ctg gtg ttt ctg tgc aca ttt    383
Trp Trp Gly Leu Asn Leu Gln Phe Leu Leu Val Phe Leu Cys Thr Phe
                115                 120                 125 gtc caa gtc atg atc tgt gtt gtc tgg ctg tac aat gcc cct ccc tcc    431
Val Gln Val Met Ile Cys Val Val Trp Leu Tyr Asn Ala Pro Pro Ser
            130                 135                 140 agt tac agg aat tat gac ata gat gag atg att ttt atc aca            473
Ser Tyr Arg Asn Tyr Asp Ile Asp Glu Met Ile Phe Ile Thr
145                 150                 155 tg                                                                 475
```

Polynucleotide SEQ ID NO: 9;    Polypeptide SEQ ID NO: 10

FIG. 25

```
Ser Trp Thr Glu Pro Phe Gly Ile Ala Leu Ala Ile Cys Ala Ala Leu
 1           5                   10                  15
Gly Val Ala Leu Thr Gly Phe Val Met Ala Val Phe Ile Arg Phe Arg
            20                  25                  30
Asn Thr Pro Ile Val Lys Ala Thr Asn Arg Glu Leu Ser Tyr Val Leu
            35                  40                  45
Leu Phe Ser Leu Ile Cys Cys Phe Ser Ser Ser Leu Ile Phe Ile Gly
     50                  55                  60
Glu Pro Gln Asp Trp Met Cys Arg Leu Arg Gln Pro Ala Phe Gly Ile
65                   70                  75                   80
Ser Phe Val Leu Cys Ile Ser Cys Ile Leu Val Lys Thr Asn Arg Val
                85                  90                  95
Leu Leu Val Phe Glu Ala Lys Ile Pro Thr Ser Leu His Arg Lys Trp
               100                 105                110
Trp Gly Leu Asn Leu Gln Phe Leu Leu Val Phe Leu Cys Thr Phe Val
           115                 120                 125
Gln Val Met Ile Cys Val Val Trp Leu Tyr Asn Ala Pro Pro Ser Ser
       130                 135                 140
Tyr Arg Asn Tyr Asp Ile Asp Glu Met Ile Phe Ile Thr
145                 150                 155
```

Polypeptide SEQ ID NO: 10

FIG. 26

Polynucleotide SEQ ID NO: 9;    Polypeptide SEQ ID NO: 10

```
            10          20          30          40          50
            *           *           *           *           *
TG TCG TGG ACG GAG CCC TTT GGG ATC GCG TTG GCC ATA TGT GCA GCG CTG GGT
AC AGC ACC TGC CTC GGG AAA CCC TAG CGC AAC CGG TAT ACA CGT CGC GAC CCA
   Ser Trp Thr Glu Pro Phe Gly Ile Ala Leu Ala Ile Cys Ala Ala Leu Gly>
   ___a___a___a___a___a___a____ORF RF[3] _a___a___a___a___a___a___a___>

60          70          80          90          100
            *           *           *           *           *
GTT GCC TTG ACG GGC TTC GTG ATG GCC GTC TTT ATC AGA TTC CGC AAC ACC CCA
CAA CGG AAC TGC CCG AAG CAC TAC CGG CAG AAA TAG TCT AAG GCG TTG TGG GGT
Val Ala Leu Thr Gly Phe Val Met Ala Val Phe Ile Arg Phe Arg Asn Thr Pro>
___a___a___a___a___a___a___a__ORF RF[3] ___a___a___a___a___a___a___a___>

110         120         130         140         150         160
       *           *           *           *           *           *
ATA GTG AAG GCC ACG AAC CGA GAA CTG TCC TAT GTC CTC CTG TTC TCT CTC ATC
TAT CAC TTC CGG TGC TTG GCT CTT GAC AGG ATA CAG GAG GAC AAG AGA GAG TAG
Ile Val Lys Ala Thr Asn Arg Glu Leu Ser Tyr Val Leu Leu Phe Ser Leu Ile>
___a___a___a___a___a___a___a__ORF RF[3] ___a___a___a___a___a___a___a___>

170         180         190         200         210
            *           *           *           *           *
TGT TGC TTC TCC AGT TCC CTC ATC TTT ATT GGA GAG CCG CAG GAT TGG ATG TGT
ACA ACG AAG AGG TCA AGG GAG TAG AAA TAA CCT CTC GGC GTC CTA ACC TAC ACA
Cys Cys Phe Ser Ser Ser Leu Ile Phe Ile Gly Glu Pro Gln Asp Trp Met Cys>
___a___a___a___a___a___a___a__ORF RF[3] ___a___a___a___a___a___a___a___>

220         230         240         250         260
            *           *           *           *           *
CGT TTA CGC CAA CCT GCC TTT GGG ATC AGT TTT GTT CTC TGT ATC TCC TGC ATC
GCA AAT GCG GTT GGA CGG AAA CCC TAG TCA AAA CAA GAG ACA TAG AGG ACG TAG
Arg Leu Arg Gln Pro Ala Phe Gly Ile Ser Phe Val Leu Cys Ile Ser Cys Ile>
___a___a___a___a___a___a___a__ORF RF[3] ___a___a___a___a___a___a___a___>

270         280         290         300         310         320
     *           *           *           *           *           *
CTT GTG AAA ACT AAT AGA GTA CTC TTA GTA TTT GAA GCC AAG ATC CCC ACA AGT
GAA CAC TTT TGA TTA TCT CAT GAG AAT CAT AAA CTT CGG TTC TAG GGG TGT TCA
Leu Val Lys Thr Asn Arg Val Leu Leu Val Phe Glu Ala Lys Ile Pro Thr Ser>
___a___a___a___a___a___a___a__ORF RF[3] ___a___a___a___a___a___a___a___>

330         340         350         360         370
            *           *           *           *           *
CTC CAT CGT AAA TGG TGG GGG TTA AAC CTT CAG TTT TTG CTG GTG TTT CTG TGC
GAG GTA GCA TTT ACC ACC CCC AAT TTG GAA GTC AAA AAC GAC CAC AAA GAC ACG
Leu His Arg Lys Trp Trp Gly Leu Asn Leu Gln Phe Leu Leu Val Phe Leu Cys>
___a___a___a___a___a___a___a__ORF RF[3] ___a___a___a___a___a___a___a___>

380         390         400         410         420         430
            *           *           *           *           *           *
ACA TTT GTC CAA GTC ATG ATC TGT GTT GTC TGG CTG TAC AAT GCC CCT CCC TCC
TGT AAA CAG GTT CAG TAC TAG ACA CAA CAG ACC GAC ATG TTA CGG GGA GGG AGG
Thr Phe Val Gln Val Met Ile Cys Val Val Trp Leu Tyr Asn Ala Pro Pro Ser>
___a___a___a___a___a___a___a__ORF RF[3] ___a___a___a___a___a___a___a___>

440         450         460         470
            *           *           *           *
AGT TAC AGG AAT TAT GAC ATA GAT GAG ATG ATT TTT ATC ACA TG
TCA ATG TCC TTA ATA CTG TAT CTA CTC TAC TAA AAA TAG TGT AC
Ser Tyr Arg Asn Tyr Asp Ile Asp Glu Met Ile Phe Ile Thr>
___a___a___a___a___a___a__ORF RF[3] ___a___a___a___a___a___>
```

FIG. 27

Polynucleotide SEQ ID NO: 11;  Polypeptide SEQ ID NO: 12

```
  a cgc cca ggg att gaa aaa ttt gag aag gag atg gag gag cga gac atc   49
    Arg Pro Gly Ile Glu Lys Phe Glu Lys Glu Met Glu Glu Arg Asp Ile
     1               5                  10                  15 tgc att cac ctt aat gaa ctt atc tct cag tat ttt gag gay cat gaa     97
Cys Ile His Leu Asn Glu Leu Ile Ser Gln Tyr Phe Glu Asp His Glu
            20                  25                  30 atc caa gcg ctg gct gac agg att gag aac tcc aca gct aaa gtc atc    145
Ile Gln Ala Leu Ala Asp Arg Ile Glu Asn Ser Thr Ala Lys Val Ile
        35                  40                  45 gta gtg ttt gcc agc ggc cca gat atc gag cct tta atc aaa gag atg    193
Val Val Phe Ala Ser Gly Pro Asp Ile Glu Pro Leu Ile Lys Glu Met
    50                  55                  60 gtg agg aga aac atc aca gac cgt atc tgg tta gcc agt gaa gcg tgg    241
Val Arg Arg Asn Ile Thr Asp Arg Ile Trp Leu Ala Ser Glu Ala Trp
65                  70                  75                  80 gct agc tcc tct ctt ata gct aaa cca gag tat ctt gat gtt gtg gct    289
Ala Ser Ser Ser Leu Ile Ala Lys Pro Glu Tyr Leu Asp Val Val Ala
                85                  90                  95 ggg act atc ggc ttt gct ctc aag gca ggg cat att cct ggc tta aga    337
Gly Thr Ile Gly Phe Ala Leu Lys Ala Gly His Ile Pro Gly Leu Arg
            100                 105                 110 gag ttc cta cag caa gtg caa cca aag aga gac agt cat aat gaa ttt    385
Glu Phe Leu Gln Gln Val Gln Pro Lys Arg Asp Ser His Asn Glu Phe
        115                 120                 125 gtc agg gag ttt tgg gaa gaa acc ttc aac tgt tat ctg gaa gac agc    433
Val Arg Glu Phe Trp Glu Glu Thr Phe Asn Cys Tyr Leu Glu Asp Ser
    130                 135                 140 cag aga cag cag gaa agt gag aat ggc agc aca agt ttc agg cct ttg    481
Gln Arg Gln Gln Glu Ser Glu Asn Gly Ser Thr Ser Phe Arg Pro Leu
145                 150                 155                 160 tgt act ggt gag gaa gac atc aca agt gtt gag acc ccg tac ttg gac    529
Cys Thr Gly Glu Glu Asp Ile Thr Ser Val Glu Thr Pro Tyr Leu Asp
                165                 170                 175 tac aca cac ttt cgt atc tcc tat aac gtg tat gtt gca gtt tat tcc    577
Tyr Thr His Phe Arg Ile Ser Tyr Asn Val Tyr Val Ala Val Tyr Ser
            180                 185                 190 att gca cag gcc ctg cag gac ata ctc acc tgc aca cct gga cat gga    625
Ile Ala Gln Ala Leu Gln Asp Ile Leu Thr Cys Thr Pro Gly His Gly
        195                 200                 205 ctc ttt gcc aac aat tcc tgt gcc gat ata aag aaa atg gaa gca tgg    673
Leu Phe Ala Asn Asn Ser Cys Ala Asp Ile Lys Lys Met Glu Ala Trp
    210                 215                 220
```

FIG. 28A

Polynucleotide SEQ ID NO: 11; Polypeptide SEQ ID NO: 12 (CONTINUED)

```
cag gcc ctg aag cag ctt aga cat ttg aac tac acc aac agc atg ggg    721
Gln Ala Leu Lys Gln Leu Arg His Leu Asn Tyr Thr Asn Ser Met Gly
225             230             235             240 gaa aag atg cac ttt gat gag aac tca gac atg gca tca aac tac acc    769
Glu Lys Met His Phe Asp Glu Asn Ser Asp Met Ala Ser Asn Tyr Thr
                245             250             255 att ata aac tgg cac cgg tct gct gag gat ggc tct gtg gtg ttt gag    817
Ile Ile Asn Trp His Arg Ser Ala Glu Asp Gly Ser Val Val Phe Glu
            260             265             270 gac gtg gga tac tac agc atg cac gtc aag aga gga gcc aaa ctg ttc    865
Asp Val Gly Tyr Tyr Ser Met His Val Lys Arg Gly Ala Lys Leu Phe
        275             280             285 att gac aag aca aag att ttg tgg aat gga tac agt tcg gag gcg cca    913
Ile Asp Lys Thr Lys Ile Leu Trp Asn Gly Tyr Ser Ser Glu Ala Pro
    290             295             300 ttc tct aat tgc agt gag gac tgt gaa cct ggt aca agg aag ggg atc    961
Phe Ser Asn Cys Ser Glu Asp Cys Glu Pro Gly Thr Arg Lys Gly Ile
305             310             315             320 att gac agt atg ccc aca tgt tgc ttt gaa tgc act gag tgc tca gat    1009
Ile Asp Ser Met Pro Thr Cys Cys Phe Glu Cys Thr Glu Cys Ser Asp
                325             330             335 gga gag tac agt aat cat aaa gat gcc agt gtt tgc acc aag tgt cca    1057
Gly Glu Tyr Ser Asn His Lys Asp Ala Ser Val Cys Thr Lys Cys Pro
            340             345             350 tat aac tct tgg tcc aat ggg aat cac aca ttc tgc ttc ctg aag gaa    1105
Tyr Asn Ser Trp Ser Asn Gly Asn His Thr Phe Cys Phe Leu Lys Glu
        355             360             365 atc gag ttt ctc tcc tgg aca gaa cca ttc ggg atc gct ttg gcc ata    1153
Ile Glu Phe Leu Ser Trp Thr Glu Pro Phe Gly Ile Ala Leu Ala Ile
    370             375             380 tgt gca gta ctg ggt gtc ctc ttg aca gct ttt gtg atc gga gtc ttt    1201
Cys Ala Val Leu Gly Val Leu Leu Thr Ala Phe Val Ile Gly Val Phe
385             390             395             400 gtc aga ttc cgc aac acc cca ata gtg aag gcc aca aac cga gaa ctg    1249
Val Arg Phe Arg Asn Thr Pro Ile Val Lys Ala Thr Asn Arg Glu Leu
                405             410             415 tcc tac gtt ctc ctg twc tca ctt atc tgt tgc ttc tca agc tcc ctc    1297
Ser Tyr Val Leu Leu Xaa Ser Leu Ile Cys Cys Phe Ser Ser Ser Leu
            420             425             430 akc ttc atc gg                                                      1308
Xaa Phe Ile
435
```

FIG. 28B

Polypeptide SEQ ID NO: 12

```
Arg Pro Gly Ile Glu Lys Phe Glu Lys Glu Met Glu Glu Arg Asp Ile
 1               5                  10                  15
Cys Ile His Leu Asn Glu Leu Ile Ser Gln Tyr Phe Glu Asp His Glu
                 20                  25                  30
Ile Gln Ala Leu Ala Asp Arg Ile Glu Asn Ser Thr Ala Lys Val Ile
             35                  40                  45
Val Val Phe Ala Ser Gly Pro Asp Ile Glu Pro Leu Ile Lys Glu Met
 50                  55                  60
Val Arg Arg Asn Ile Thr Asp Arg Ile Trp Leu Ala Ser Glu Ala Trp
 65                  70                  75                  80
Ala Ser Ser Ser Leu Ile Ala Lys Pro Glu Tyr Leu Asp Val Val Ala
                 85                  90                  95
Gly Thr Ile Gly Phe Ala Leu Lys Ala Gly His Ile Pro Gly Leu Arg
                100                 105                 110
Glu Phe Leu Gln Gln Val Gln Pro Lys Arg Asp Ser His Asn Glu Phe
             115                 120                 125
Val Arg Glu Phe Trp Glu Glu Thr Phe Asn Cys Tyr Leu Glu Asp Ser
130                 135                 140
Gln Arg Gln Gln Glu Ser Glu Asn Gly Ser Thr Ser Phe Arg Pro Leu
145                 150                 155                 160
Cys Thr Gly Glu Glu Asp Ile Thr Ser Val Glu Thr Pro Tyr Leu Asp
                165                 170                 175
Tyr Thr His Phe Arg Ile Ser Tyr Asn Val Tyr Val Ala Val Tyr Ser
             180                 185                 190
Ile Ala Gln Ala Leu Gln Asp Ile Leu Thr Cys Thr Pro Gly His Gly
         195                 200                 205
Leu Phe Ala Asn Asn Ser Cys Ala Asp Ile Lys Lys Met Glu Ala Trp
     210                 215                 220
Gln Ala Leu Lys Gln Leu Arg His Leu Asn Tyr Thr Asn Ser Met Gly
225                 230                 235                 240
Glu Lys Met His Phe Asp Glu Asn Ser Asp Met Ala Ser Asn Tyr Thr
                245                 250                 255
Ile Ile Asn Trp His Arg Ser Ala Glu Asp Gly Ser Val Val Phe Glu
                260                 265                 270
Asp Val Gly Tyr Tyr Ser Met His Val Lys Arg Gly Ala Lys Leu Phe
             275                 280                 285
Ile Asp Lys Thr Lys Ile Leu Trp Asn Gly Tyr Ser Ser Glu Ala Pro
290                 295                 300
Phe Ser Asn Cys Ser Glu Asp Cys Glu Pro Gly Thr Arg Lys Gly Ile
305                 310                 315                 320
Ile Asp Ser Met Pro Thr Cys Cys Phe Glu Cys Thr Glu Cys Ser Asp
                325                 330                 335
Gly Glu Tyr Ser Asn His Lys Asp Ala Ser Val Cys Thr Lys Cys Pro
             340                 345                 350
Tyr Asn Ser Trp Ser Asn Gly Asn His Thr Phe Cys Phe Leu Lys Glu
         355                 360                 365
Ile Glu Phe Leu Ser Trp Thr Glu Pro Phe Gly Ile Ala Leu Ala Ile
     370                 375                 380
Cys Ala Val Leu Gly Val Leu Leu Thr Ala Phe Val Ile Gly Val Phe
385                 390                 395                 400
Val Arg Phe Arg Asn Thr Pro Ile Val Lys Ala Thr Asn Arg Glu Leu
                405                 410                 415
Ser Tyr Val Leu Leu Xaa Ser Leu Ile Cys Cys Phe Ser Ser Ser Leu
             420                 425                 430
Xaa Phe Ile
435
```

FIG. 29

Polynucleotide SEQ ID NO: 11; Polypeptide SEQ ID NO: 12

```
              10          20          30          40          50
              *           *           *           *           *
A  CGC CCA GGG ATT GAA AAA TTT GAG AAG GAG ATG GAG GAG CGA GAC ATC TGC
T  GCG GGT CCC TAA CTT TTT AAA CTC TTC CTC TAC CTC CTC GCT CTG TAG ACG
   Arg Pro Gly Ile Glu Lys Phe Glu Lys Glu Met Glu Glu Arg Asp Ile Cys>
   ___a___a___a___a___a___a____ORF RF[2] _a___a___a___a___a___a____a___>

60          70          80          90         100
              *           *           *           *           *
ATT CAC CTT AAT GAA CTT ATC TCT CAG TAT TTT GAG GAY CAT GAA ATC CAA GCG
TAA GTG GAA TTA CTT GAA TAG AGA GTC ATA AAA CTC CTR GTA CTT TAG GTT CGC
Ile His Leu Asn Glu Leu Ile Ser Gln Tyr Phe Glu Asp His Glu Ile Gln Ala>
___a___a___a___a___a___a__ORF RF[2] ___a___a___a___a___a___a___a___>

110         120         130         140         150         160
              *           *           *           *           *           *
CTG GCT GAC AGG ATT GAG AAC TCC ACA GCT AAA GTC ATC GTA GTG TTT GCC AGC
GAC CGA CTG TCC TAA CTC TTG AGG TGT CGA TTT CAG TAG CAT CAC AAA CGG TCG
Leu Ala Asp Arg Ile Glu Asn Ser Thr Ala Lys Val Ile Val Val Phe Ala Ser>
___a___a___a___a___a___a___a__ORF RF[2] ___a___a___a___a___a___a___a___>

170         180         190         200         210
              *           *           *           *           *
GGC CCA GAT ATC GAG CCT TTA ATC AAA GAG ATG GTG AGG AGA AAC ATC ACA GAC
CCG GGT CTA TAG CTC GGA AAT TAG TTT CTC TAC CAC TCC TCT TTG TAG TGT CTG
Gly Pro Asp Ile Glu Pro Leu Ile Lys Glu Met Val Arg Arg Asn Ile Thr Asp>
___a___a___a___a___a___a___a__ORF RF[2] ___a___a___a___a___a___a___a___>

220         230         240         250         260
              *           *           *           *           *
CGT ATC TGG TTA GCC AGT GAA GCG TGG GCT AGC TCC TCT CTT ATA GCT AAA CCA
GCA TAG ACC AAT CGG TCA CTT CGC ACC CGA TCG AGG AGA GAA TAT CGA TTT GGT
Arg Ile Trp Leu Ala Ser Glu Ala Trp Ala Ser Ser Ser Leu Ile Ala Lys Pro>
___a___a___a___a___a___a___a__ORF RF[2] ___a___a___a___a___a___a___a___>

270         280         290         300         310         320
              *           *           *           *           *           *
GAG TAT CTT GAT GTT GTG GCT GGG ACT ATC GGC TTT GCT CTC AAG GCA GGG CAT
CTC ATA GAA CTA CAA CAC CGA CCC TGA TAG CCG AAA CGA GAG TTC CGT CCC GTA
Glu Tyr Leu Asp Val Val Ala Gly Thr Ile Gly Phe Ala Leu Lys Ala Gly His>
___a___a___a___a___a___a___a__ORF RF[2] ___a___a___a___a___a___a___a___>

330         340         350         360         370
              *           *           *           *           *
ATT CCT GGC TTA AGA GAG TTC CTA CAG CAA GTG CAA CCA AAG AGA GAC AGT CAT
TAA GGA CCG AAT TCT CTC AAG GAT GTC GTT CAC GTT GGT TTC TCT CTG TCA GTA
Ile Pro Gly Leu Arg Glu Phe Leu Gln Gln Val Gln Pro Lys Arg Asp Ser His>
___a___a___a___a___a___a___a__ORF RF[2] ___a___a___a___a___a___a___a___>

380         390         400         410         420         430
              *           *           *           *           *           *
AAT GAA TTT GTC AGG GAG TTT TGG GAA GAA ACC TTC AAC TGT TAT CTG GAA GAC
TTA CTT AAA CAG TCC CTC AAA ACC CTT CTT TGG AAG TTG ACA ATA GAC CTT CTG
Asn Glu Phe Val Arg Glu Phe Trp Glu Glu Thr Phe Asn Cys Tyr Leu Glu Asp>
___a___a___a___a___a___a___a__ORF RF[2] ___a___a___a___a___a___a___a___>

440         450         460         470         480
              *           *           *           *           *
AGC CAG AGA CAG CAG GAA AGT GAG AAT GGC AGC ACA AGT TTC AGG CCT TTG TGT
TCG GTC TCT GTC GTC CTT TCA CTC TTA CCG TCG TGT TCA AAG TCC GGA AAC ACA
Ser Gln Arg Gln Gln Glu Ser Glu Asn Gly Ser Thr Ser Phe Arg Pro Leu Cys>
___a___a___a___a___a___a___a__ORF RF[2] ___a___a___a___a___a___a___a___>
```

FIG. 30A

Polynucleotide SEQ ID NO: 11; Polypeptide SEQ ID NO: 12 (CONTINUED)

```
         490         500         510         520         530
          *           *           *           *           *
ACT GGT GAG GAA GAC ATC ACA AGT GTT GAG ACC CCG TAC TTG GAC TAC ACA CAC
TGA CCA CTC CTT CTG TAG TGT TCA CAA CTC TGG GGC ATG AAC CTG ATG TGT GTG
Thr Gly Glu Glu Asp Ile Thr Ser Val Glu Thr Pro Tyr Leu Asp Tyr Thr His>
___a___a___a___a___a___a___a__ORF RF[2] ___a___a___a___a___a___a___a___>

540         550         560         570         580         590
   *           *           *           *           *           *
TTT CGT ATC TCC TAT AAC GTG TAT GTT GCA GTT TAT TCC ATT GCA CAG GCC CTG
AAA GCA TAG AGG ATA TTG CAC ATA CAA CGT CAA ATA AGG TAA CGT GTC CGG GAC
Phe Arg Ile Ser Tyr Asn Val Tyr Val Ala Val Tyr Ser Ile Ala Gln Ala Leu>
___a___a___a___a___a___a___a__ORF RF[2] ___a___a___a___a___a___a___a___>

600         610         620         630         640
          *           *           *           *           *
CAG GAC ATA CTC ACC TGC ACA CCT GGA CAT GGA CTC TTT GCC AAC AAT TCC TGT
GTC CTG TAT GAG TGG ACG TGT GGA CCT GTA CCT GAG AAA CGG TTG TTA AGG ACA
Gln Asp Ile Leu Thr Cys Thr Pro Gly His Gly Leu Phe Ala Asn Asn Ser Cys>
___a___a___a___a___a___a___a__ORF RF[2] ___a___a___a___a___a___a___a___>

650         660         670         680         690         700
      *           *           *           *           *           *
GCC GAT ATA AAG AAA ATG GAA GCA TGG CAG GCC CTG AAG CAG CTT AGA CAT TTG
CGG CTA TAT TTC TTT TAC CTT CGT ACC GTC CGG GAC TTC GTC GAA TCT GTA AAC
Ala Asp Ile Lys Lys Met Glu Ala Trp Gln Ala Leu Lys Gln Leu Arg His Leu>
___a___a___a___a___a___a___a__ORF RF[2] ___a___a___a___a___a___a___a___>

710         720         730         740         750
          *           *           *           *           *
AAC TAC ACC AAC AGC ATG GGG GAA AAG ATG CAC TTT GAT GAG AAC TCA GAC ATG
TTG ATG TGG TTG TCG TAC CCC CTT TTC TAC GTG AAA CTA CTC TTG AGT CTG TAC
Asn Tyr Thr Asn Ser Met Gly Glu Lys Met His Phe Asp Glu Asn Ser Asp Met>
___a___a___a___a___a___a___a__ORF RF[2] ___a___a___a___a___a___a___a___>

760         770         780         790         800
          *           *           *           *           *
GCA TCA AAC TAC ACC ATT ATA AAC TGG CAC CGG TCT GCT CAG GAT GGC TCT GTG
CGT AGT TTG ATG TGG TAA TAT TTG ACC GTG GCC AGA CGA CTC CTA CCG AGA CAC
Ala Ser Asn Tyr Thr Ile Ile Asn Trp His Arg Ser Ala Gln Asp Gly Ser Val>
___a___a___a___a___a___a___a__ORF RF[2] ___a___a___a___a___a___a___a___>

810         820         830         840         850         860
   *           *           *           *           *           *
GTG TTT GAG GAC GTG GGA TAC TAC AGC ATG CAC GTC AAG AGA GGA GCC AAA CTG
CAC AAA CTC CTG CAC CCT ATG ATG TCG TAC GTG CAG TTC TCT CCT CGG TTT GAC
Val Phe Glu Asp Val Gly Tyr Tyr Ser Met His Val Lys Arg Gly Ala Lys Leu>
___a___a___a___a___a___a___a__ORF RF[2] ___a___a___a___a___a___a___a___>

870         880         890         900         910
          *           *           *           *           *
TTC ATT GAC AAG ACA AAG ATT TTG TGG AAT GGA TAC AGT TCG GAG GCG CCA TTC
AAG TAA CTG TTC TGT TTC TAA AAC ACC TTA CCT ATG TCA AGC CTC CGC GGT AAG
Phe Ile Asp Lys Thr Lys Ile Leu Trp Asn Gly Tyr Ser Ser Glu Ala Pro Phe>
___a___a___a___a___a___a___a__ORF RF[2] ___a___a___a___a___a___a___a___>

920         930         940         950         960         970
    *           *           *           *           *           *
TCT AAT TGC AGT GAG GAC TGT GAA CCT GGT ACA AGG AAG GGG ATC ATT GAC AGT
AGA TTA ACG TCA CTC CTG ACA CTT GGA CCA TGT TCC TTC CCC TAG TAA CTG TCA
Ser Asn Cys Ser Glu Asp Cys Glu Pro Gly Thr Arg Lys Gly Ile Ile Asp Ser>
___a___a___a___a___a___a___a__ORF RF[2] ___a___a___a___a___a___a___a___>
```

FIG. 30B

Polynucleotide SEQ ID NO: 11; Polypeptide SEQ ID NO: 12 (CONTINUED)

```
          980           990          1000          1010          1020
           *             *             *             *             *
    ATG CCC ACA TGT TGC TTT GAA TGC ACT GAG TGC TCA GAT GGA GAG TAC AGT AAT
    TAC GGG TGT ACA ACG AAA CTT ACG TGA CTC ACG AGT CTA CCT CTC ATG TCA TTA
    Met Pro Thr Cys Cys Phe Glu Cys Thr Glu Cys Ser Asp Gly Glu Tyr Ser Asn>
    ___a___a___a___a___a___a___a__ORF RF[2] ___a___a___a___a___a___a___a___>

1030          1040          1050          1060          1070
           *             *             *             *             *
    CAT AAA GAT GCC AGT GTT TGC ACC AAG TGT CCA TAT AAC TCT TGG TCC AAT GGG
    GTA TTT CTA CGG TCA CAA ACG TGG TTC ACA GGT ATA TTG AGA ACC AGG TTA CCC
    His Lys Asp Ala Ser Val Cys Thr Lys Cys Pro Tyr Asn Ser Trp Ser Asn Gly>
    ___a___a___a___a___a___a___a__ORF RF[2] ___a___a___a___a___a___a___a___>

1080          1090          1100          1110          1120          1130
    *             *             *             *             *             *
AAT CAC ACA TTC TGC TTC CTG AAG GAA ATC GAG TTT CTC TCC TGG ACA GAA CCA
TTA GTG TGT AAG ACG AAG GAC TTC CTT TAG CTC AAA GAG AGG ACC TGT CTT GGT
Asn His Thr Phe Cys Phe Leu Lys Glu Ile Glu Phe Leu Ser Trp Thr Glu Pro>
___a___a___a___a___a___a___a__ORF RF[2] ___a___a___a___a___a___a___a___>

1140          1150          1160          1170          1180
           *             *             *             *             *
    TTC GGG ATA GCT TTG GCC ATA TGT GCA GTA CTG GGT GTG CTC TTG ACA GCT TTT
    AAG CCC TAT CGA AAC CGG TAT ACA CGT CAT GAC CCA CAC GAG AAC TGT CGA AAA
    Phe Gly Ile Ala Leu Ala Ile Cys Ala Val Leu Gly Val Leu Leu Thr Ala Phe>
    ___a___a___a___a___a___a___a__ORF RF[2] ___a___a___a___a___a___a___a___>

1190          1200          1210          1220          1230          1240
           *             *             *             *             *             *
    GTG ATC GGA GTC TTT GTC AGA TTC CGC AAC ACC CCA ATA GTG AAG GCC ACA AAC
    CAC TAG CCT CAG AAA CAG TCT AAG GCG TTG TGG GGT TAT CAC TTC CGG TGT TTG
    Val Ile Gly Val Phe Val Arg Phe Arg Asn Thr Pro Ile Val Lys Ala Thr Asn>
    ___a___a___a___a___a___a___a__ORF RF[2] ___a___a___a___a___a___a___a___>

1250          1260          1270          1280          1290
                *             *             *             *             *
         CGA GAA CTG TCC TAC GTT CTC CTG TWC TCA CTT ATC TGT TGC TTC TCA AGC TCC
         GCT CTT GAC AGG ATG CAA GAG GAC AWG AGT GAA TAG ACA ACG AAG AGT TCG AGG
         Arg Glu Leu Ser Tyr Val Leu Leu Xxx Ser Leu Ile Cys Cys Phe Ser Ser Ser>
         ___a___a___a___a___a___a___a__ORF RF[2] ___a___a___a___a___a___a___a___>

1300
      *
CTC AKC TTC ATC GG
GAG TMG AAG TAG CC
Leu Xxx Phe Ile>
____ORF RF[____>
```

FIG. 30C

… # POLYCATION-SENSING RECEPTOR IN AQUATIC SPECIES AND METHODS OF USE THEREOF

RELATED APPLICATIONS

This application is a Divisional of U.S. application Ser. No.: 09/715,538, filed on Nov. 17, 2000, abandoned Jun. 26, 2003, entitled, "Polycation-Sensing Receptor in Aquatic Species and Methods of Use Thereof," by H. William Harris, et al., which is a Divisional of U.S. application Ser. No.: 09/162,021, filed on Sep. 28, 1998, now U.S. Pat. No. 6,337,391, issued Jan. 8, 2002, entitled, "Polycation-Sensing Receptor in Aquatic Species and Methods of Use Thereof" by H. William Harris, et al., which is a continuation-in-part of International PCT application No. PCT/US97/05031, entitled "Polycation-Sensing Receptor in Aquatic Species and Methods of Use Thereof", by H. William Harris, et al., filed on Mar. 27, 1997, which is a continuation-in-part of application Ser. No. 08/622,738, abandoned Jul. 1, 2002, entitled "Polycation-Sensing Receptor in Fish and Methods of Use Thereof", by H. William Harris, et al., filed Mar. 27, 1996, the teachings of which are hereby incorporated herein by reference in their entirety.

GOVERMAENT SUPPORT

This invention was made with Government support under Contract No. R01 DK38874 awarded by the National Institutes of Health. The Government has certain rights in the invention.

BACKGROUND OF THE INVENTION

It is well recognized that a stagnation or decline in production of edible seafood, in particular, fish, by the marine fishing industry has occurred on a world wide basis. Since the world's population increases by approximately 100 million each year, maintenance of the present caloric content of the average diet will require production of an additional 19 million metric tons of seafood per year (United Nations Food and Agriculture Organization, The State of the World Fisheries and Aquaculture, Rome, Italy (1995)). In addition, fish products are becoming increasingly utilized in ways other than just food, for example, production of shells and pearls. To achieve this level of production, aquaculture (the cultivation of marine species) will have to double its production in the next 15 years, and wild populations of marine species must be restored.

Aquatic species includes marine teleost and elasmobranch fishes, fresh water teleost fish, euryhaline fish crustations, molusks and echinoderms. Marine teleost fish live in sea water with a high osmolality of about 1,000 mosm. Fresh-water teleost fish normally live in water of less than 50 mosm. Euryhaline fish have the ability to acclimate to either of these environments. Ionic composition and osmolality of fish body fluids are maintained in these vastly different environments through gill, kidney and gastrointestinal tract epithelial cell function.

A major problem in aquaculture is development of methodology to rear marine teleost fish, such as cod, flounder and halibut, under freshwater hatchery conditions. To date, factors critical to the acclimation and survival of marine species to fresh water environments, and the control of these factors, have not been fully elucidated.

Attempts to develop such methodologies have also been complicated by problems with feeding the maturing larval forms of these fish. Development of cod, halibut or flounder species that could be reared in fresh water would be of great potential benefit in this regard. Under controlled fresh water conditions, developing forms of these fish could be raised in the absence of bacterial contamination normally present in seawater, and utilize new fresh water food sources that would potentially improve their survival.

The aquaculture industry utilizes the ability of young fish, e.g., salmon, (also called par) to be raised initially in fresh water and subsequently to be transferred for "growth out" in salt water pens as a means to produce large numbers of adult fish (young salmon tolerant to seawater are called smolt). Improvements in both the survival and health of fish undergoing the par-smolt transition would be very valuable for aquaculture growers.

Moreover, salmon that are kept in coastal marine "grow-out" pens during the winter are constantly at risk, since both winter storms, as well as exposure to extremely cold seawater, causes fish to freeze and die. These risks are further complicated by the fact that when adult salmon are adapted to salt water they do not readily readapt back to fresh water environment. Hence, lack of understanding of the means to readapt adult salmon from salt to fresh water results in the loss of salmon.

It is apparent, therefore, that there is an immediate need to develop methods of augmenting the survival of fish in fresh water and sea water, both in a natural environment and an aquacultural environment.

SUMMARY OF THE INVENTION

The present invention relates to the identification and characterization of a PolyValent Cation-sensing Receptor protein (also referred to herein as the Aquatic polyvalent cation-sensing receptor, Aquatic PVCR, or PVCR) which is present in various tissues of marine species. As defined herein, aquatic species includes various fish (e.g., elasmobranch fish, such as sharks, skates; teleost fish, such as summer and winter flounder, salmon, cod, halibut, lumpfish and trout), crustaceans (e.g., lobster, crab and shrimp), mollusks (e.g., clams, mussels and oysters), lamprey and swordfish.

As described herein, for the first time, a polyvalent cation-sensing receptor protein has been identified in aquatic species, located on the plasma membranes of cells in the gastrointestinal tract, kidney, ovary, lung, brain and heart, and in fish brain, gill, heart, intestines, urinary bladder, rectal gland, kidney tubules, and olfactory lamellae. The widespread distribution of Aquatic PVCR protein on the plasma membranes of epithelial cells, as well as in the brain, indicates the involvement of Aquatic PVCR in modulation of epithelial ion and water transport and endocrine function. Data presented herein demonstrate that the Aquatic PVCR plays a critical role in the acclimation of fish to environments of various salinities. The Aquatic polyvalent cation-sensing receptor allows the successful adaptation of fish, such as flounder, to marine and fresh water environments.

One embodiment of the present invention encompasses Aquatic PVCR proteins expressed in tissues of marine species. Aquatic PVCR proteins have been identified as being present in selected epithelial cells in marine, fresh water and euryhaline fish kidney, intestine, gill, urinary bladder, brain, and olfactory tissue. More specifically, the Aquatic PVCR protein has been identified on the plasma membranes of epithelial cells of fish kidney tubules, especially in the collecting duct (CD), late distal tubule (LDT) and the olfactory lamellae. The present invention is intended to encompass these Aquatic PVCR proteins, their amino acid sequences, and nucleic acid sequences, (DNA or RNA) that encode these Aquatic PVCR proteins. In particular, the claimed invention embodies the amino acid and nucleic acid sequences of PVCRs in dogfish shark, winter and summer flounder, and lumpfish.

In another embodiment of the present invention, methods for regulating salinity tolerance in fish are encompassed. Data presented herein indicate that the Aquatic PVCR is a "master switch" for both endocrine and kidney regulation of adult fish kidney and intestinal ion and water transport, as well as key developmental processes within the fish embryo. Modulating the expression of the Aquatic polyvalent cation-sensing receptor will activate or inhibit Aquatic PVCR mediated ion transport and endocrine changes that permit fish to adapt to fresh or salt water. Also, increasing or deceasing salinity tolerance in aquatic species can refer to activating the PVCR in the epithelial cells.

For example, methods are provided to increase the salinity tolerance of fish adapted to fresh water environment by activation of the Aquatic PVCR in selected epithelial cells. Methods are also provided to decrease the salinity tolerance of fish adapted to a salt water environment by inhibiting the activity of the Aquatic PVCR in selected epithelial cells. Also, regulation of salinity tolerance, via regulating the activation/inhibition of the Aquatic PVCR, occurs by modulating the ion concentration in the surrounding environment. Such modulation can be done by changing the ion concentration of magnesium, calcium and/or sodium.

In another embodiment of the present invention, methods are provided to identify a substance capable of regulating ionic composition of fish fluids, (e.g., salinity tolerance in fish), and endocrine function, by determining the effect that the substance has on the activation or inhibition of the Aquatic PVCR. As described herein, the nucleic acid sequence encoding an Aquatic PVCR has been determined and recombinant PVCR proteins can be expressed in e.g., oocytes of the frog, *Xenopus laevis*. The oocyte assay system permits the screening of a large library of compounds that will either activate or inhibit Aquatic PVCR function. Candidate compounds can be further screened in e.g., an in vitro assay system using isolated flounder bladder preparations to measure transepithelial transport of ions important for salinity adaption.

As a result of the work described herein, Aquatic PVCR proteins have been identified and their role in maintaining osmoregulation has been characterized. As a further result of the work described herein, methods are now available to modulate the activation of the Aquatic PVCR, resulting in methods to regulate salinity tolerance in marine and fresh water species of fish and thus, facilitate aquaculture of marine fish. Methods of regulating salinity tolerance also provides the means to develop new species of marine fish that are easily adaptable to fresh water aquaculture. Successful development of new species of marine fish would permit these species to be raised initially in protected fresh water hatcheries and later transferred to marine conditions.

The claimed methods also pertain to method for altering body composition (e.g., tissue composition, or meat/muscle composition) comprising modulating the salinity (e.g., ion concentration) of the surrounding environment. Aspects of body composition that are altered include, but are not limited to: fat content, protein content, weight, thickness, moisture, and taste. For example, the thickness of a filet of fish can be increased by the methods described herein. The altering of body composition occurs by maintaining the aquatic species in low and/or high salinity/ion concentrations.

The claimed methods also related to methods for reducing or essentially eliminating or ridding the fish of parasites, bacteria, and contaminants. Maintaining aquatic species in higher salinity than normal reduces parasites and/or bacteria while maintaining the species in lower salinity reduces contaminants (e.g., antibiotics, hydrocarbons, and/or amines). The species can be maintained in both environments, consecutively, to reduce parasites, bacteria and contaminants.

BRIEF DESCRIPTION OF THE DRAWINGS

FIGS. 2A–F are photographs of immunocytochemistry results showing the distribution of PVCR protein in various tissues of teleost fish including flounder (*Pseudopleuronectes americanus*), trout (*Onchorynchus nerka*) and killifish (*Fundulus heteroclitus*).

FIGS. 4A∝E depict the nucleotide sequence of Shark Kidney Calcium Receptor Related Protein-I (SKCaR-RP-I or SKCaR-I) (SEQ ID NO: 1) with the ORF starting at nt 439 and ending at 3516.

FIGS. 5A–E depict the annotated nucleotide sequence (SEQ ID NO: 1) and the deduced amino acids sequence (SEQ ID NO: 2) of the Shark Kidney Calcium Receptor Related Protein-I (SKCaR-RP-I).

FIGS. 16A–B are the nucleic acid sequence (cDNA) of a dogfish Shark Calcium Receptor Related Protein-IIa (SKCaR-IIa) (SEQ ID NO: 3).

FIG. 17 is the amino acid sequence of a dogfish Shark Calcium Receptor Related Protein-IIa (SKCaR-IIa) (SEQ ID NO:4).

FIGS. 18A–B is the annotated nucleic (SEQ ID NO: 3) and amino acid sequence (SEQ ID NO:4) for a dogfish Shark Calcium Receptor Related Protein-IIa (SKCaR-IIa).

FIG. 19 is the nucleic acid sequence (cDNA) of a dogfish Shark Calcium Receptor Related Protein-IIb (SKCaR-IIb) (SEQ ID NO: 5).

FIG. 20 is the amino acid sequence of a dogfish Shark Calcium Receptor Related Protein-IIb (SKCaR-IIb) (SEQ ID NO:6).

FIGS. 21A–B is the annotated nucleic (SEQ ID NO: 5) and amino acid sequence (SEQ ID NO:6) for a dogfish Shark Calcium Receptor Related Protein-IIb (SKCaR-IIb).

FIG. 22 is the nucleic acid sequence (cDNA) of a winter flounder (SEQ ID NO: 7) Aquatic PVCR.

FIG. 23 is the amino acid sequence of a winter flounder (SEQ ID NO:8) Aquatic PVCR.

FIGS. 24A–B is the annotated nucleic (SEQ ID NO: 7) and amino acid sequence (SEQ ID NO:8) for a winter flounder Aquatic PVCR.

FIG. 25 is the nucleic acid sequence (cDNA) of a summer flounder (SEQ ID NO: 9) Aquatic PVCR.

FIG. 26 is the amino acid sequence of a summer flounder (SEQ ID NO: 10) Aquatic PVCR.

FIG. 27 is the annotated nucleic (SEQ ID NO: 7) and amino acid sequence (SEQ ID NO:8) for a summer flounder Aquatic PVCR.

FIGS. 28A–B are the nucleic acid sequence (cDNA) of a lumpfish (SEQ ID NO: 11) Aquatic PVCR.

FIG. 29 is the amino acid sequence of a lumpfish (SEQ ID NO: 12) Aquatic PVCR.

FIGS. 30A–C is the annotated nucleic (SEQ ID NO: 11) and amino acid sequence (SEQ ID NO: 12) for lumpfish Aquatic PVCR.

DETAILED DESCRIPTION

Figure 1A:
FIGS. 1A–F are photographs of immunocytochemistry results showing the distribution of PVCR protein in various tissues of elasmobranch fish, including dogfish shark (*Squalus acanthias*) and little skate (*Raja crinacca*).

Described herein, for the first time, are cell surface receptors, called polyvalent cation-sensing receptor proteins, which are present in selected epithelial cells in aquatic species tissue and organs, such as fish kidney, intestine, bladder, rectal gland, gill and brain. This Aquatic receptor protein is also referred to herein as the "Aquatic PVCR" or "PVCR." Evidence is also presented herein that the expression of Aquatic PVCR is modulated in aquatic species transferred from fresh to salt water. The combination of these data and knowledge of osmoregulation in fish, and other marine species, outlined briefly below, strongly suggest that Aquatic PVCR is the "master switch" for both endocrine and kidney regulation of marine species kidney, intestine ion and water transport. In addition, Aquatic PVCR function may control or strongly influence maturation and developmental stages in marine species.

In mammals, calcium receptor protein, or terrestial CaR proteins (also referred to herein as mammalian CaR) have been identified in various tissues in humans and rat. A mammalian CaR protein has been isolated and shown to be the cell surface receptor enabling mammalian parathyroid and calcitonin cells to respond to changes in extracellular $Ca^{2+}$. (Brown, E. M. et al., *New Eng. J. Med.*, 333:243, (1995)). Mammalian CaR is a membrane protein that is a member of the G-protein-coupled receptor family. When activated by external $Ca^{2+}$, PVCR modulates various intracellular signal transduction pathways and alters certain functions in selected cells including secretion of various hormones (PTH, calcitonin, ACTH and prolactin) by endocrine/brain cells and ion transport by epithelial cells.

Subsequent work has revealed that abundant CaR/PVCR is present in epithelial cells of the thick ascending limb (TAL) and distal convoluted tubules (DCT) of the mammalian kidney where it modulates transepithelial salt transport (Riccardi, D. J. et al., *Proc. Nat. Acad. Sci USA*, 92:131–135 (1995)). Recent research demonstrated that PVCR is present on the apical surface of epithelial cells of the mammalian kidney medullary collecting duct where it senses urinary $Ca^{2+}$ and adjusts vasopressin-mediated water reabsorption by the kidney (Sands, J. M. et al., *J. Clinical Investigation* 99:1399–1405 (Mar. 1997)). Lastly, PVCR is also present in various regions of the brain where it is involved in regulation of thirst and associated behavior (Brown, E. M. et al., *New England J. of Med.*, 333:234–240 (1995)).

Another protein important for osmoregulation in mammals is the NaCl cotransporter. The NaCl cotransporter is present in the DCT of human kidney where it absorbs NaCl and facilitates reabsorption of $Ca^{2+}$. A NaCl cotransporter protein has also been isolated from flounder urinary bladder (Gamba, G. et al., *Proc. Nat. Acad. Sci. (USA)*, 902749–2753 (1993)). Recently, it has been demonstrated that NaCl reabsorption mediated by this NaCl transporter in the DCT of humans is modulated by mammalian PVCR (Plotkin, M. et al. *J. Am. Soc. Nephrol.*, 6:349A (1995)).

As described herein, a PVCR protein has been identified in specific epithelial cells in tissues critical for ionic homeostasis in marine species. It is reasonable to believe that the Aquatic PVCR plays similar critical roles in biological functions in marine species, as the mammalian CaR in mammals.

Specifically, Aquatic PVCR proteins have been found in species of elasmobranchs and species of teleosts. Elasmobranchs are cartilaginous fish, such as sharks, rays and skates, and are predominately marine; teleosts, such as summer and winter flounder, cod, trout, killifish and salmon, can be freshwater, marine or euryhaline. The PVCR has also been isolated several other species including lumpfish, swordfish, and lamprey.

Marine teleost fish live in seawater possessing a high osmolality (1,000 mosm) that normally contains 10 millimolar (mM) $Ca^{2+}$, 50 mM $Mg^{2+}$ and 450 mM NaCl (Evans, D. H. Osmotic and Ionic Regulation, Chapter 11 in *The Physiology of Fishes*, CRC Press, Boca Raton, Fla. (1993)). Since their body fluids are 300–400 mosm, these fish are obligated to drink sea water, absorb salts through their intestine and secrete large quantities of NaCl through their gills and $Mg^{2+}$ and $Ca^{2+}$ through their kidneys. Their kidneys produce only small amounts of isotonic urine.

In contrast, fresh water teleost fish possess body fluids of 300 mosm and normally live in water of less than 50 mosm containing 5–20 mM NaCl and less than 1 mM $Ca^{2+}$ and $Mg^{2+}$. These fish drink little, but absorb large amounts of water from their dilute environment. As a result, their kidneys produce copious dilute urine to maintain water balance. Freshwater fish gill tissue has a low permeability to ions and gill epithelial cells extract NaCl from water (Evans, D. H., "Osmotic and Ionic Regulation", Chapter 11 in *The Physiology of Fishes*, CRC Press, Boca Raton, Fla. (1993)).

Euryhaline fish acclimate to various salinities by switching back and forth between these two basic patterns of ion and water transport. For example, when fresh water adapted teleost fish are challenged with high salinities, their gill epithelia rapidly alter net NaCl flux such that NaCl is secreted rather than reabsorbed (Zadunaisky, J. A. et al., *Bull. MDI Biol. Lab.*, 32:152–156 (1992)). Reduction of extracellular $Ca^{2+}$ from 10 mM to 100 micromolar profoundly inhibits this transport process (Zadunaisky, J. A. et al., *Bull. MDI Biol. Lab.*, 32:152–156 (1992)). In flounder species, transfer to seawater activates a series of changes in the kidney allowing for secretion of large quantities of $Ca^{2+}$ and $Mg^{2+}$ by renal epithelia and recovery of water via a thiazide sensitive NaCl cotransporter in the urinary bladder (Gamba, G. et al., *Proc. Nat. Acad. Sci. (USA)*, 90-2749–2753 (1993)).

In a similar fashion, adaption of marine euryhaline fish to fresh water is possible because of a net reversal of epithelial ionic gradients such that NaCl is actively reabsorbed and divalent metal ion secretion ceases (Zadunaisky, J. A. et al., *Bull. MDI Biol. Lab.*, 32:152–156 (1992)). These changes are mediated by alterations in hormones, especially prolactin, cortisol and arginine vasotocin (Norris, D. O., "Endocrine Regulation of IonoOsmotic Balance in Teleosts", Chapter 16 in *Vertebrate Endocrinology*, Lea and Febiger, Philadelphia, Pa. (1985)). These alterations in a cluster of critical hormones and functional changes in epithelial transport in gill, intestine, bladder and kidney are vital not only to rapid euryhaline adaption, but also throughout development of fish embryos, larvae and during metamorphosis.

As described in detail in Example 1, Aquatic PVCR protein has been localized on the plasma membrane of selected epithelial cells in marine species. Specifically, Aquatic PVCR has been located on the apical membrane of epithelial cells of the collecting duct and late distal tubule of the elasmobranch kidney. Aquatic PVCR protein has also been found on the apical membranes of epithelial cells in kidney tubules, gill, urinary bladder and intestine of teleosts. As used herein, the term "apical membrane" or "apical side" refers to the "outside" of the epithelial cell exposed to e.g., urine, rather than the basal side of the cell exposed e.g., to the blood. The apical membrane is also referred to herein as facing the lumen, or interior of e.g., the kidney tubule or intestine. Aquatic PVCR was also found in specific regions of teleost brain.

The Aquatic PVCR has also been localize to the lamellae of the olfactory organ of the dogfish shark. The PVCR was located by using these immunochemistry methods. A detectable antibody, referred herein as antibody/antisera 1169, that is specific to a conserved region of the PVCR was used to find this PVCR. See FIG. 31 and Example 8. Aquatic species are able to "smell" or otherwise sense the ion concentrations and/or salinity in their environment.

The Aquatic PVCR proteins, described herein, can be isolated and characterized as to its physical characteristics (e.g., molecular weight, isoelectric point) using laboratory techniques common to protein purification, for example, salting out, immunoprecipation, column chromatography, high pressure liquid chromatography or electrophoresis. Aquatic PVCR proteins referred to herein as "isolated" are Aquatic PVCR proteins separated away from other proteins and cellular material of their source of origin. These isolated Aquatic PVCR proteins include essentially pure protein, proteins produced by chemical synthesis, by combinations of biological and chemical synthesis and by recombinant methods.

Aquatic PVCR proteins can be further characterized as to its DNA and encoded amino acid sequences as follows: A complementary DNA (cDNA) encoding a highly conserved region of the mammalian CaR, as described in Brown, E. G. et al., *Nature*, 366:575–580 (1993) or Riccardi, D. J. et al., *Proc. Nat. Acad. Sci USA*, 92:131–135 (1995), the teachings of which are incorporated by reference, can be used as a probe to screen a cDNA library prepared from e.g., flounder urinary bladder cells to identify homologous receptor proteins. Techniques for the preparation of a cDNA library are well-known to those of skill in the art. For example, techniques such as those described in Riccardi, D. J. et al., *Proc. Nat. Acad. Sci USA*, 15 92:131–135 (1995), the teachings of which are incorporated herein by reference, can be used. Positive clones can be isolated, subcloned and their sequences determined.

Using the sequences of either a full length or several partial cDNAs, the complete nucleotide sequence of the flounder PVCR can be obtained and the encoded amino acid sequence deduced. The sequences of the Aquatic PVCR can be compared to mammalian CaRs to determine differences and similarities.

Similar techniques can be used to identify homologous Aquatic PVCR in other marine species. In particular, a small peptides were used to raise an antibody that is specific to PVCRs. In particular, two antisera were developed. One antisera was raised to a 23-mer peptide, referred as, "4641 antisera or 4641 antibody." A second antisera was raised against a 17-mer peptide, referred to as "1169 antisera" or "1169 antibody." By comparing mammalian receptors and determining a conserved region that is common to all, both the 23-mer and 17-mer peptide were identified and used.

The 23-mer peptide has the sequence: DDDYGRPGIEK-FREEAEERDICI (SEQ ID NO.: 13). The 17-mer peptide has the sequence: ARSRNSADGRSGDDLPC.(SEQ ID NO.: 14).

Recombinant Aquatic PVCR proteins can be expressed according to methods well-known to those of skill in the art. For example, PVCR can be expanded in oocytes of the frog, *Xenopus laevis*, both to prove identity of the cDNA clone and to determine the profile of activation of Aquatic PVCR proteins as compared to mammalian CaR proteins. Exemplary techniques are described in (Brown, E. G. et al., *Nature*, 366:575–580 (1993); Riccardi, D. J. et al., *Proc. Nat. Acad. Sci USA*, 92:131–135 (1995)), the teachings of which are incorporated herein by reference.

As described in Example 2, a 4.4 kb homolog of the mammalian CaR has been found in flounder urinary bladder together with abundant 3.8 kb thiazide-sensitive NaCl cotransporter transcript. Using a homology cloning strategy, a cDNA library from dogfish shark kidney was prepared and screened to obtain multiple cDNA clones with partial homology to mammalian CaRs as described in Example 3. One clone called Shark Kidney-Calcium Receptor Related Protein (SKCaR-RP) was isolated and characterized. SKCAR-RP (also referred to herein as Shark Aquatic PVCR) is 4,131 nucleotides in size (SEQ ID NO: 1). As shown in FIGS. 4A–F, the complete nucleotide sequence of SKCAR-RP reveals that the clone is composed of 438 nts of 5' untranslated region or UTR followed by a single open reading frame (ORF) of 3,082 nts followed by 610 nts of 3'

UTR containing regions of poly A+ RNA. A clone that expresses the shark PVCR was deposited under conditions of the Budapest Treaty with the American Type Culture Collection (ATCC), 10801 University Boulevard, Manassas, Va. 20110–2209, USA on Jan. 28, 1998, under accession number ATCC 209602.

FIGS. 5A–E show the ORF of the SKCAR-RP in single letter amino acid designations (SEQ ID NO: 2). The deduced amino acid sequence of SKCAR-RP predicts a protein of approximately 110,00 daltons that is 74% homologous to both the rat kidney PVCR protein as well as bovine parathyroid PVCR protein. As described herein, the homology was determined by BLAST software. Analysis of the amino acid sequence reveals that SKCAR-RP possesses general features that are homologous to PVCR proteins including a large extracellular domain, 7 transmembrane domains and cytoplasmic carboxyl terminal domain. In this regard, many amino acids demonstrated to be critical to PVCR function are identical in SKCAR-RP as compared to mammalian PVCR proteins including specific regions of the extracellular domain and the 7 transmembrane domains. In contrast, other regions are highly divergent, including the amino acids number 351–395 in the extracellular domain as well as the most of the carboxyl terminal region (e.g., amino acids 870–1027). Importantly, the region of amino acids present in mammalian CaRs that was used to generate anti-CaR antiserum is also present in SKCAR-RP.

Figure 6:
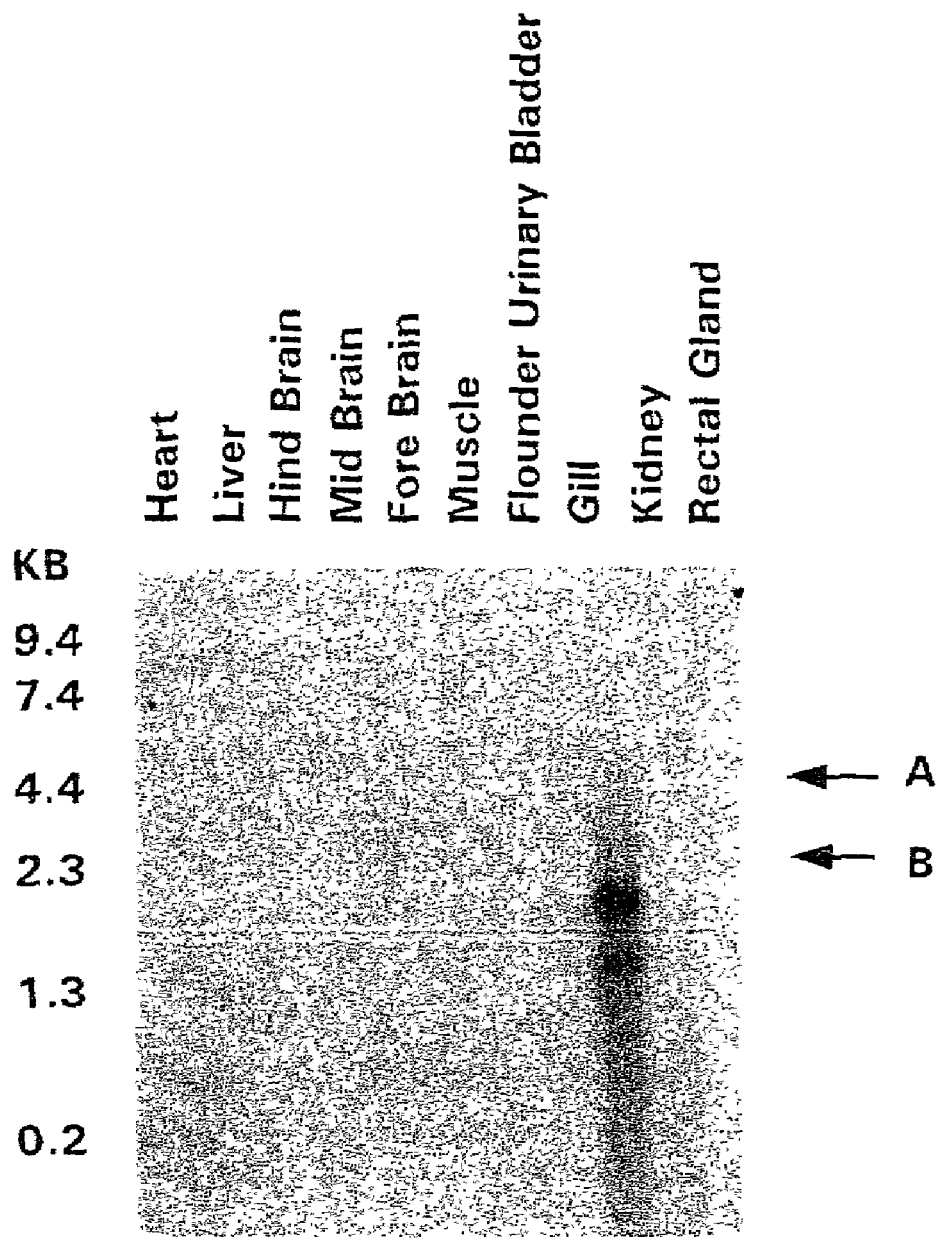
FIG. 6 is an autoradiogram showing the results of Northern blot analyses of A+RNA from various shark tissues.

As shown in FIG. 6, Northern blot analysis of MRNA from various shark tissues reveals the highest degree of SKCAR-RP in gill followed by kidney and then rectal gland. These data are highly significant since these tissues have been demonstrated to be involved with ion and water transport and body homeostasis and possess epithelial cells that stain with anti-CaR antiserum. There appears to be at least 3 distinct MRNA species of approximately 7 kb, 4.2 kb and 2.6 kb that hybridize to SKCAR-RP. The 4.2 kb likely corresponds to the SKCAR-RP clone described above.

RT-PCR amplifications were performed as described in Example 3 after isolation of poly A+ RNA from various aquatic species. Primers that permit selective amplification of a region of CaRs (nts 597–981 of RaKCaR cDNA) that is 100% conserved in all mammalian CaRs were utilized to obtain the sequences of similar CaRs in aquatic species. These primers amplify a sequence of 384 nt that is present in the extracellular domain of CaRs and presumably is involved in binding divalent metal ions. The resulting amplified 384 bp cDNA was ligated into a cloning vector and transformed into E. coli cells for growth, purification and sequencing.

Figures 7A, 7B:
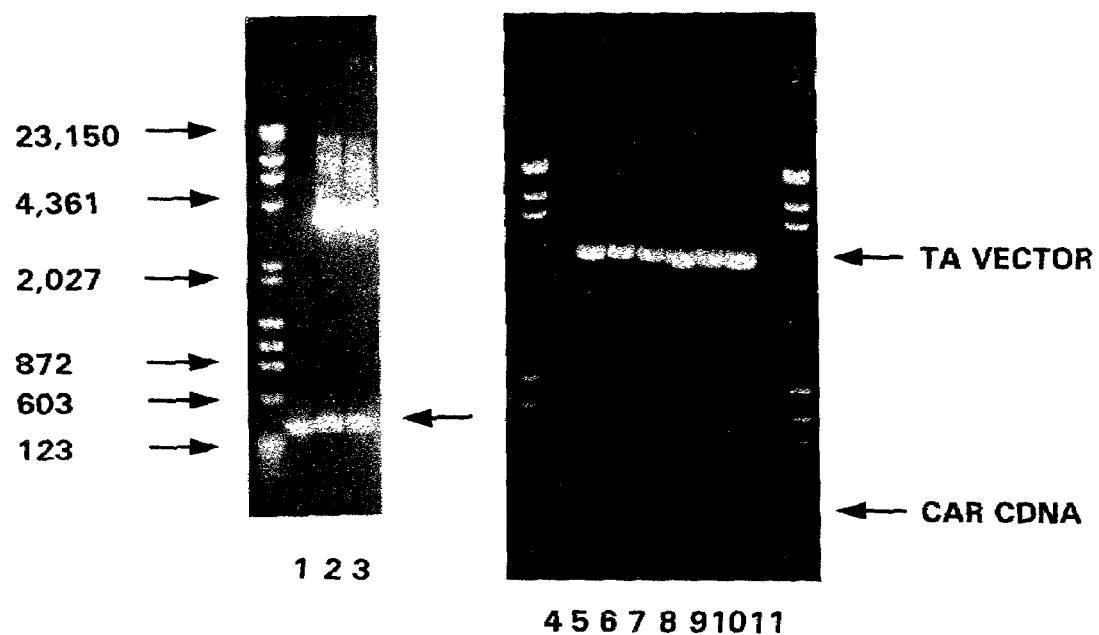
FIGS. 7A–B are autoradiograms showing the results of RT-PCR amplifications of poly A+RNA from various aquatic species.

As shown in FIGS. 7A and B, partial cDNA clones have been obtained from:

dogfish shark kidney (lane 2), flounder urinary bladder (lane 3), lumpfish liver (lane 5), lobster muscle (lane 8), clam gill (lane 9) and sea cucumber respiratory tissue (lane 10) using these identical primers. Some tissues (flounder brain-lane 7) did not yield a corresponding 384 nt cDNA despite careful controls. Similarly, no 384 nt cDNA was obtained when only water and not RT reaction mixture was added. These data suggest these 384 nt cDNAs are specific and not expressed in all tissues of aquatic organisms. Each of these 384 nt cDNAs was sequenced and found to contain a conserved nucleotide sequence identical to that present in mammalian CaRs. These data suggest the presence of CaR related proteins in classes of aquatic organisms that are widely divergent in evolution. These include teleost fish (flounder, lumpfish), elasmobranch fish (dogfish shark), crustaceans (lobster), mollusks (clam) and echinoderms (sea cucumber).

It is important to note that Aquatic PVCR sequence obtained from these clones shared complete identity of the 384 nt segment of mammalian CaRs. However, the Aquatic PVCR sequence obtained from the shark kidney clone did not. These data suggest that at least two different classes of aquatic polyvalent cation-sensing receptors exist.

In fact, additional nucleic acid sequences that encodes a PVCR were isolated from the dogfish shark. These nucleic acid sequences, SEQ ID NOs: 3 and 5, are shown in FIGS. 16 and 19, respectively. SEQ ID NO: 3 is 784 nt with an open reading frame coding for 261 amino acids (SEQ ID NO: 4, FIGS. 17 and 19). SEQ ID NO: 5 is 598 nt long and encodes a 198 amino acid sequence peptide (SEQ ID NO: 6, FIGS. 20 and 21). It is reasonable to believe that these proteins also sense polyvalent cations, as described herein. The annotated sequences for SEQ ID Nos: 3 and 5 can be found in FIGS. 18A–B and 21A–B, respectively, along with the deduced amino acid sequences (SEQ ID NOs: 4 and 6). See Example 9.

PVCRs of additional aquatic species have been isolated. For example, nucleic and amino acid sequences for Winter Flounder, Summer Flounder, and Lumpfish have been identified and determined. These sequences were determined using methods described herein and known in the art. The nucleic acid sequences for Winter Flounder (SEQ ID NO: 7), Summer Flounder (SEQ ID NO: 9) and for Lumpfish (SEQ ID NO: 11) can be found in FIGS. 22, 25, and 28, respectively. The corresponding deduced amino acid sequences for Winter Flounder (SEQ ID NO: 8), Summer Flounder (SEQ ID NO: 10) and for Lumpfish (SEQ ID NO: 12) can be found in FIGS. 23, 26, and 29, respectively. See Example 9. Clones, containing sequences for Winter Flounder, Summer Flounder, and Lumpfish were deposited under the Budapest Treaty with the American Type Culture Collection (ATCC), 10801 University Boulevard, Manassas, Va. 20110–2209, USA on Oct. 5, 2000 under accession numbers PTA-2545, PTA-2540, and PTA-2540, respectively.

Additionally, the nucleic and amino acid sequences for an aquatic PVCR were isolated in Swordfish and Lamprey. These sequences were isolated as described herein. These PVCR's function similar to the shark PVCR, as described herein and is capable of sensing ion concentrations/salinity.

The present invention is intended to encompass Aquatic PVCR proteins, and proteins and polypeptides having amino acid sequences analogous to the amino acid sequences of Aquatic PVCR proteins. Such polypeptides are defined herein as Aquatic PVCR analogs (e.g., homologues), or mutants or derivatives. Analogous amino acid sequences are defined herein to mean amino acid sequences with sufficient identity of Aquatic PVCR amino acid sequence to possess the biological activity of an Aquatic PVCR. For example, an analog polypeptide can be produced with "silent" changes in the amino acid sequence wherein one, or more, amino acid residues differ from the amino acid residues of the Aquatic PVCR protein, yet still possesses the biological activity of Aquatic PVCR. Examples of such differences include additions, deletions or substitutions of residues of the amino acid sequence of Aquatic PVCR.

Also encompassed by the present invention are analogous polypeptides that exhibit greater, or lesser, biological activity of the Aquatic PVCR proteins of the present invention.

The claimed Aquatic PVCR protein and nucleic acid sequence include homologues, as defined herein. The homologous proteins and nucleic acid sequences can be determined using methods known to those of skill in the art. Initial homology searches can be performed at NCBI against the GenBank (release 87.0), EMBL (release 39.0), and SwissProt (release 30.0) databases using the BLAST network service. Altshul, S F, et al, *Basic Local Alignment Search Tool*, J. Mol. Biol. 215: 403 (1990), the teachings of which are incorporated herein by reference. Computer analysis of nucleotide sequences can be performed using the MOTIFS and the FindPatterns subroutines of the Genetics Computing Group (GCG, version 8.0) software. Protein and/or nucleotide comparisons can also be performed according to Higgins and Sharp (Higgins, D. G. and P. M. Sharp, "Description of the method used in CLUSTAL," Gene, 73: 237–244 (1988)). Homologous proteins and/or nucleic acid sequences to the PVCR protein and/or nucleic acid sequences that encode the PVCR protein are defined as those molecules with greater than 70% sequences identity and/or similarity (e.g., 75%, 80%, 85%, 90%, or 95% homology).

The "biological activity" of Aquatic PVCR proteins is defined herein to mean the osmoregulatory activity of Aquatic PVCR mammalian PVCR proteins have been shown to mediate physiological responses to changes in body osmolality and salt content in kidney, parathyroid, calcitonin and brain cells. (Brown, E. M. et al., *New Eng. J. Med.*, 333:243, (1995); Riccardi, D. J. et al., *Proc. Nat. Acad. Sci USA*, 92:131–135 (1995); Sands, J. M. etal., *Nature (Medicine)* (1995); Brown, E. M. et al., *New England J. of Med.*, 333:234–240 (1995)). It is reasonable to believe that Aquatic PVCR proteins will possess identical, or similar osmoregulatory activities as these previously identified mammalian CaR proteins in fish kidney, gill, bladder, intestine, rectal gland and brain cells. Assay techniques to evaluate the biological activity of Aquatic PVCR proteins and their analogs are described in Brown, E. M. et al., *New Eng. J. Med.*, 333:243, (1995); Riccardi, D. J. et al., *Proc. Nat. Acad. Sci USA*, 92:131–135 (1995); Sands, J. M. et al., *Nature (Medicine)* (1995); Brown, E. M. et al., *New England J. of Med.*, 333:234–240 (1995), the teachings of which are incorporated herein by reference. Additional assays to evaluate biological activity of PVCR proteins are described in U.S. Serial No. 60/003,697, the teachings of which are also incorporated herein, in its entirety, by reference.

The "biological activity" of Aquatic PVCR is also defined herein to mean the ability of the Aquatic PVCR to modulate signal transduction pathways in specific marine species cells. In mammals, studies in normal tissues, in oocytes using recombinantly expressed CaR, and cultured cells have demonstrated that mammalian CaR protein is capable of complexing with at least two distinct types of GTP-binding (G) proteins that transmit the activation of CaR by an increase in extracellular calcium to various intracellular signal transduction pathways. One pathway consists of mammalian CaR coupling with an inhibitory Gi protein that, in turn, couples with adenylate cyclase to reduce intracellular CAMP concentrations. A second distinct pathway consists of CaR coupling to stimulatory Gq/Gall G protein that couples with phospholipase C to generate inositol 1,4,5 triphosphate that, in turn, stimulates both protein kinase C activity and increases intracellular $Ca^{2+}$ concentrations. Thus, depending on the distribution and nature of various signal transduction pathway proteins that are expressed in cells, biologically active mammalian CaRs modulate cellular functions in either an inhibitory or stimulatory manner. It is reasonable to believe that biologically active Aquatic PVCR possesses similar signal transduction activity.

The term "biologically active" also refers to the ability of the PVCR to sense ion concentrations in the surrounding environment. The PVCR senses various polyvalent cations including calcium, magnesium and/or sodium. The PVCR is modulated by varying ion concentrations. For instance, the PVCR may be modulated (e.g., increased expression, decreased expression and/or activation) in response to a change (e.g., increase or decrease) in ion concentration (e.g., calcium, magnesium, or sodium). See Example 6. Responses to changes in ion concentrations of a fish containing a PVCR include the ability for a fish to adapt to the changing ion concentration. Such responses include the amount the fish drinks, the amount of urine output, and the amount of water absorption. Responses also include changes biological processes that affect the body composition of the fish and its ability to excrete contaminants.

The claimed PVCR proteins also encompasses biologically active polypeptide fragments of the Aquatic PVCR proteins, described herein. Such fragments can include only a part of the full-length amino acid sequence of an Aquatic PVCR yet possess osmoregulatory activity. For example, polypeptide fragments comprising deletion mutants of the Aquatic PVCR proteins can be designed and expressed by well-known laboratory methods. Such polypeptide fragments can be evaluated for biological activity, as described herein.

Antibodies can be raised to the Aquatic PVCR proteins and analogs, using techniques known to those of skill in the art. These antibodies polyclonal, monoclonal, chimeric, or fragments thereof, can be used to immunoaffinity purify or identify Aquatic PVCR proteins contained in a mixture of proteins, using techniques well known to those of skill in the art. These antibodies, or antibody fragments, can also be used to detect the presence of Aquatic PVCR proteins and homologs in other tissues using standard immunochemistry methods.

The present invention also encompasses isolated nucleic acid sequences encoding the Aquatic PVCR proteins described herein, and fragments of nucleic acid sequences encoding biologically active PVCR proteins. Fragments of the nucleic acid sequences, described herein, as useful as probes to detect the presence of marine species CaR. Specifically provided for in the present invention are DNA/RNA sequences encoding Aquatic PVCR proteins, the fully complementary strands of these sequences, and allelic variations thereof. Also encompassed by the present invention are nucleic acid sequences, genomic DNA, cDNA, RNA or a combination thereof, which are substantially complementary to the DNA sequences encoding Aquatic PVCR, and which specifically hybridize with the Aquatic PVCR DNA sequences under conditions of stringency known to those of skill in the art, those conditions being sufficient to identify DNA sequences with substantial nucleic acid identity. As defined herein, substantially complementary means that the sequence need not reflect the exact sequence of Aquatic PVCR DNA, but must be sufficiently similar in identity of sequence to hybridize with Aquatic PVCR DNA under stringent conditions.

Conditions of stringency are described in e.g., Ausebel, F. M., et al., Current Protocols in Molecular Biology, (Current Protocols, 1994). For example, non-complementary bases can be interspersed in the sequence, or the sequences can be longer or shorter than Aquatic PVCR DNA, provided that the sequence has a sufficient number of bases complementary to Aquatic PVCR to hybridize therewith. Exemplary hybridization conditions are described herein and in Brown, E. M., et al. *Nature*, 366:575 (1993). For example, conditions such as 1×SSC 0. 1% SDS, 50°, or 0.5×SSC, 0. 1% SDS, 50° can be used as described in Examples 2 and 3.

The Aquatic PVCR DNA sequence, or a fragment thereof, can be used as a probe to isolate additional Aquatic PVCR homologs. For example, a cDNA or genomic DNA library from the appropriate organism can be screened with labeled Aquatic PVCR DNA to identify homologous genes as described in e.g., Ausebel, F. M., et al., *Current Protocols in Molecular Biology*, (Current Protocols, 1994).

Typically the nucleic acid probe comprises a nucleic acid sequence (e.g. SEQ ID NO: 1, 3, 5, 7, 9, or 11) and is of sufficient length and complementarity to specifically hybridize to nucleic acid sequences which encode Aquatic species PVCR.

The requirements of sufficient length and complementarity can be easily determined by one of skill in the art.

Uses of nucleic acids encoding cloned receptors or receptor fragments include one or more the following: (1) producing receptor proteins which can be used, for example, for structure determination, to assay a molecule's activity on a receptor, and to obtain antibodies binding to the receptor; (2) being sequenced to determine a receptor's nucleotide sequence which can be used, for example, as a basis for comparison with other receptors to determine conserved regions, determine unique nucleotide sequences for normal and altered receptors, and to determine nucleotide sequences to be used as target sites for antisense nucleic acids, ribozymes, hybridization detection probes, or PCR amplification primers; (3) as hybridization detection probes to detect the presence of a native receptor and/or a related receptor in a sample; and (4) as PCR primers to generate particular nucleic acid sequence regions, for example to generate regions to be probed by hybridization detection probes.

The claimed PVCR proteins and/or nucleic acid sequences include fragment thereof. Preferably, the nucleic acid contains at least 14, at least 20, at least 27, at least 45, and at least 69, contiguous nucleic acids of a sequence provided in SEQ. ID. NO. 1, SEQ. ID. NO. 3, SEQ. ID. NO. 5, SEQ. ID. NO. 7, SEQ. ID. NO. 9, or SEQ. ID. NO. 11. Advantages of longer-length nucleic acid include producing longer-length protein fragments having the sequence of a calcium receptor which can be used, for example, to produce antibodies; increased nucleic acid probe specificity under high stringent hybridization assay conditions; and more specificity for related inorganic ion receptor nucleic acid under lower stringency hybridization assay conditions.

Another aspect of the present invention features a purified nucleic acid encoding an inorganic ion receptor or fragment thereof. The nucleic acid encodes at least 6 contiguous amino acids provided in SEQ. ID. NO. 2, SEQ. ID. NO. 4, SEQ. ID. NO. 6, SEQ. ID. NO. 8, SEQ. ID. NO. 10, SEQ. ID. NO. 12, or SEQ ID NO: 14. Due to the degeneracy of the genetic code, different combinations of nucleotides can code for the same polypeptide. Thus, numerous inorganic ion receptors and receptor fragments having the same amino acid sequences can be encoded for by difference nucleic acid sequences. In preferred embodiments, the nucleic acid encodes at least 12, at least 18, at least 23, or at least 54 contiguous amino acids of SEQ. ID. NO. 2, SEQ. ID. NO. 4, SEQ. ID. NO. 6, SEQ. ID. NO. 8, SEQ. ID. NO. 10, SEQ. ID. NO. 12, or SEQ ID NO: 14.

Another aspect of the present invention features a purified nucleic acid having a nucleic acid sequence region of at least 12 contiguous nucleotides substantially complementary to a sequence region in SEQ. ID. NO. 1, SEQ. ID. NO. 3, SEQ. ID. NO. 5, SEQ. ID. NO. 7, SEQ. ID. NO. 9, or SEQ. ID. NO. 11. By "substantially complementary" is meant that the purified nucleic acid can hybridize to the complementary sequence region in nucleic acid encoded by SEQ. ID. NO. 1, SEQ. ID. NO. 3, SEQ. ID. NO. 5, SEQ. ID. NO. 7, SEQ. ID. NO. 9, or SEQ. ID. NO. 11 under stringent hybridizing conditions. Such nucleic acid sequences are particularly useful as hybridization conditions, only highly complementary nucleic acid sequences hybridize. Preferably, such conditions prevent hybridization of nucleic acids having 4 mismatches out of 20 contiguous nucleotides, more preferably 2 mismatches out of 20 contiguous nucleotides, most preferably one mismatch out of 20 contiguous nucleotides. In preferred embodiments, the nucleic acid is substantially complementary to at least 20, at least 27, at least 45, or at least 69 contiguous nucleotides provided in SEQ. ID. NO. 1, SEQ. ID. NO. 3, SEQ. ID. NO. 5, SEQ. ID. NO. 7, SEQ. ID. NO. 9, or SEQ. ID. NO. 11.

Another aspect of the present invention features a purified polypeptide having at least 6 contiguous amino acids of an amino acid sequence provided in SEQ. ID. NO. 2, SEQ. ID. NO. 4, SEQ. ID. NO. 6, SEQ. ID. NO. 8, SEQ. ID. NO. 10, or SEQ. ID. NO. 12. By "purified" in reference to a polypeptide is meant that the polypeptide is in a form (i.e., its association with other molecules) distinct from naturally occurring polypeptide. Preferably, the polypeptide is provided as substantially purified preparation representing at least 75 %, more preferably 85 %, most preferably 95 % or the total protein in the preparation. In preferred embodiments, the purified polypeptide has at least 12, 18, 23, or 54 contiguous amino acids of SEQ. ID. NO. 2, SEQ. ID. NO. 4, SEQ. ID. NO. 6, SEQ. ID. NO. 8, SEQ. ID. NO. 10, or SEQ. ID. NO. 12.

Preferred receptor fragments include those having functional receptor activity, a binding site, epitope for antibody recognition (typically at least six amino acids) (e.g., antisera 1169). Such receptor fragments have various uses such as being used to obtain antibodies to a particular region and being used to form chimeric receptors with fragments of other receptors create a new receptor having unique properties.

The invention also features derivatives of full-length inorganic ion receptors and fragments thereof having the same, or substantially the same, activity as the full-length receptor or fragment. Such derivatives include amino acid addition(s), substitution(s), and deletion(s) to the receptor which do not prevent the derivative receptor from carrying out one or more of the activities of the parent receptor.

Another aspect of the present invention features a recombinant cell or tissue. The recombinant cell or tissue is made up of a recombined nucleic acid sequence encoding at least 6 contiguous amino acids provided in SEQ. ID. NO. 2, SEQ. ID. NO. 4, SEQ. ID. NO. 6, SEQ. ID. NO. 8, SEQ. ID. NO. 10, or SEQ. ID. NO. 12 and a cell able to express the nucleic acid. Recombinant cells have various uses including acting as biological factories to produce polypeptides encoded for by the recombinant nucleic acid, and for producing cells containing a functioning PVCR protein. Cells containing a functioning PVCR can be used, for example, to screen to antagonists or agonists.

As described in Example 4, it is demonstrated that the Aquatic PVCR protein plays a critical role in the adaption of euryhaline fish to environments of various salinities. Adaption of the killifish, *Fundulus heteroculitus*, to seawater resulted in steady state expression of Aquatic PVCR MRNA in various tissues.

It is also demonstrated herein that PVCR protein undergoes rearrangement within epithelial cells of the urinary bladder in flounder adapted to brackish water as compared to full strength sea water. This directly correlates with alterations the rate of NaCl transport by these cells.

Preliminary experiments shows that winter flounder were adapted to live in 1/10th seawater (100 mOsm/kg) by reduction in salinity from 450 mM NaCl to 45 mM NaCl over an interval of 8 hrs. (Further experimentation illustrated that winter and summer flounder can be maintained in 1/10 or twice the salinity for over a period of 6 months.) After a 10 day interval where these fish were fed a normal diet, the distribution of the PVCR in their urinary bladder epithelial cells was examined using immunocytochemistry. PVCR immunostaining is reduced and localized primarily to the apical membrane of epithelial cells in the urinary bladder. In contrast, the distribution of PVCR in epithelial cells lining the urinary bladders of control flounders continuously exposed to full strength seawater is more abundant and present in both the apical membranes as well as in punctate regions throughout the cell. These data are consistent with previous Northern data since more PVCR protein is present in the urinary bladders of seawater fish vs fish adapted to brackish water. These data suggest that PVCR protein may be present in vesicles in epithelial cells of the urinary bladder and that in response to alterations in salinity, these vesicles move from the cell cytoplasm to the apical surface of these epithelial cells. Since these same epithelial cells possess abundant NaCl cotransporter protein that is responsible for water reabsorption in the urinary bladder, these data suggest that the PVCR protein modulates NaCl transport in the flounder urinary bladder by altering the proportion of NaCl cotransporter protein that is present in the apical membrane. As urinary $Mg^{2+}$ and $Ca^{2+}$ concentrations increase when fish are present in full strength sea water, activation of apical PVCR protein causes endocytosis and removal of NaCl cotransporter from the apical membrane and thus reduction in urinary bladder water transport.

As a result of the work described herein, methods are now provided that facilitate euryhaline adaptation of fish to occur, and improve the adaption. More specifically, methods are now available to regulate salinity tolerance in fish by modulating (e.g., alternating, activating and or expressing) the activity of the Aquatic PVCR protein present in epithelial cells involved in ion transport, as well as in endocrine and nervous tissue. For example, salinity tolerance of fish adapted (or acclimated) to fresh water can be increased by activating the Aquatic PVCR, for example, by increasing the expression of Aquatic PVCR in selected epithelial cells, resulting in the secretion of ions and seawater adaption. Specifically, this would involve regulatory events controlling the conversion of epithelial cells of the gill, intestine and kidney. In the kidney, PVCR activation will facilitate excretion of divalent metal ions including Ca2+ and $Mg^{2+}$ by renal tubules. In the gill, PVCR activation will reduce reabsorption of ions by gill cells that occurs in fresh water and promote the net excretion of ions by gill epithelia that occurs in salt water. In the intestine, PVCR activation will permit reabsorption of water and ions across the G.I. tract after their ingestion by fish.

Alternatively, the salinity tolerance of fish adapted to seawater can be decreased by inhibiting the Aquatic PVCR, for example, by decreasing the expression of Aquatic PVCR in selected epithelial cells, resulting in alterations in the absorption of ions and freshwater adaption. Selected epithelial cells include, e.g., kidney, bladder, intestinal and gill cells.

The presence of Aquatic PVCR in brain reflects both its involvement in basic neurotransmitter release via synaptic vesicles (Brown, E. M. et al., New England J. of Med., 333:234–240 (1995)), as well as its activity to trigger various hormonal and behavioral changes that are necessary for adaptation to either fresh water or marine environments. For example, increases in water ingestion by fish upon exposure to salt water is mediated by PVCR activation in a manner similar to that described for humans where PVCR activation by hypercalcemia in the subfornical organ of the brain cause an increase in water drinking behavior (Brown, E. M. et al., New England J. of Med., 333:234–240 (1995)). In fish, processes involving both alterations in serum hormonal levels and behavioral changes are mediated by the brain. These include the reproductive and spawning of euryhaline fish in fresh water after their migration from salt water as well as detection of salinity of their environment for purposes of feeding, nesting, migration and spawning.

Data obtained recently from mammals now suggest that PVCR activation plays a pivotal role in coordinating these events. For example, alterations in plasma cortisol have been demonstrated to be critical for changes in ion transport necessary for adaptation of salmon smolts from fresh water to salt water (Veillette, P. A., et al., Gen. and Comp. Physiol., 97:250–258 (1995). As demonstrated recently in humans, plasma Adrenocorticotrophic Hormone (ACTH) levels that regulate plasma cortisol levels are altered by PVCR activation.

"Salinity" refers to the concentration of various ions in a surrounding aquatic environment. In particular, salinity refers to the ionic concentration of calcium, magnesium and/or sodium (e.g., sodium chloride). "Normal salinity" levels refers to the range of ionic concentrations of typical water environment in which an aquatic species naturally lives. For winter and summer flounder, normal salinity or normal seawater concentrations are about 10 mM Ca, 25 mM Mg, and 450 mM NaCl. "Salinity tolerance" refers to the ability of a fish to live or survive in a salinity environment that is different than the salinity of its natural environment. The upper or lower limit of ionic concentrations in which the fish can survive have been defined. Salinity tolerance of a fish has been defined to be between at least 4× and 1/50, or 3× and 1/25, or preferably, twice and 1/10 the normal salinity.

Winter and summer flounder were maintained in at least twice the normal salinity or 1/10 the normal salinity. See Example 10. These fish can be maintained in these environments for long periods of time (e.g., over 3 months, over 6 months, or over 1 year). These limits were defined by decreasing or increasing the ionic concentrations of calcium, magnesium, and sodium, keeping a constant ratio between the ions. These salinity limits can be further defined by increasing and/or decreasing an individual ion concentration, thereby changing the ionic concentration ratio among the ions. Increasing and/or decreasing individual ion concentrations can increase and/or decrease salinity tolerance. "Hypersalinity" or "above normal salinity" levels refers to a level of at least one ion concentration that is above the level found in normal salinity. "Hyposalinity" or "below normal salinity" levels refers to a level of at least one ion concentration that is below the level found in normal salinity.

Maintaining winter and summer founder in this environment for about 3 months induced noticeable and significant changes occurred to the body composition of the flounder. These fish were slowly adapted to the hypersalinity or hyposalinity environments over a period of 15 days. Body composition refers to various characteristics of the fish, including, but not limited to, weight, muscle, fat, protein, moisture, taste, or thickness. Alteration of the body composition means inducing a change in one of these characteristics. Maintaining fish in ¹/₁₀ the normal salinity results in a fish that is twice as thick, 70% fatter, and "less fishy,"(e.g., milder flavor) tasting fish than those fish maintained in hypersalinity environments. See Example 10. A fish maintained in low salinity or hyposalinity can increase its fat content by at least 10% or 20%, and preferably by at least 30%, 40%, or 50% than those fish maintained in normal salinity. Similarly, a fish maintained in low salinity or hyposalinity can increase its thickness by at least 30% or 40%, and preferably by at least 50%, 60%, or 70% than those fish maintained in normal salinity. A fish maintained in high salinity or hypersalinity can decrease its fat content by at least 10% or 20%, and preferably by at least 30%, 40%, or 50% than those fish maintained in normal salinity. Similarly, a fish maintained in high salinity or hypersalinity can decrease its thickness by at least 30% or 40%, and preferably by at least 50%, 60%, or 70% than those fish maintained in normal salinity.

Maintaining fish in a hypersalinity environment also results in fish with a reduced number of parasites or bacteria. Preferably, the parasites and/or bacteria are reduced to a level that is safe for human consumption, raw or cooked. More preferably, the parasites and/or bacteria are reduced to having essentially no parasites and few bacteria. These fish must be maintained in a hypersalinity environment long enough to rid the fish of these parasites or bacteria, (e.g., for at least a few days or at least a few weeks).

The host range of many parasites is limited by exposure to water salinity. For example, *Diphyllobothrium* species commonly known as fish tapeworms, is encountered in the flesh of fish, primarily fresh water or euryhaline species including flounder of salmon. *Foodborne Pathogenic Microorganisms and Natural Toxins Handbook.* 1991. US Food and Drug Administration Center for Food Safety and Applied Nutrition, the teachings of which are incorporated herein by reference in their entirety. In contrast, its presence in the flesh of completely marine species is much reduced or absent. Since summer flounder can survive and thrive at salinity extremes as high as 58 ppt (1.8 times normal seawater) for extended periods in recycling water, exposure of summer flounder to hypersalinity conditions might be used as a "biological" remediation process to ensure that no Diphyllobothrium species are present in the GI tract of summer flounder prior to their sale as product.

Recent data from Cole et al, J. Biol. Chem. 272:12008–12013, 1997, (the teachings of which are incorporated herein by reference in their entirety) show that winter flounder elaborate an antimicrobial peptide from their skin to prevent bacterial infections. Their data reveals that in the absence of pleurocidin, *E. coli* are killed by high concentrations of NaCl. In contrast, low concentrations of NaCl (<300 mM NaCl) allow *E. Coli* to grow and under these conditions pleurocidin presumably helps to kill them. These data provide evidence of NaCl killing of *E. Coli*, as well as highlight possible utility of bacterial elimination in fish.

Similarly, maintaining fish in a hyposalinity environment results in a fish with a reduced amount of contaminants (e.g., hydrocarbons, amines or antibiotics). Preferably, the contaminants are reduced to a level that is safe for human consumption, raw or cooked, and produces a milder, "less fishy" tasting fish. More preferable, the contaminants are reduced to having essentially very little contaminants left in the fish. These fish must be maintained in a hyposalinity environment long enough to rid the fish of these contaminants, (e.g., for at least a few days or a few weeks).

Organic amines, such as trimethylamine oxide (TMAO) produce a "fishy" taste in seafood. They are excreted via the kidney in flounder. (Krogh, A. Osmotic Regulation in Aquatic Animals, Cambridge University Press, Cambridge, U.K. pgs 1–233, 1939, the teachings of which are incorporated herein by reference in their entirety). TMAO is synthesized by marine organisms consumed by fish that accumulate the TMAO inn their tissues. Depending on the species of fish, the muscle content of TMAO and organic amines is either large accounting for the "strong" taste of bluefish and herring or small such as in milder tasting flounder.

TMAO is an intracellular osmolyte and its accumulation in cells prevents osmotic loss of water produces by hypertonic seawater (Forster, R P and L Goldstein, Formation of Excretory Products Chapter 5 in Fish Physiology, Edited by W S Hoar, D J Randall and J R Brett Volume VIII Bioenergics and Growth. Academic Press, New York, N.Y. pages 313–345, 1969, the teachings of which are incorporated herein by reference in their entirety). The excretion of TMAO by marine teleost fish such as winter flounder occurs almost exclusively via the kidney. Thus, in low salinities urine flow in winter flounder is high and dietary amines including TMAO are almost completely excreted. Elger, E. B. Elger, H. Hentschel and H. Stolte, Adaptation of renal function to hypotonic medium in the winter flounder (*Psuedupleuronecies americanus*). J. Comp. Physio. B157:21–30 (1987), the teachings of which are incorporated herein in their entirety. In full strength or hyperosmotic seawater, urine flow is much diminished and amine excretion is greatly reduced and therefore accumulates in the flounder muscle. Thus, muscle levels of amines can be altered by subjecting flounder to differing osmotic environments and likely result in winter flounders with differing tastes.

Exposure of either winter or summer flounders to waters of extreme differences in salinity (3–4 vs 58 ppt) produces profound changes in the kidney function of these fish that allow toxic compounds such as antibiotics and heavy metal to be excreted. At low salinities (3–4 ppt) the glomerular filtration and urinary flow rates are 10–100 fold larger as compared to identical fish exposed to full strength seawater. High glomerular filtration and urine flow rates provide for a large increase in the clearance of a variety of organic compounds including antibiotics used in aquaculture (Physicians Desk Reference, 49th Edition, Medical Economics Data Production Company, Montvale, N.Y. page 2103, the teachings of which are incorporated herein by reference in their entirety), as well as heavy metals including $Ni^{2+}$, $Pb^{2+}$ (Forster, R P and L Goldstin. 1969. Formation of Excretory Products Chapter 5 in Fish Physiology, Edited by W S Hoar, D J Randall and J R Brett Volume VIII Bioenergics and Growth. Academic Press. New Your, N.Y. pages 313–345 (the teachings of which are incorporated herein by reference in their entirety)). Exposure of flounder to an interval of low salinity prior to market would produce high urine flow rates and, therefore, reduce any tissue burdens of toxic or antibiotic compounds acquired during growth. This method serves as a effective strategy to reduce environmental contaminants to their lowest levels possible.

Methods encompassed by the present invention include methods of activating or deactivating the Aquatic PVCRs described herein. The term "activation" as used herein means to make biologically functional, e.g., rendering a cell surface receptor capable of stimulating a second messenger which results in modulation of ion secretion. This could be in the form of either an inhibition of signal transduction pathways, e.g., via a Gi protein, or stimulation of other pathways via. e.g., a Gq/Gall protein. As a result of these alterations, ion transport by epithelial cells is reduced or stimulated. Also, activation can be related to expression (e.g., an increase in expression).

For example, a compound, or substance, which acts as an agonist can interact with, or bind to, the Aquatic PVCR, thereby activating the Aquatic PVCR, resulting in an increase of ion secretion in selected epithelial cells. An agonist can be any substance, or compound, that interacts with, or binds to, the Aquatic PVCR resulting in activation of Aquatic PVCR. Agonists encompassed by the present invention include inorganic ions, such as the polyvalent cations calcium, magnesium and gadolinium, and organic molecules such as neomycin. Other agonists, include inorganic compounds, nucleic acids or proteins can be determined using the techniques described herein.

Agonists also encompassed by the present invention can include proteins or peptides or antibodies that bind to the Aquatic PVCR resulting in its activation.

Activation of the Aquatic PVCR is typically direct activation. For example, an inorganic molecule or peptide binds directly to the receptor protein resulting in the activation of Aquatic PVCR. However, activation of the Aquatic PVCR can also be indirect activation, such as would occur when e.g., an antibody is available to bind an Aquatic PVCR antagonist, thus permitting activation of the Aquatic PVCR The term "deactivation" or "inactivation" as used herein means to completely inhibit or decrease biological function. For example, deactivation is when a cell surface receptor is incapable of stimulating a second messenger. Specifically, as used herein, deactivation of the Aquatic PVCR occurs when the Aquatic PVCR is rendered incapable of coupling with, or stimulating, a second messenger, resulting in the absorption of ions in selected epithelial cells. Deactivation can be direct or indirect. For example, an antagonist can interact with, or bind directly to the Aquatic PVCR, thereby rendering the Aquatic PVCR incapable of stimulation of a messenger protein.

Alternatively, deactivation can be indirect. For example, an antagonist can deactivate Aquatic PVCR by preventing, or inhibiting an agonist from interacting with the Aquatic PVCR. For example, a chelator can bind calcium ions and, thus prevent the calcium ions from binding to the Aquatic PVCR. Antagonists of the Aquatic PVCR can be any substance capable of directly interacting with, or binding to, the Aquatic PVCR or interacting with, or binding to, an agonist of the Aquatic PVCR that results in deactivation of the Aquatic PVCR. Antagonists encompassed by the present invention can include, for example, inorganic molecules, organic molecules, proteins or peptides. Antagonists can also be nucleic acids, such as anti-sense DNA or RNA sequences that bind to the DNA encoding the Aquatic PVCR, thereby preventing or inhibiting transcription into MRNA. Antagonists can also be anti-sense RNA that binds to the PVCR transcript, thereby preventing, or inhibiting translation.

Candidate substances, (e.g., compounds, peptldes or nucleic acids) to be evaluated for their ability to regulate Aquatic PVCR activity can be screened in assay systems to determine activity. For example, one assay system that can be used is the frog oocyte system expressing Aquatic PVCR described in Brown, E. G. et al., *Nature,* 366:575–580 (1993); Riccardi, D. J. et al., *Proc. Nat. Acad. Sci USA,* 92:131–135 (1995).

A functional assay to screen for compounds that alter PVCR mediated NaCl transport function in adult flounder urinary bladder can also be used to screen candidate compounds for their ability to modulate Aquatic PVCR. Transport of NaCl via the thiazide sensitive NaCl cotransporter in the flounder urinary bladder is important in its adaptation to various salinities. NaCl transport is readily quantified using a isolated bladder preparation from adult flounder and measurement of transepithelial $Ca^{2+}$ sensitive short circuit current, as described in (Gamba, G. et al., *Proc. Nat. Acad. Sci.* (*USA*), 90-2749–2753 (1993)). Use of this isolated in vitro assay system can establish a direct effect of Aquatic PVCR function or transepithelial transport of ions important for salinity adaptation. Compounds identified using the frog oocyte assay and in vitro NaCl transport assay system can be further tested in whole animal adaptation experiments.

For example, to screen for PVCR reactive compounds (both agonists and antagonists) an assay previously used for study of ion and water transport in isolated flounder urinary bladders (Renfro, L. J. Am. J. Physiol. 228:52–61, 1975) has been used. As described herein (Example 5), this assay has now been adapted to screen PVCR agonists and provided data showing that water reabsorption is >85% inhibited by application of thiazide (specific inhibitor of the thiazide sensitive NaCl cotransporter); water reabsorption is >90% inhibited by application of gadolinium (a PVCR specific agonist); water reabsorption is >50% inhibited by application of neomycin (a PVCR specific agonist); and exposure of the bladder to PVCR agonists is reversible upon removal of either gadolinium or neomycin.

As a further result of the work, methods are provided to test the function of PVCR in developing fish, and to specifically select for fish with altered PVCR functional and osmotic tolerance. The developmental expression of PVCR in developing embryo, larval and metamorphic forms of fish can be determined using antibodies that recognize Aquatic PVCR and/or mammalian CaR, or by using Aquatic and/or mammalian cDNA probes, or a combination of these techniques. Initial screening of gametes, larval or metamorphic forms of fish can be tested using immunohistochemistry, such as described in Example 1, to determine at what stage of development the PVCR protein is expressed in developing fish.

Based on the immunochemistry studies of the Aquatic PVCR structure, function and developmental expression, specific selection assays can be designed to identify fish, e.g., flounder, halibut or cod, species with altered Aquatic PVCR function that can survive in fresh water, while those possessing normal PVCR function will die. These acute survival assays can evaluate the overall effect of PVCR agonists and antagonists identified by e.g., the frog oocyte expression assay. These assays will test the potency of various PVCR active compounds on improving or reducing survival of various fish or embryos. The ability to identify a single individual fish with alterations in PVCR function and osmoregulation from many wild type fish possessing normal characteristics will permit the propagation of specific strains of fish that exhibit specific salinity tolerance characteristics. Development of larval forms of cod, halibut or flounder that survive in fresh water can then be utilized in experiments to test whether new food sources could be used in their rearing.

Successful development of these goals would then permit these species to be raised initially in protected fresh water hatcheries and later transferred to marine conditions similar to those presently utilized for aquaculture of salmon.

Also encompassed by the present invention are methods of modulating the activation of the Aquatic PVCR by altering the DNA encoding the Aquatic PVCR, and thus, altering the subsequent expression of Aquatic PVCR protein in various tissues. For example, anti-sense nucleic acid sequences (either DNA or RNA) can be introduced into e.g., epithelial cells in fish kidney, where the anti-sense sequence binds to the Aquatic PVCR gene and inhibits, or substantially decreases its transcription into MRNA. Alternatively, the anti-sense sequence can bind to the Aquatic PVCR MRNA and inhibit, or substantially decrease, its translation into amino acid sequence.

Alternatively, a mutated or chimeric Aquatic PVCR gene construct (e.g., a mutated or chimeric SEQ ID NO: 1) can be inserted into, e.g. fish eggs, to produce new marine strains with enhanced, or decreased, Aquatic PVCR protein activity. The anti-sense sequence or gene construct is introduced into the cells using techniques well-known to those of skill in the art. Such techniques are described in Hew, C. L., et al., *Mol. Aguatic Biol. Biotech.*, 1:380717 (1992) and Du, S. J., et al., *Biotechnology*, 10:176–181 (1992), the teachings of which are incorporated herein by reference.

Based on the work described herein, new methodologies that will regulate the adaptation of fish, particularly flounder, halibut and cod, to environments of varying salinities are now available. For example, methods are now available to adapt developing forms of flounder, halibut or cod to fresh water environments. Rearing of these species in fresh water will allow for new approaches to the problems of feeding and successful rearing of larval forms of these fish species. Methods are also now available for selection and propagation of new strains of fish (e.g., flounder, halibut and cod) that will possess alterations in their salinity tolerance such that they can be raised in fresh water, then transferred to seawater. This approach has many advantages since it will both diversify the aquaculture industry and make use of existing hatcheries and facilities to produce flounder, cod or halibut as well as salmon.

The present invention is illustrated by the following Examples, which are not intended to be limited in any way.

EXAMPLE 1

Immunohistochemistry of the PVCR Protein Present in Aquatic Species Epithelial Cells Tissues from fish were fixed by perfusion with 2% paraformaldehyde in appropriate Ringers solution corresponding to the osmolality of the fish after anesthesitizing the animal with MS-222. Samples of tissues were then obtained by dissection, fixed by immersion in 2% paraformaldehyde, washing in Ringers then frozen in an embedding compound, e.g., O.C.T.™ Miles, Inc. Elkahart, Ind., using methylbutane cooled with liquid nitrogen. After cutting 4 μM tissue sections with a cryostat, individual sections were subjected to various staining protocols. Briefly, sections mounted on glass slides were: 1) blocked with serum obtained from the species of fish, 2) incubated with rabbit anti-CaR antiserum and 3) washed and incubated with peroxidase conjugated affinity purified goat antirabbit antiserum. The locations of the bound peroxidase conjugated goat antirabbit antiserum was visualized by development of a rose colored aminoethylcarbazole reaction product. Individual sections were mounted, viewed and photographed by standard light microscopy techniques. The anti-CaR antiserum used to detect fish PVCR protein was raised in rabbits using a 23-mer peptide corresponding to amino acids numbers 214–236 localized in the extracellular domain of the RaKCaR protein.

Figure 1B:
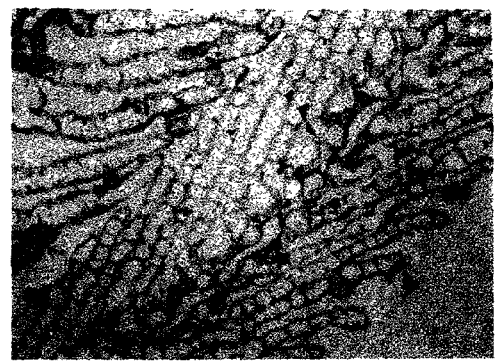
Figure 1C:
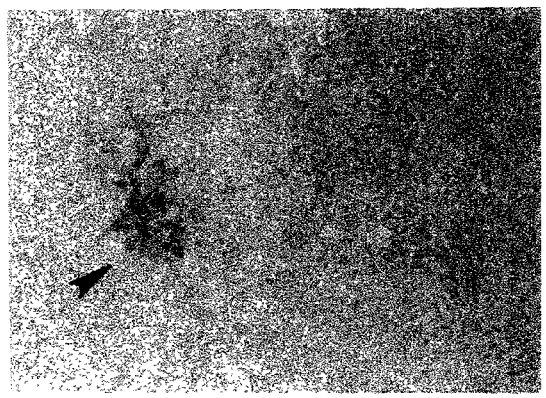
Figure 1D:
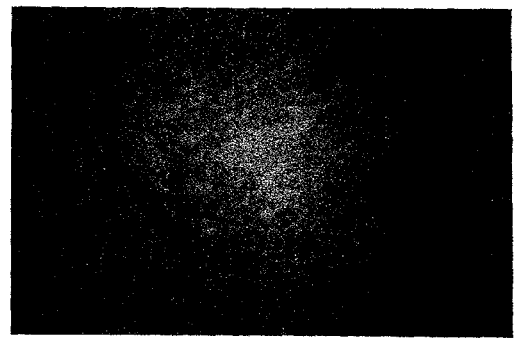
Figure 1E:
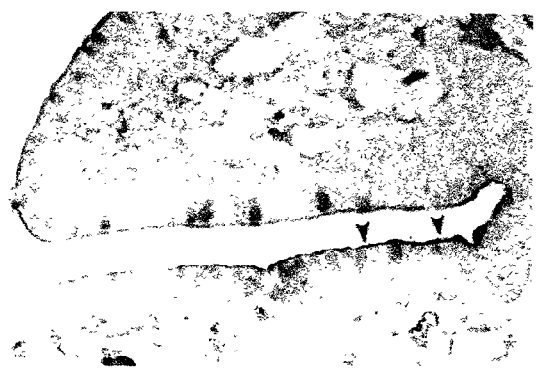
Figure 1F:
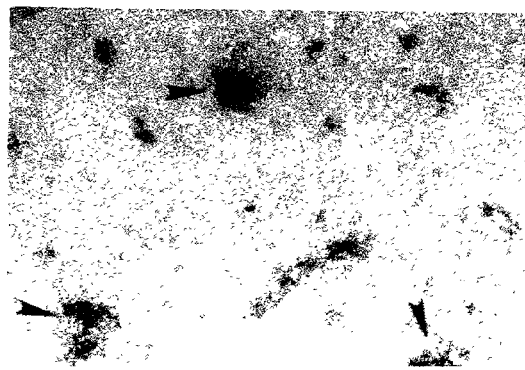

In both species of elasmobranchs studied, (dogfish shark, *Squatus Acanthias* and little skate, *Raja Erinacea*), PVCR protein was localized to the apical membranes of selected epithelial cells. The distribution of PVCR in elasmobranch tissue is shown in FIGS. 1A–F. Heavy black coloring is displayed where anti-CaR antibody binding is present consistently in areas of tissues designated by arrowheads. FIG. 1A: Kidney-CaR expression is present on apical membranes of epithelial cells of late distal tubule (LDT) and collecting duct (CD). FIG. 1B: Gill PVCR expression is localized to epithelial cells of gill arcades. FIG. 1C: Brain PVCR expression is localized to distinct groups of neurons in the brain. FIG. 1D: Rectal gland PVCR expression is localized to apical membranes of cells lining the ducts of the rectal gland. FIG. 1E: Intestine PVCR expression is localized to the apical membranes of epithelial cells lining the lumens of the intestine. FIG. 1F: Ovary PVCR expression is present in both oocytes and surrounding follicular cells.

FIGS. 2A–F show the distribution of PVCR in the flounder (*Pseudopleuronectes americanus*) and in the fresh water trout (*Onchorynchus Nerka*). FIGS. 2A–F display heavy black coloring where anti-CaR antibody binding is present consistently in areas of tissues designated by arrowheads. FIG. 2A: Kidney-CaR expression is present on apical membranes of epithelial cells of large tubules (LT) and collecting ducts (CD). FIG. 2B: Gill PVCR expression is localized to epithelial cells of gill arcades. FIG. 2C: Brain PVCR expression is localized to distinct groups of neurons in the brain. FIG. 2D: Urinary bladder PVCR expression is localized to apical membranes of cells lining the urinary bladder. FIG. 2E: Intestine PVCR expression is localized to the apical membranes of epithelial cells lining the lumens of the intestine. FIG. 2F: Ovary PVCR expression is present in both oocytes and surrounding follicular cells.

EXAMPLE 2

RNA Blotting Analyses of Winter Flounder Tissue

Figures 3A, 3B:
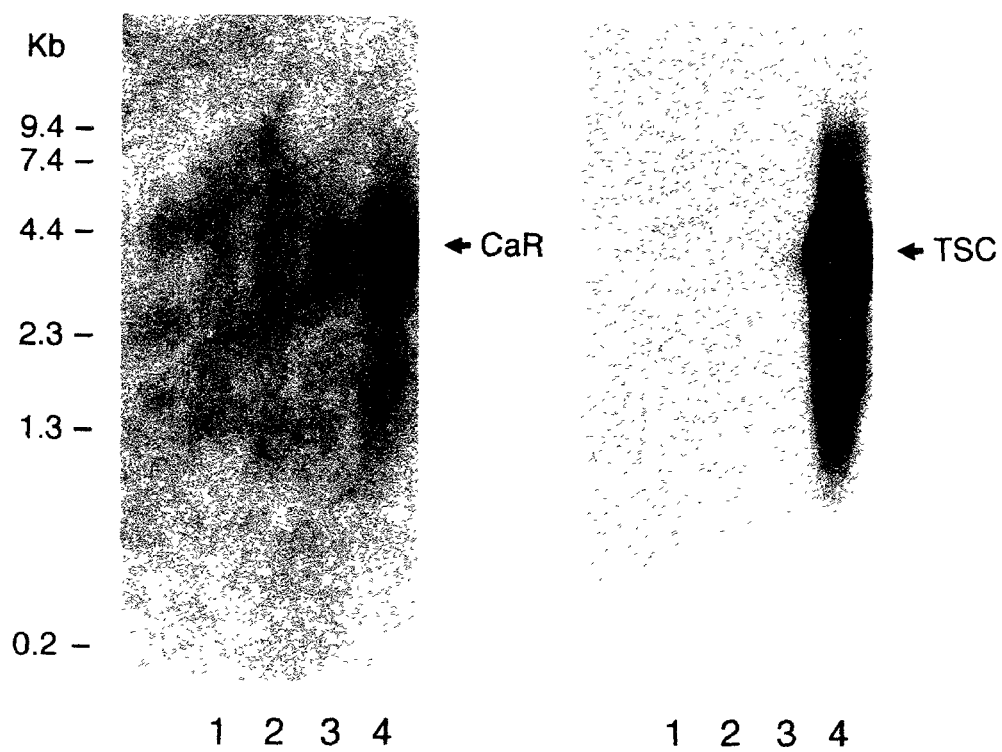
FIGS. 3A–B are audioradiograms showing RNA blotting analyses.

Five microgram samples of poly A+ RNA prepared from various winter flounder tissues including muscle (lane 1), heart (lane 2), testis (lane 3) and urinary bladder (lane 4) were subjected to RNA blotting analyses (FIGS. 3A and B).

As shown in FIG. 3A, a single filter was first hybridized using a $^{32}$P-labeled ECO R1/XHO 15' fragment of rat kidney PVCR cDNA (Brown, E. M., et al., *Nature*, 366:575 (1993)), washed at reduced stringency (1×SSC, 0.1% SDS, 50° C.) and exposed for 10 days to autoradiography.

As shown in FIG. 3B, the same filter shown in FIG. 3A after stripping and hybridization with a $^{32}$P-labeled full length 3.8 kb TSC cDNA that was washed at 0.5×SSC, 0.1% SDS at 65° C. and subjected to a 1 hour autoradiogram exposure. Data shown representative of a total of five separate experiments.

These data demonstrate the presence of a 4.4 kb homolog of the mammalian CaR present in poly A+ RNA from urinary bladder together with abundant 3.8 kb thiazidesensitive NaCl contransporter transcript, and suggest no PVCR transcripts are present in other tissues including muscle, heart or testis.

EXAMPLE 3

Molecular Cloning of Shark Kidney Calcuim Receptor Related Protein (SKCaR-RP)

A shark λZAP cDNA library was manufactured using standard commercially available reagents with cDNA synthesized from poly A+ RNA isolated from shark kidney tissue as described and published in Siner et al. *Am. J.*

Physiol. 270:C372–C381, 1996. The shark cDNA library was plated and resulting phage plaques screened using a $^{32}$plabeled full length rat kidney CaR (RaKCaR) cDNA probe under intermediate stringency conditions (0.5×SSC, 0.1% SDS, 50° C.). Individual positive plaques were identified by autoradiography, isolated and rescued using phagemid infections to transfer CDNA to KS Bluescript vector. The complete nucleotide sequence, FIGS. 4A–E, (SEQ ID NO: 1) of the 4.1 kb shark kidney PVCR related protein (SKCaR-RP) clone was obtained using commercially available automated sequencing service that performs nucleotide sequencing using the dideoxy chain termination technique. The deduced amino acid sequence (SEQ ID NO: 2) is shown in FIGS. 5A–E. Northern analyses were performed as described in Siner et. al. Am. J. Physiol. 270: C372–C381, 1996. The SKCAR-RP nucleotide sequence was compared to others CaRs using commercially available nucleotide and protein database services including GENBANK and SWISS PIR.

Polymerase chain reaction (PCR) amplification of selected cDNA sequences synthesized by reverse transcriptase (RT) were performed using a commercially available RT-PCR kit from Promega Biotech, Madison, Wis. Selective amplification of a conserved region of CaRs (nts 597–981 of RaKCaR cDNA) results in 384 nt cDNA, as shown in FIG. 7. This amplified 384 bp was then ligated into the TA cloning vector (Promega Biotech, Madison, Wis.) that was then transformed into competent DH5a *E. coli* cells using standard techniques. After purification of plasmid DNA using standard techniques the 384 nt cDNA was sequenced as described above.

EXAMPLE 4

PVCR Epression in Tissue of *Fundulus Herteroclitus*

To determine if PVCR expression was modulated by adaptation of Fundulus to either fresh or salt water, killifish collected in an estuary were first fresh or salt water adapted for an interval of 18 days (chronic adaptation). Selected individuals from each group were then adapted to the corresponding salinity (fresh to salt; salt to fresh) for an interval of 7 days (acute adaptation).

Figure 8:
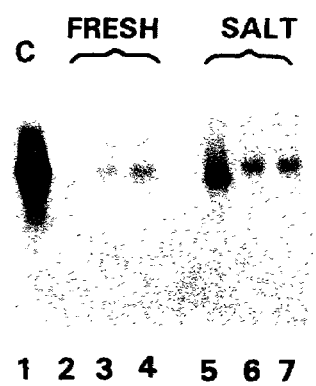
FIG. 8 is a photograph of immunocytochemistry results showing PVCR expression in selected tissues of Fundulus after 18 days of exposure to either sea or fresh water as determined by RNA blotting analysis.

Results are shown in FIG. 8. A blot containing RNA (40 ug/lane) prepared from control Xenopus kidney (lane 1) or Fundulus heart (containing ultimobranchial tissue) (lanes 2, 5), kidney (lanes 3, 6) and gill (lanes 4, 7) was probed with a 32p-labeled Xenopus PVCR cDNA, washed (0.01 ×SSC, 650C) and autoradiographed.

As shown in FIG. 8, as compared to control MRNA, (lane 1) steady state levels of PVCR MRNA are larger in tissues from seawater adapted fish (lanes 5–7) versus those in fresh water (lanes 2–4).

Figure 9A:
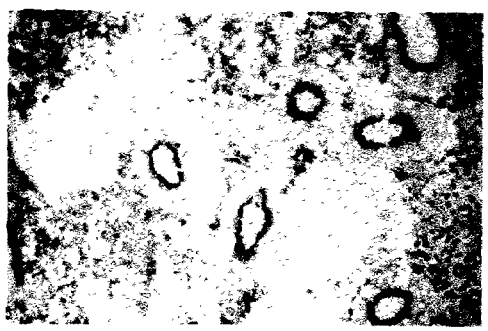
FIGS. 9A–D are photographs showing the results of immunocytochemistry analysis of PVCR expression in the kidney tubules of Fundulus fish either chronically (18 days) or acutely (7 days) adapted to either salt or fresh water.
Figure 9B:
Figure 9C:
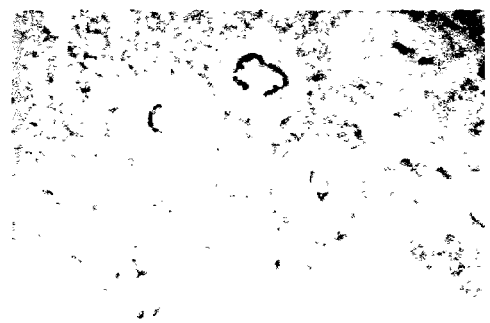
Figure 9D:

Fundulus fish were either chronically (FIGS. 9A and 9B) or acutely (FIGS. 9C and 9D) adapted to salt water (FIGS. 9A and 9C) or fresh water (FIGS. 9B and 9D). The presence of PVCR in kidney tubules was determined by immunocytochemistry. Chronic adaptation to salt water (9A) resulted in increased PVCR expression in kidney tubules as compared to that present in fresh (9B). Kidney tubule PVCR expression in salt water fish was diminished by acute adaptation to fresh water (9C). In contrast, kidney tubule PVCR expression in fresh water fish was increased after acute adaptation to salt water (9D).

EXAMPLE 5

Assay for PVCR Agonists and Antagonists Using the Flounder Urinary Bladder

To provide further evidence linking Aquatic PVCRs to fish osmoregulation, isolated urinary bladder of winter founder was used to investigate whether PVCRs modulate epithelial cell ion transport. Previous work has demonstrated that the flounder urinary bladder is important in osmoregulation since it allows recovery of both NaCl and water via a thiazide-sensitive NaCl contransport process that has been first generated by the kidney proximal tubule. Water reabsorption from the urine stored in urinary bladder allows for the concentrations of both $Mg^{2+}$ and $Ca^{2+}$ to increase to values as high as 84 mM and 7 mM respectively in marine founders (Elger, E. B., et al., *J. Como. Physiol.*, B157:21 (1987)). 5 Net apical to basolateral water flux (Jv) was measured gravimetrically in 10 minute intervals using individual urinary bladder excised from winter flounder. Briefly, isolated bladders were suspended in a liquid solution (typically a physiologically compatible solution) as described in (Renfro, L. J. Am. J. Physiol. 228:52–61, 1975) the teachings of which are hereby incorporated by reference. The weight of the bladder was measured before and after the experimental period, wherein the experimental period comprised the period of time that the isolated bladder was exposed to test compound. The compound to be tested (e.g., test compound) was added to both serosal and mucosal solutions. The bladders were dried and weighted as described in Renfro et al. The difference in bladder weight prior to and after exposure to test compound is an indication of water reabsorption by the bladder.

Quantification of water reabsorption (Jv) by isolated bladders using the method of Renfro et al. showed that Jv was significantly (p<0.05) inhibited by addition of 100 AM hydrochlorothiazide (86±2%) consistent with the role of the thiazide sensitive NaCl contransporter in this process. Urinary bladder iv was also significantly inhibited by PVCR agonists including 100 μM $Gd^{3+}$(75±5%) and 200 μM neomycin (52±4%). (Control Jv values (130±28 μl/gm/hr.) were obtained from animals in September–October and are approximately 21% of the Jv reported by Renfro et al. These differences likely reflect seasonal variations in urinary bladder transport.) The half maximal inhibitory concentration for urinary bladder Jv ($IC_{50}$) for $Gd^{3+}$ (15 μM) was similar to that reported for mammalian CaRs, while the $IC_{50}$ for neomycin (150 μM) was approximately 3 times larger as compared to mammalian CaRs (50 μM). This inhibitory effect of PVCR agonists on Jv was fully reversible. Activation of apical PVCRS by high concentrations of $Mg^{2+}$ and $Ca^{2+}$ resulting from NaCl-mediated water reabsorption from bladder urine would provide for optimal recovery of water by the urinary bladder. This mechanism would permit water reabsorption to proceed until divalent cation concentrations approach levels that promote crystal formation. This overall process is similar to that described for mammalian CaRs in the rat and human IMCD. Additional aspects of these mammalian and teleost renal epithelia may also share other similarities since teleost urinary bladder is both an anatomical and functional homolog of the mammalian mesonephric kidney.

EXAMPLE 6

Expression/Activation Studies of SKCaR in Human Embryonic Kidney (HEK) Cells The following studies show the following:
1. SKCaR nucleic acid sequence (SEQ ID NO.: 1) encodes a functional ion receptor that is sensitive to both Mg2+ and Ca2+ as well as alterations in NaCl.
2. SKCaR's (SEQ ID NO.: 2) sensitivity to Ca2+, Mg2+ and NaCl occur in the range that is found in marine environments and is consistent with SKCaRs role as a salinity sensor.
3. SKCaR's (SEQ ID NO.: 2) sensitivity to Mg2+ is further modulated by Ca2+ such that SKCaR is capable to sensing various combinations of divalent and monovalent cations in seawater and freshwater. These data can be used to design novel electrolyte solutions to maintain fish in salinities different from those present in their natural environment.

SKCaR cDNA (SEQ ID NO.: 1) was ligated into the mammalian expression vector PCDNA II and transfected into HEK cells using standard techniques. The presence of SKCaR protein (SEQ ID NO.: 2) in transfected cells was verified by western blotting. Activation of SKCaR (SEQ ID NO.: 2) by extracellular Ca2+, Mg2+ or NaCl was quantified using a well characterized FURA 2 based assay where increases in intracellular Ca2+ produced by SKCaR activation are detected using methodology published previously the Dr. E. Brown's laboratory (Bai, M., S. Quinn, S. Trvedi, O. Kifor, S. H. S. Pearce, M. R. Pollack, K. Krapcho, S. C. Hebert and E. M. Brown. Expression and characterization of inactivating and activating mutations in the human Ca2+-sensing receptor. J. Biol. Chem., 32:19537–19545 (1996)) and expressed as % normalized intracellular calcium response to receptor activation.

Figure 10:
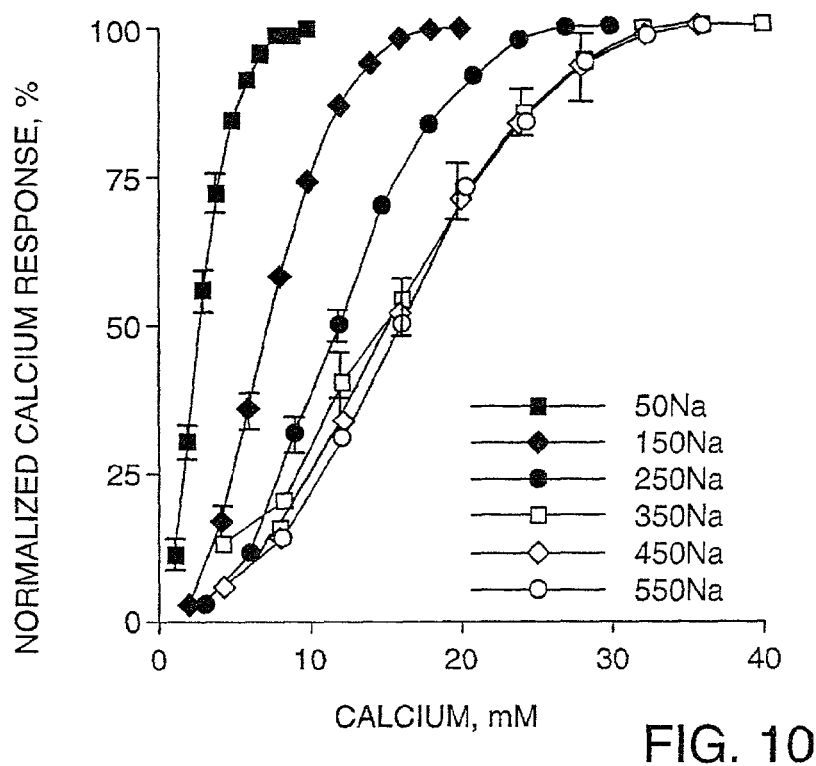
FIG. 10 is a graphical representation showing a normalized calcium response (%) against the amount of Calcium (mM) of the SKCaR-I protein when modulated by alternations in extracellular NaCl concentrations.

SKCaR (SEQ ID NO.: 2) is a functional extracellular Ca2+ sensor where its sensitivity is modulated by alterations in extracellular NaCl concentrations. As shown in FIG. 10, SKCaR (SEQ ID NO.: 2) is activated by increasing concentrations of extracellular Ca2+ where half maximal activation of SKCaR (SEQ ID NO.: 2) ranges between 1–15 mM depending on the extracellular concentration of NaCl. These are the exact ranges of Ca2+(1–10 mM present in marine estuarian areas). Note that increasing concentrations of NaCl reduce the sensitivity of SKCaR (SEQ ID NO.: 2) to Ca2+(see Panel B). This alteration in SKCaR (SEQ ID NO.: 2) sensitivity to Ca2+ was not observed after addition of an amount of sucrose sufficient to alter the osmolality of the extracellular medium. This control experiment shows it is not alterations in cell osmolality effecting the changes observed.

Figure 11:
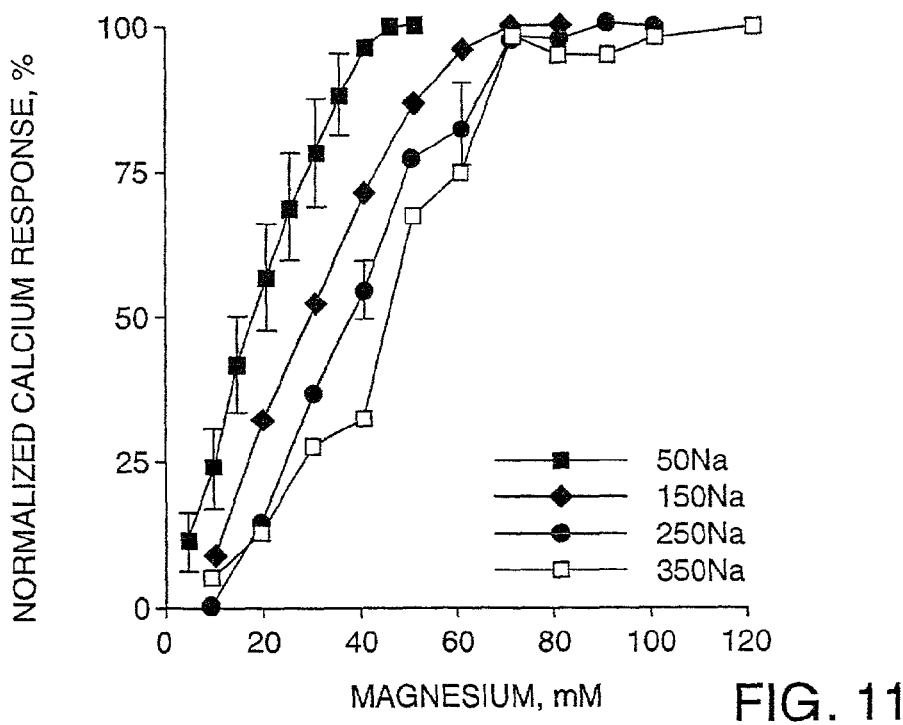
FIG. 11 is a graphical representation showing a normalized calcium response (%) against the amount of magnesium (mM) of the SKCaR-I protein in increasing amounts of extracellular NaCl concentrations.

The half maximal activation (EC50) by Ca2+ for SKCaR (SEQ ID NO.: 2) is reduced in increased concentrations of extracellular NaCl. See FIG. 11. The EC50 for data shown on FIG. 10 is displayed as a function of increasing extracellular NaCl concentrations. Note the EC50 for Ca2+ increases from less than 5 mM to approximately 18 mM as extracellular NaCl concentrations increase from 50 mM to 550 mM.

Figure 12:
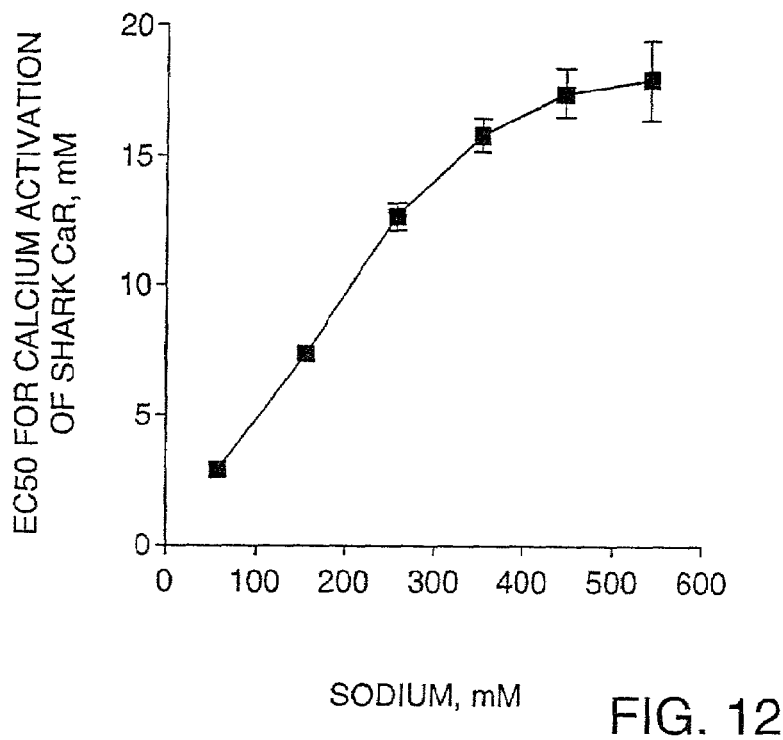
FIG. 12 is a graphical representation showing the EC50 for calcium activation of shark CaR (mM) against the amount of sodium (mM) of the SKCaR-I protein in increasing amounts of extracellular NaCl concentrations.

SKCaR (SEQ ID NO.: 2) is a functional extracellular Mg2+ sensor where its sensitivity is modulated by alterations in extracellular NaCl concentrations. As shown in FIG. 12, SKCaR (SEQ ID NO.: 2) is activated in the range of 5–40 mM extracellular Mg2 +and is modulated in a manner similar to that shown in FIGS. 10 and 11 by increasing concentrations of extracellular NaCl. Similarly, this alteration in SKCaR (SEQ ID NO.: 2) sensitivity to Ca2+ was not observed after addition of an amount of sucrose sufficient to alter the osmolality of the extracellular medium.

Figure 13:
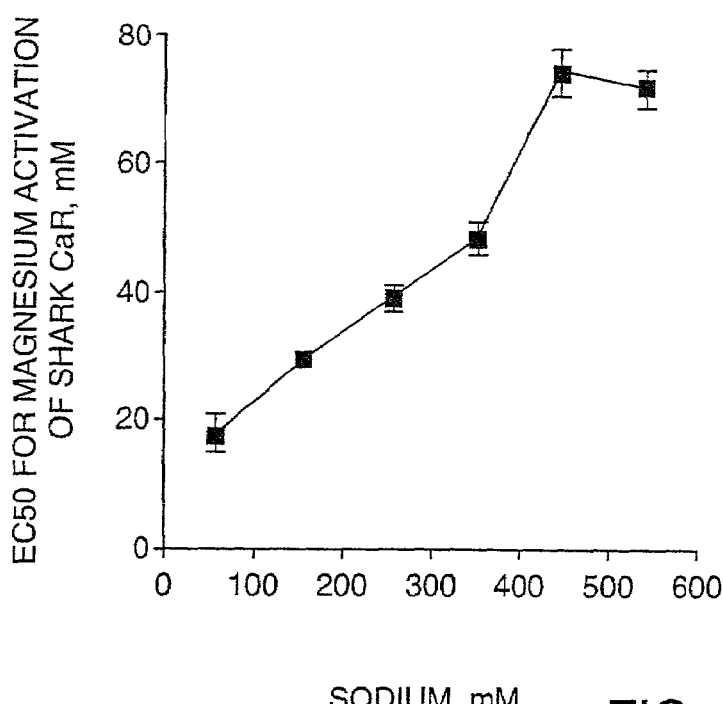
FIG. 13 is a graphical representation showing the EC50 for magnesium activation of shark CaR (mM) against the amount of sodium (mM) of the SKCaR-I protein in increasing amounts of extracellular NaCl concentrations.

The half maximal activation (EC50) by Mg2+ for SKCaR (SEQ ID NO.: 2) is reduced in increased concentrations of extracellular NaCl. See FIG. 13. The EC50 for data shown on FIG. 12 is displayed as a function of increasing extracellular NaCl concentrations. Note the EC50 for Mg2+ increases from less than 20 mM to approximately 80 mM as extracellular NaCl concentrations increase from 5 OmM to 550 mM.

Figure 14:
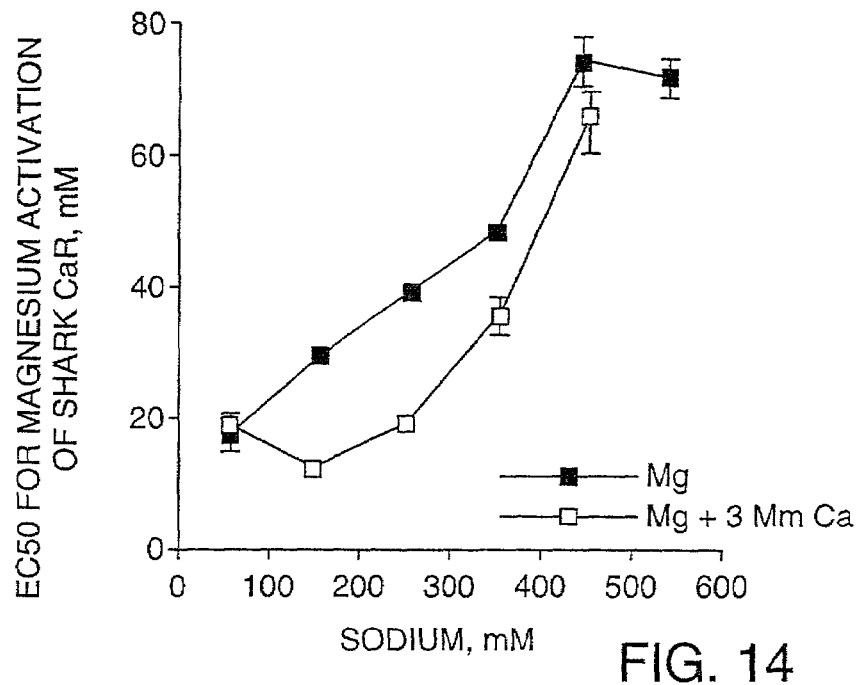
FIG. 14 is a graphical representation showing the EC50 for magnesium activation of shark CaR (mM) against the amount of sodium (mM) of the SKCaR-I protein in increasing amounts of extracellular NaCl concentrations and added amounts of calcium (3mM).

Addition of 3 mM Ca2+ alters the sensitivity of SKCaR (SEQ ID NO.: 2) to Mg2+ and NaCl. See FIG. 14. The EC50 for Mg2+ of SKCaR (SEQ ID NO.: 2) is modulated by increasing concentrations of NaCl as shown both in this FIG. 14 and in FIG. 13. Addition of 3 mM Ca2+ to the extracellular solution alters the sensitivity characteristics of SKCaR (SEQ ID NO.: 2) as shown. Note the 3 mM Ca2+ increases the sensitivity of SKCaR (SEQ ID NO.: 2) to Mg2+ as a function of extracellular NaCl concentrations.

EXAMPLE 7

Demonstration of the Presence of a Functional PVCR in Urinary Bladder of Winter Flunder.

Quantification of water reabsorption ($J_v$) in isolated bladders (ref. Renfro, J. L. *Water and ion transport by the urinary bladder of the teleost Pseudopleuronectes americanus. Am. J. Physiol.* 228:52–61 (1975) showed that control Jv (130±28 μl/gm/hr; n=14) was significantly (p<0.05) inhibited (86±2%) by addition of 100 μM hydrochlorothiazide (18±7 μl/gm/hr; n=6) consistent with the role of the thiazide-sensitive NaCl cotransporter in this process. Urinary bladder $J_v$ was also inhibited significantly by CaR agonists including 100 μM $Gd^{3+}$ (75±5% inhibition; 32±18 μl/gm/hr; n=5) and 200 μM neomycin (52±4% inhibition; 63±10 μl/gm/hr; n=5). The half maximal inhibitory concentration for urinary bladder $J_v$, ($IC_{50}$) for $Gd^{3+}$ (15±3 μM; n=6) was similar to that reported for mammalian CaRs (See Brown, E. M., G. Gamba, D. Riccardi, D. Lombardi, R. Butters, O. Kifor, A. Sun, M. Hediger, J. Lytton and S. C. Hebert. *Cloning and characterization of an extracellular $Ca^{2+}$ sensing receptor from bovine parathyroid. Nature* 366:575–580 (1993) while the neomycin $IC_{50}$(150±24 μM; n=6) was approximately 2–3 fold higher than for mammalian CaRs (60–70 μM) (Brown, E. M., G. E. -H. Fuleihan, C. J. Chen and O. Kifor. *A comparison of the effects of divalent and trivalent cations on parathyroid hormone release)* 3'5'-*cyclic-adenosine monophosphate accumulation and the levels of inositol phosphates in bovine parathyroid cells. Endocrinol.* 127:1064–1071 (1990).

Figure 15:
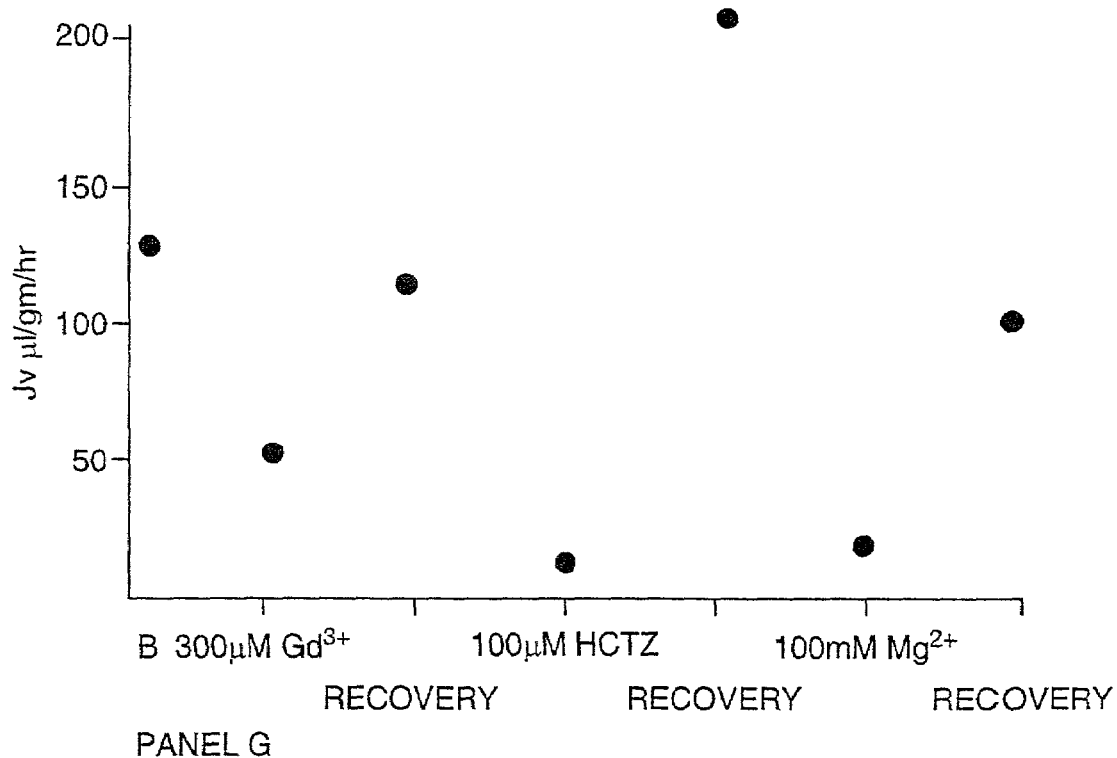
FIG. 15 is a graphical representation of water transport (Jv) against sequential exposures to Gd3+(300 µM), thiazide (100 µM) and magnesium (100 mM) and shows the response of a urinary bladder of winter flounder after exposure of its apical membrane to various CaR agonists and hydrochlorothiazide.

The maximal inhibitory effect for both CaR agonists on $J_v$, was fully reversible as shown in FIG. 15.

Response of a single isolated urinary bladder of winter flounder after exposure of its apical membrane to various CaR agonists and hydrochlorothiazide is shown in FIG. 15. Water transport (Jv) was measured in a single isolated urinary bladder after sequential exposures to 300 μM Gd3+, 100 mM thiazide and 100 mM Mg2+. Note that full recovery of water transport occurred after exposure to each of these agents. This data validates of the use of isolated urinary bladder as a screening assay.

EXAMPLE 8

Immunochemistry showing that PVCR Exists in Olfactory Organs

Additional immunocytochemistry experiments were performed using antibody 1169 (the antibody raised against the 23-mer peptide described herein) to localize SKCaR protein where it is present on the apical membrane of the lamellae of the olfactory organ epithelia of the dogfish shark (*Squalus ancanthias*). These data suggest that elasmobranchs possess the ability to "smell" salinity gradients in the marine environments. Furthermore, from this location SKCaR may interact with other odorant receptors that are also 7 transmembrane GTP binding protein receptors.

Figure 31A:
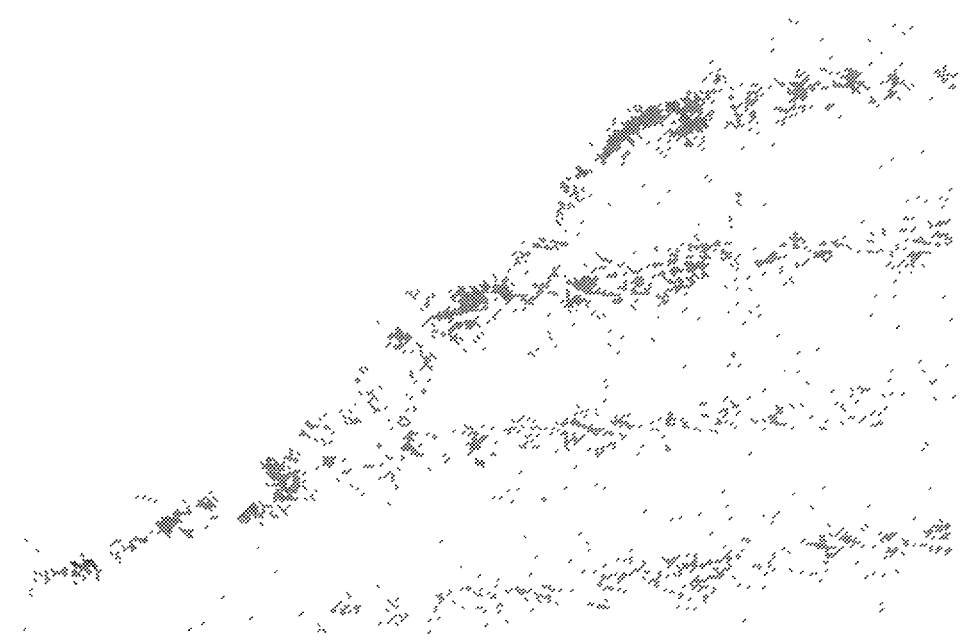
FIGS. 31A and B are photographs of immunochemistry of the lamellae of the olfactory organ epithelia of the dogfish shark using antisera 1169 and a control with no antisera 1169, respectively. The darker reaction product indicates specific 1169 antibody binding to the apical membrane of olfactory organ epithelial cells.
Figure 31B:
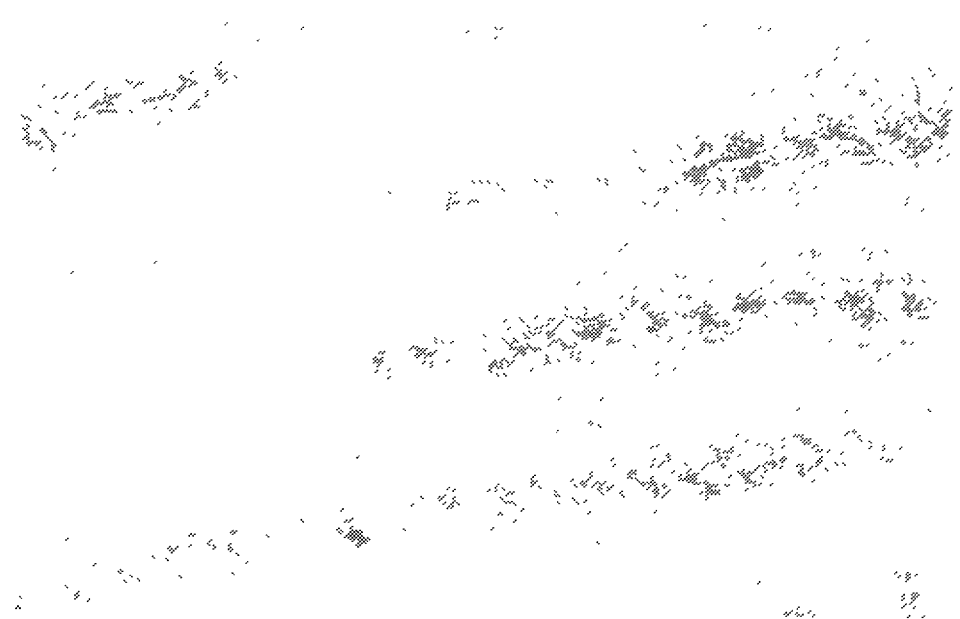

FIG. 31A shows the immunocytochemistry of the lamellae of the olfactory organ epithelia of the dogfish shark (*Squalus ancanthias*) using antisera 1169. Note the brown reaction product indicating specific 1169 antibody binding to the apical membrane of olfactory organ epithelial cells. FIG. 31B also is a photograph that shows lamellae that is not subject to antisera 1169, the control.

EXAMPLE 9

PVCRs Isolated in Various Aquatic Species

The PVCR has been isolated in several species including winter flounder (sole), summer flounder (fluke) and lumpfish (source of caviar). The PVCR has also been isolated in swordfish and lamprey. In addition, 2 sequences distinct from SKCaR-I have been obtained from shark indicating there are multiple polyvalent cation sensing receptors in a single species of fish.

Sequences of mammalian CaRs together with the nucleotide sequence of SKCaR (SEQ. ID NO: 1 and SEQ ID NO: 2) were used to design degenerate oligonucleotide primers to highly conserved regions in the extracellular domain of polyvalent cation receptor proteins using standard methodologies (See G M Preston, *Polymerase chain reaction with degenerate oligonucleotide primers to clone gene family members*, Methods in Mol. Biol. Vol. 58 Edited by A. Harwood, Humana Press, pages 303–312, 1993). Using these primers, cDNA or genomic DNA from various fish species representing important commercial products are amplified using standard PCR methodology. Amplified bands are then purified by agarose gel electrophoresis and ligated into appropriate plasmid vector that is transformed into a bacterial strain. After growth in liquid media, vectors and inserts are purified using standard techniques, analyzed by restriction enzyme analysis and sequenced where appropriate. Using this methodology, a total of 5 nucleotide sequences from 4 fish species were amplified.

Two additional nucleotide sequences were isolated from the Dogfish shark (*Squalus ancanthias*), same species as SKCaR-I (SEQ ID NO:2). Two nucleotide sequences, SEQ ID NO: 3 (FIGS. 16A–B) and SEQ ID NO: 5 (FIG. 19), were isolated from genomic SEQ ID NO: 3 or cDNA obtained from shark rectal gland (SEQ ID NO: 5). Both SEQ ID NOs: 3 and 5 are unique as compared to corresponding regions of the nucleotide sequence of SKCaR-I (SEQ ID NO: 1). SEQ ID NOs: 4 and 6 (FIGS. 17 and 20, respectively) represent the corresponding amino acids of putative open reading frames of SEQ ID NOs: 3 and 5. Thus, these 2 sequences represent at least 1 (different fragments of a single other gene) or possibly 2 calcium polyvalent cation sensing receptor proteins distinct from the SKCaR-I. FIG. 18 and FIG. 21 show the nucleotide sequences for SEQ ID NOs: 3 and 5, respectively, and the corresponding deduced amino acid sequences (SEQ ID NOs: 4 and 6, respectively).

SEQ ID NO: 3 is composed of 784 nucleotides (nt) containing an open reading frame coding for 261 amino acids. SEQ ID NO: 3 is similar, but not identical to the corresponding sequence in the extracellular domain of SKCaR I (SEQ ID NOs: 1 and 2) from nt. 1087–1836.

SEQ ID NO: 4 is composed of 261 Amino acids corresponding to the putative open reading for SEQ ID NO: 3.

SEQ ID NO: 5 is composed of 598 nucleotides (nt) containing an open reading frame coding for 198 amino acids and was obtained using oligonucleotide primers different from those used for SEQ ID NO: 3. SEQ ID NO: 5 is similar, but not identical to the corresponding sequence in the extracellular domain of SKCaR I (SEQ ID NOs: 1 and 2) from nt. 2279–2934.

SEQ ID NO: 6 comprises 198 Amino acids corresponding to the putative open reading for SEQ ID NO: 4.

Winter Flounder (*Pleuronectes americanus*) marine flatfish species was also isolated using the techniques described herein. SEQ ID NO: 7 was obtained from cDNA prepared from urinary bladder where functional data show presence of PVCR protein. SEQ ID NO: 8 corresponds to amino acids in the putative open reading frame of SEQ ID NO: 7.

SEQ ID NO: 7 is composed of 594 nucleotides (nt) containing an open reading frame coding for 197 amino acids. SEQ ID NO: 7 is homologous to the corresponding sequence in the extracellular domain of SKCaR I (SEQ ID NOs: 1 and 2) from nt. 2279–2937.

SEQ ID NO: 8 comprises the 197 Amino acids corresponding to the putative open reading frame of SEQ ID NO: 7.

Summer Flounder (*Paralichthus dentalus*) is another marine flatfish species that was isolated using methods, as described herein. SEQ ID NO: 9 was obtained from cDNA prepared from urinary bladder that is similar in function to the urinary bladder of winter flounder. SEQ ID NO: 10 contains amino acid corresponding to the putative open reading frame of SEQ ID NO: 9.

SEQ ID NO: 9 is composed of 475 nucleotides (nt) containing an open reading frame coding for 157 amino acids. SEQ ID NO: 9 is homologous to the corresponding sequence in the extracellular domain of SKCaR I (SEQ ID NOs: 1 and 2) from nt. 2279–2934.

SEQ ID NO: 10 has 157 Amino acids corresponding to the open reading frame for SEQ ID NO: 9.

Lumpfish (*Cyclopterus rumpus*) is an arctic marine fish that was isolated. Lumpfish is the sole source of lumpfish caviar. SEQ ID NO: 11 was obtained from cDNA prepared from the urinary bladder of lumpfish. SEQ ID NO: 12 is the corresponding amino acid sequence of the putative 435 amino acid open reading frame of SEQ ID NO: 11.

SEQ ID NO: 11 is composed of 1308 nts. that are homologous to the corresponding sequence in the extracellular domain of SKCaR I (SEQ ID NO: 1 and 2) from nt 1087–2441.

SEQ ID NO: 12 comprises the 435 Amino acids corresponding to the putative open reading frame for SEQ ID NO: 11.

| Primer sequences for PCR of PVCR clones: | | Sequences derived from the following SEQ ID NOs: |
|---|---|---|
| dSK-F1 5'-GCI GCT GAY GAY GAY TAY GG-3' | (SEQ ID NO.: 15) | 3, 11 |
| dSK-R2 5'-CCA IGC YTC IAG YTT YTT DAT RTC-3" | (SEQ ID NO.: 16) | 3 |
| dSK-F3 5'-TGT CKT GGA CGG AGC CCT TYG GRA TCG C-3' | (SEQ ID NO.: 17) | 5, 7, 9 |
| dSK-R3 5'-ATA GGC KGG RAT GAA RGA KAT CCA RAC RAT GAA G-3' | (SEQ ID NO.: 18) | 7 |
| dSK-R4 5'-GGC KGG RAT GAA RGA KAT CCA RAC RAT GAA G-3' | (SEQ ID NO.: 19) | 5, 9, 11 |

I = deoxyinosine, N = A + C + T + G, R = A + G, Y = C + T, M = A + C, K = T + G, S = C + G, W = A + T, H = A + T + C, B = T + C + G, D = A + T + G, V = A + C + G

EXAMPLE 10

Altering the Body Composition of Fish and Defining Salinity Limits

Winter and Summer Flounder can be grown and maintained in recycling water systems. Groups of both winter (*Pleuronectes americanus*) and summer (*Paralichthus dentalus*) flounder were maintained in multiple modular recycling water system units that are composed of a single 1 meter fish tank maintained by a 1 meter biofilter tank located directly above it. The upper tank of each unit contains 168 sq. ft. of biofilter surface area that will support a maximum of 31 lbs of flounder, while maintaining optimal water purity and oxygenation conditions. Each unit is equipped with its own pump and temperature regulator apparatus. Both the temperature and photoperiod of each unit can be independently regulated using black plastic curtains that partition each tank off from its neighbor. The inventors have a total of 12 independent modular units that permit 3 experiments each with 4 variables to be performed simultaneously. Using this experimental system, the following data have been obtained.

Salinity survival limits for winter and summer flounder with a constant ratio of divalent and monovalent ions were determined. The survival limit of both winter and summer flounder in waters of salinities greater than normal seawater (10 mM Ca2+, 50 mM Mg2+ and 450 mM NaCl) is water containing twice (20 mM Ca2+, 50 mM Mg2+ and 900 mM NaCl) the normal concentrations of ions present in normal seawater. In contrast, the survival limit of both winter and summer flounder in waters of salinity less than normal seawater is 10% seawater (1 mM Ca2+, 5 mM Mg2+ and 45 mM NaCl).

Flounder grown and/or maintained in low and hypersalinities possess different fat contents and taste as compared to flounder maintained in normal sea water. Use of a fully recycling water system permits growth of flounder at vastly different salinities. Groups of flounder (n=10) were adapted over a 15 day interval and maintained at either low salinity (LS) (e.g., at 10% normal seawater), normal seawater (NS) or hypersalinity (HS) (e.g., 2× seawater) for intervals of 3 months, under otherwise identical conditions. Survival among the 3 groups were comparable (all greater than 80%) and there were no differences in the electrolyte content of their respective sera. Analyses of fillet muscle from summer flounder for total fat, protein and moisture content are shown on Table I.

TABLE I

Comparison of Total Fat, Protein and Moisture Content of Muscle from Flounders Grown at Differing Water Salinities for 3 months. All values an average of 4 individual fish.

| Salinity | 10% Seawater | Normal Seawater | 2× Seawater |
|---|---|---|---|
| % Total Fat | 3.36 ± 0.43* | 2.59 ± 0.31* | 1.98 ± 0.66* |
| % Total Protein | 19.6 ± 0.23 | 19.9 ± 0.42 | 18.99 ± 0.34 |
| % Moisture | 74.7 ± 2.1 | 75.1 ± 1.8 | 73.8 ± 2.5 |

*Values significantly different from each other ($p < 0.05$).

Muscle from low salinity flounder contains approximately 30% higher fat content as compared to flounder maintained in normal seawater and approximately 70% greater fat content when compared to flounder maintained in 2× seawater (e.g., the fat of a flounder maintained in normal salinity is 40% greater than flounder maintained in twice seawater). These differences appear selective because no significant differences were observed in either muscle protein or moisture content.

Furthermore, fillets were sampled in a blinded protocol where tasters (n=6) were offered either raw or cooked fillets without knowledge of salinity conditions. Tasters could distinguish little difference between the taste of fillets of individual fish from each specific salinity group. However, when asked to compare fillets from flounder grown at differing salinities, a majority (⅚) clearly distinguished a taste difference between fillets from fish maintained at 10% salinity describing them as "sweet and buttery tasting with a soft consistency" as compared to fillets from fish maintained at either normal seawater or 2× seawater that were described as "wild and fishy tasting with a firmer consistency. These data provides evidence that "finishing" growth of winter flounder at different water salinities can be used to alter the taste and fat content of the resulting fillets in summer and winter flounder.

Groups of tagged hatchery raised summer flounder obtained from identical broodstock were exposed to either 10% seawater or 2× seawater for an interval of 3 months under conditions identical to that described above. There were no significant differences in either length or width in fish maintained 10% seawater or 2× seawater. However, there was a significant difference in the weights of the respective fish where 10% seawater fish weighted 80±14% (n=10) more than summer flounder maintained in 2× seawater. Moreover, the summer flounder maintained in 10% seawater were nearly twice (2.1±0.4 times n=6) as thick as compared to fish maintained in 2× seawater. These data show that flounder maintained at different water salinities exhibit significant differences in the thickness of their fillets. Thus, flounder could be "finished" using water of differing compositions to alter the thickness of their fillets.

Equivalents

Those skilled in the art will recognize, or be able to ascertain using no more than routine experimentation, many equivalents to specific embodiments of the invention described specifically herein. Such equivalents are intended to be encompassed in the scope of the following claims.

---

SEQUENCE LISTING

<160> NUMBER OF SEQ ID NOS: 19

<210> SEQ ID NO 1
<211> LENGTH: 4134
<212> TYPE: DNA
<213> ORGANISM: squalas acanthias
<220> FEATURE:
<221> NAME/KEY: CDS
<222> LOCATION: (439)...(3522)

<400> SEQUENCE: 1

```
aattccgttg ctgtcggttc agtccaagtc tcctccagtg caaaatgaga aatggtggtc      60
gccattacag gaacatgcac tacatctgtg ttaatgaaat attgtcagtt atctgaaggt     120
tattaaaatg tttctgcaag gatggcttca cgagaaatca attctgcacg tttttcccatt    180 gtcattgtat gaataactga ccaaagggat gtaacaaaat ggaacaaagc tgaggaccac     240
gttcacccct tcttggagca tacgatcaac cctgaaggag atggaagact tgaggaggaa     300
atggggattg atcttccagg agttctgctg taaagcgatc cctcaccatt acaaagataa     360
gcagaaatcc tccaggcatc ctctgtaaac gggctggcgt agtgtggctt ggtcaaggaa     420
cagagacagg gctgcaca atg gct cag ctt cac tgc caa ctc tta ttc ttg       471
                    Met Ala Gln Leu His Cys Gln Leu Leu Phe Leu
                     1               5                  10 gga ttt aca ctc cta cag tcg tac aat gtc tca ggg tat ggt cca aac       519
Gly Phe Thr Leu Leu Gln Ser Tyr Asn Val Ser Gly Tyr Gly Pro Asn
             15                  20                  25 caa agg gcc cag aag aaa gga gac atc ata ctg gga ggt ctc ttc cca       567
Gln Arg Ala Gln Lys Lys Gly Asp Ile Ile Leu Gly Gly Leu Phe Pro
         30                  35                  40 ata cac ttt gga gta gcc gcc aag gat cag gac tta aaa tcg aga ccg       615
Ile His Phe Gly Val Ala Ala Lys Asp Gln Asp Leu Lys Ser Arg Pro
     45                  50                  55 gag gcg aca aaa tgt att cgg tac aat ttt cga ggc ttc cga tgg ctc       663
Glu Ala Thr Lys Cys Ile Arg Tyr Asn Phe Arg Gly Phe Arg Trp Leu
 60                  65                  70                  75 cag gcg atg ata ttc gca att gaa gag att aac aac agt atg act ttc       711
Gln Ala Met Ile Phe Ala Ile Glu Glu Ile Asn Asn Ser Met Thr Phe
                 80                  85                  90 ctg ccc aat atc acc ctg gga tat cgc ata ttt gac acg tgt aac acc       759
Leu Pro Asn Ile Thr Leu Gly Tyr Arg Ile Phe Asp Thr Cys Asn Thr
             95                 100                 105 gtg tcc aag gcg cta gag gca aca ctc agc ttt gtg gcc cag aac aaa       807
Val Ser Lys Ala Leu Glu Ala Thr Leu Ser Phe Val Ala Gln Asn Lys
        110                 115                 120 atc gac tcg ctg aac tta gat gag ttc tgt aac tgc tct gac cat atc       855
Ile Asp Ser Leu Asn Leu Asp Glu Phe Cys Asn Cys Ser Asp His Ile
    125                 130                 135 cca tcc aca ata gca gtg gtc ggg gca acc ggg tca gga atc tcc acg       903
Pro Ser Thr Ile Ala Val Val Gly Ala Thr Gly Ser Gly Ile Ser Thr
140                 145                 150                 155 gct gtg gcc aat cta ttg gga tta ttt tac att cca cag gtc agc tat       951
```

```
            Ala Val Ala Asn Leu Leu Gly Leu Phe Tyr Ile Pro Gln Val Ser Tyr
                            160                 165                 170 gcc tcc tcg agc agg ctg ctc agc aac aag aat gag tac aag gcc ttc         999
Ala Ser Ser Ser Arg Leu Leu Ser Asn Lys Asn Glu Tyr Lys Ala Phe
                175                 180                 185 ctg agg acc atc ccc aat gat gag caa cag gcc acg gcc atg gcc gag        1047
Leu Arg Thr Ile Pro Asn Asp Glu Gln Gln Ala Thr Ala Met Ala Glu
            190                 195                 200 atc atc gag cac ttc cag tgg aac tgg gtg gga acc ctg gca gcc gac        1095
Ile Ile Glu His Phe Gln Trp Asn Trp Val Gly Thr Leu Ala Ala Asp
        205                 210                 215 gat gac tat ggc cgc cca ggc att gac aag ttc cgg gag gag gcc gtt        1143
Asp Asp Tyr Gly Arg Pro Gly Ile Asp Lys Phe Arg Glu Glu Ala Val
220                 225                 230                 235 aag agg gac atc tgt att gac ttc agt gag atg atc tct cag tac tac        1191
Lys Arg Asp Ile Cys Ile Asp Phe Ser Glu Met Ile Ser Gln Tyr Tyr
                240                 245                 250 acc cag aag cag ttg gag ttc atc gcc gac gtc atc cag aac tcc tcg        1239
Thr Gln Lys Gln Leu Glu Phe Ile Ala Asp Val Ile Gln Asn Ser Ser
            255                 260                 265 gcc aag gtc atc gtg gtc ttc tcc aat ggc ccc gac ctg gag ccg ctc        1287
Ala Lys Val Ile Val Val Phe Ser Asn Gly Pro Asp Leu Glu Pro Leu
        270                 275                 280 atc cag gag ata gtt cgg aga aac atc acc gat cgg atc tgg ctg gcc        1335
Ile Gln Glu Ile Val Arg Arg Asn Ile Thr Asp Arg Ile Trp Leu Ala
285                 290                 295 agc gag gct tgg gcc agc tct tcg ctc att gcc aag cca gag tac ttc        1383
Ser Glu Ala Trp Ala Ser Ser Ser Leu Ile Ala Lys Pro Glu Tyr Phe
300                 305                 310                 315 cac gtg gtc ggc ggc acc atc ggc ttc gct ctc agg gcg ggg cgt atc        1431
His Val Val Gly Gly Thr Ile Gly Phe Ala Leu Arg Ala Gly Arg Ile
                320                 325                 330 cca ggg ttc aac aag ttc ctg aag gag gtc cac ccc agc agg tcc tcg        1479
Pro Gly Phe Asn Lys Phe Leu Lys Glu Val His Pro Ser Arg Ser Ser
            335                 340                 345 gac aat ggg ttt gtc aag gag ttc tgg gag gag acc ttc aac tgc tac        1527
Asp Asn Gly Phe Val Lys Glu Phe Trp Glu Glu Thr Phe Asn Cys Tyr
        350                 355                 360 ttc acc gag aag acc ctg acg cag ctg aag aat tcc aag gtg ccc tcg        1575
Phe Thr Glu Lys Thr Leu Thr Gln Leu Lys Asn Ser Lys Val Pro Ser
365                 370                 375 cac gga ccg gcg gct caa ggg gac ggc tcc aag gcg ggg aac tcc aga        1623
His Gly Pro Ala Ala Gln Gly Asp Gly Ser Lys Ala Gly Asn Ser Arg
380                 385                 390                 395 cgg aca gcc cta cgc cac ccc tgc act ggg gag gag aac atc acc agc        1671
Arg Thr Ala Leu Arg His Pro Cys Thr Gly Glu Glu Asn Ile Thr Ser
                400                 405                 410 gtg gag acc ccc tac ctg gat tat aca cac ctg agg atc tcc tac aat        1719
Val Glu Thr Pro Tyr Leu Asp Tyr Thr His Leu Arg Ile Ser Tyr Asn
            415                 420                 425 gta tac gtg gcc gtc tac tcc att gct cac gcc ctg caa gac atc cac        1767
Val Tyr Val Ala Val Tyr Ser Ile Ala His Ala Leu Gln Asp Ile His
        430                 435                 440 tct tgc aaa ccc ggc acg ggc atc ttt gca aac gga tct tgt gca gat        1815
Ser Cys Lys Pro Gly Thr Gly Ile Phe Ala Asn Gly Ser Cys Ala Asp
445                 450                 455 att aaa aaa gtt gag gcc tgg cag gtc ctc aac cat ctg ctg cat ctg        1863
Ile Lys Lys Val Glu Ala Trp Gln Val Leu Asn His Leu Leu His Leu
460                 465                 470                 475
```

```
aag ttt acc aac agc atg ggt gag cag gtt gac ttt gac gat caa ggt         1911
Lys Phe Thr Asn Ser Met Gly Glu Gln Val Asp Phe Asp Asp Gln Gly
                480                 485                 490 gac ctc aag ggg aac tac acc att atc aac tgg cag ctc tcc gca gag         1959
Asp Leu Lys Gly Asn Tyr Thr Ile Ile Asn Trp Gln Leu Ser Ala Glu
            495                 500                 505 gat gaa tcg gtg ttg ttc cat gag gtg ggc aac tac aac gcc tac gct         2007
Asp Glu Ser Val Leu Phe His Glu Val Gly Asn Tyr Asn Ala Tyr Ala
        510                 515                 520 aag ccc agt gac cga ctc aac atc aac gaa aag aaa atc ctc tgg agt         2055
Lys Pro Ser Asp Arg Leu Asn Ile Asn Glu Lys Lys Ile Leu Trp Ser
    525                 530                 535 ggc ttc tcc aaa gtg gtt cct ttc tcc aac tgc agt cga gac tgt gtg         2103
Gly Phe Ser Lys Val Val Pro Phe Ser Asn Cys Ser Arg Asp Cys Val
540                 545                 550                 555 ccg ggc acc agg aag ggg atc atc gag ggg gag ccc acc tgc tgc ttt         2151
Pro Gly Thr Arg Lys Gly Ile Ile Glu Gly Glu Pro Thr Cys Cys Phe
                560                 565                 570 gaa tgc atg gca tgt gca gag gga gag ttc agt gat gaa aac gat gca         2199
Glu Cys Met Ala Cys Ala Glu Gly Glu Phe Ser Asp Glu Asn Asp Ala
            575                 580                 585 agt gcg tgt aca aag tgc ccg aat gat ttc tgg tcg aat gag aac cac         2247
Ser Ala Cys Thr Lys Cys Pro Asn Asp Phe Trp Ser Asn Glu Asn His
        590                 595                 600 acg tcg tgc atc gcc aag gag atc gag tac ctg tcg tgg acg gag ccc         2295
Thr Ser Cys Ile Ala Lys Glu Ile Glu Tyr Leu Ser Trp Thr Glu Pro
    605                 610                 615 ttc ggg atc gct ctg acc atc ttc gcc gta ctg ggc atc ctg atc acc         2343
Phe Gly Ile Ala Leu Thr Ile Phe Ala Val Leu Gly Ile Leu Ile Thr
620                 625                 630                 635 tcc ttc gtg ctg ggg gtc ttc atc aag ttc agg aac act ccc atc gtg         2391
Ser Phe Val Leu Gly Val Phe Ile Lys Phe Arg Asn Thr Pro Ile Val
                640                 645                 650 aag gcc acc aac cgg gag ttg tcc tac ctg ctg ctc ttc tcc ctc atc         2439
Lys Ala Thr Asn Arg Glu Leu Ser Tyr Leu Leu Leu Phe Ser Leu Ile
            655                 660                 665 tgc tgc ttc tcc agc tcg ctc atc ttc atc ggc gag ccc agg gac tgg         2487
Cys Cys Phe Ser Ser Ser Leu Ile Phe Ile Gly Glu Pro Arg Asp Trp
        670                 675                 680 acc tgt cgg ctc cgc caa ccg gcc ttt ggc atc agc ttc gtc ctg tgc         2535
Thr Cys Arg Leu Arg Gln Pro Ala Phe Gly Ile Ser Phe Val Leu Cys
    685                 690                 695 atc tcc tgc atc ctg gtg aag acc aac cgg gtg ctg ctg gtc ttc gag         2583
Ile Ser Cys Ile Leu Val Lys Thr Asn Arg Val Leu Leu Val Phe Glu
700                 705                 710                 715 gcc aag atc ccc acc agc ctc cac cgc aag tgg gtg ggc ctc aac ctg         2631
Ala Lys Ile Pro Thr Ser Leu His Arg Lys Trp Val Gly Leu Asn Leu
                720                 725                 730 cag ttc ctc ctg gtc ttc ctc tgc atc ctg gtg caa atc gtc acc tgc         2679
Gln Phe Leu Leu Val Phe Leu Cys Ile Leu Val Gln Ile Val Thr Cys
            735                 740                 745 atc atc tgg ctc tac acc gcg cct ccc tcc agc tac agg aac cat gag         2727
Ile Ile Trp Leu Tyr Thr Ala Pro Pro Ser Ser Tyr Arg Asn His Glu
        750                 755                 760 ctg gag gac gag gtc atc ttc atc acc tgc gac gag ggc tcg ctc atg         2775
Leu Glu Asp Glu Val Ile Phe Ile Thr Cys Asp Glu Gly Ser Leu Met
    765                 770                 775 gcg ctg ggc ttc ctc atc ggc tac acc tgc ctc ctc gcc gcc atc tgc         2823
Ala Leu Gly Phe Leu Ile Gly Tyr Thr Cys Leu Leu Ala Ala Ile Cys
780                 785                 790                 795
```

```
                                                                              -continued ttc ttc ttc gcc ttc aag tcc cgt aag ctg ccg gag aac ttc aac gag      2871
Phe Phe Phe Ala Phe Lys Ser Arg Lys Leu Pro Glu Asn Phe Asn Glu
            800                 805                 810 gct aag ttc atc acc ttc agc atg ttg atc ttc ttc atc gtc tgg atc      2919
Ala Lys Phe Ile Thr Phe Ser Met Leu Ile Phe Phe Ile Val Trp Ile
        815                 820                 825 tcc ttc atc ccc gcc tat gtc agc acc tac ggc aag ttt gtg tcg gcc      2967
Ser Phe Ile Pro Ala Tyr Val Ser Thr Tyr Gly Lys Phe Val Ser Ala
            830                 835                 840 gtg gag gtg att gcc atc ctg gcc tcc agc ttc ggg ctg ctg ggc tgc      3015
Val Glu Val Ile Ala Ile Leu Ala Ser Ser Phe Gly Leu Leu Gly Cys
        845                 850                 855 att tac ttc aac aag tgt tac atc atc ctg ttc aag ccg tgc cgt aac      3063
Ile Tyr Phe Asn Lys Cys Tyr Ile Ile Leu Phe Lys Pro Cys Arg Asn
860                 865                 870                 875 acc atc gag gag gtg cgc tgc agc acg gcg gcc cac gcc ttc aag gtg      3111
Thr Ile Glu Glu Val Arg Cys Ser Thr Ala Ala His Ala Phe Lys Val
                880                 885                 890 gcg gcc cgg gcc acc ctc cgg cgc agc gcc gcg tct cgc aag cgc tcc      3159
Ala Ala Arg Ala Thr Leu Arg Arg Ser Ala Ala Ser Arg Lys Arg Ser
        895                 900                 905 agc agc ctg tgc ggc tcc acc atc tcc tcg ccc gcc tcg tcc acc tgc      3207
Ser Ser Leu Cys Gly Ser Thr Ile Ser Ser Pro Ala Ser Ser Thr Cys
            910                 915                 920 ggg ccg ggc ctc acc atg gag atg cag cgc tgc agc acg cag aag gtc      3255
Gly Pro Gly Leu Thr Met Glu Met Gln Arg Cys Ser Thr Gln Lys Val
        925                 930                 935 agc ttc ggc agc ggc acc gtc acc ctg tcg ctc agc ttc gag gag aca      3303
Ser Phe Gly Ser Gly Thr Val Thr Leu Ser Leu Ser Phe Glu Glu Thr
940                 945                 950                 955 ggc cga tac gcc acc ctc agc cgc acg gcc cgc agc agg aac tcg gcg      3351
Gly Arg Tyr Ala Thr Leu Ser Arg Thr Ala Arg Ser Arg Asn Ser Ala
                960                 965                 970 gat ggc cgc agc ggc gac gac ctg cca tct aga cac cac gac cag ggc      3399
Asp Gly Arg Ser Gly Asp Asp Leu Pro Ser Arg His His Asp Gln Gly
        975                 980                 985 ccg cct cag aaa tgc gag ccc cag ccc gcc aac gat gcc cga tac aag      3447
Pro Pro Gln Lys Cys Glu Pro Gln Pro Ala Asn Asp Ala Arg Tyr Lys
            990                 995                 1000 gcg gcg ccg acc aag ggc acc cta gag tcg ccg ggc ggc agc aag gag      3495
Ala Ala Pro Thr Lys Gly Thr Leu Glu Ser Pro Gly Gly Ser Lys Glu
        1005                1010                1015 cgc ccc aca act atg gag gaa acc taa tccaactcct ccatcaaccc            3542
Arg Pro Thr Thr Met Glu Glu Thr  *
1020                1025 caagaacatc ctccacggca gcaccgtcga caactgacat caactcctaa ccggtggctg    3602
cccaacctct cccctctccg gcactttgcg ttttgctgaa gattgcagca tctgcagttc    3662
cttttatccc tgatttcctg acttggatat ttactagtgt gcgatggaat atcacaacat    3722
aatgagttgc acaattaggt gagcagagtt gtgtcaaagt atctgaacta tctgaagtat    3782
ctgaactact ttattctctc gaattgtatt acaaacattt gaagtatttt tagtgacatt    3842
atgttctaac attgtcaaga taatttgtta caacatataa ggtaccccct gaagcagtga    3902
ctgagattgc cactgtgatg acagaactgt tttataacat ttatcattga aacctggatt    3962
gcaacaggaa tataatgact gtaacaaaaa aattgttgat tatcttaaaa atgcaaattg    4022
taatcagatg tgtaaaattg gtaattactt ctgtacatta aatgcatatt tcttgataaa    4082
```

```
aaaaaaaaaa aaaaaaaaaa aaaaaaaaaa aaaagcggcc cgacagcaac gg         4134
```

<210> SEQ ID NO 2
<211> LENGTH: 1027
<212> TYPE: PRT
<213> ORGANISM: squalus acanthias

<400> SEQUENCE: 2

```
Met Ala Gln Leu His Cys Gln Leu Leu Phe Leu Gly Phe Thr Leu Leu
 1               5                  10                  15

Gln Ser Tyr Asn Val Ser Gly Tyr Gly Pro Asn Gln Arg Ala Gln Lys
             20                  25                  30

Lys Gly Asp Ile Ile Leu Gly Gly Leu Phe Pro Ile His Phe Gly Val
         35                  40                  45

Ala Ala Lys Asp Gln Asp Leu Lys Ser Arg Pro Glu Ala Thr Lys Cys
     50                  55                  60

Ile Arg Tyr Asn Phe Arg Gly Phe Arg Trp Leu Gln Ala Met Ile Phe
 65                  70                  75                  80

Ala Ile Glu Glu Ile Asn Asn Ser Met Thr Phe Leu Pro Asn Ile Thr
                 85                  90                  95

Leu Gly Tyr Arg Ile Phe Asp Thr Cys Asn Thr Val Ser Lys Ala Leu
            100                 105                 110

Glu Ala Thr Leu Ser Phe Val Ala Gln Asn Lys Ile Asp Ser Leu Asn
        115                 120                 125

Leu Asp Glu Phe Cys Asn Cys Ser Asp His Ile Pro Ser Thr Ile Ala
    130                 135                 140

Val Val Gly Ala Thr Gly Ser Gly Ile Ser Thr Ala Val Ala Asn Leu
145                 150                 155                 160

Leu Gly Leu Phe Tyr Ile Pro Gln Val Ser Tyr Ala Ser Ser Ser Arg
                165                 170                 175

Leu Leu Ser Asn Lys Asn Glu Tyr Lys Ala Phe Leu Arg Thr Ile Pro
            180                 185                 190

Asn Asp Glu Gln Gln Ala Thr Ala Met Ala Glu Ile Ile Glu His Phe
        195                 200                 205

Gln Trp Asn Trp Val Gly Thr Leu Ala Ala Asp Asp Tyr Gly Arg
    210                 215                 220

Pro Gly Ile Asp Lys Phe Arg Glu Glu Ala Val Lys Arg Asp Ile Cys
225                 230                 235                 240

Ile Asp Phe Ser Glu Met Ile Ser Gln Tyr Tyr Thr Gln Lys Gln Leu
                245                 250                 255

Glu Phe Ile Ala Asp Val Ile Gln Asn Ser Ser Ala Lys Val Ile Val
            260                 265                 270

Val Phe Ser Asn Gly Pro Asp Leu Glu Pro Leu Ile Gln Glu Ile Val
        275                 280                 285

Arg Arg Asn Ile Thr Asp Arg Ile Trp Leu Ala Ser Glu Ala Trp Ala
    290                 295                 300

Ser Ser Ser Leu Ile Ala Lys Pro Glu Tyr Phe His Val Val Gly Gly
305                 310                 315                 320

Thr Ile Gly Phe Ala Leu Arg Ala Gly Arg Ile Pro Gly Phe Asn Lys
                325                 330                 335

Phe Leu Lys Glu Val His Pro Ser Arg Ser Ser Asp Asn Gly Phe Val
            340                 345                 350

Lys Glu Phe Trp Glu Glu Thr Phe Asn Cys Tyr Phe Thr Glu Lys Thr
        355                 360                 365
```

-continued

Leu Thr Gln Leu Lys Asn Ser Lys Val Pro Ser His Gly Pro Ala Ala
    370             375             380

Gln Gly Asp Gly Ser Lys Ala Gly Asn Ser Arg Arg Thr Ala Leu Arg
385             390             395             400

His Pro Cys Thr Gly Glu Glu Asn Ile Thr Ser Val Glu Thr Pro Tyr
                405             410             415

Leu Asp Tyr Thr His Leu Arg Ile Ser Tyr Asn Val Tyr Val Ala Val
            420             425             430

Tyr Ser Ile Ala His Ala Leu Gln Asp Ile His Ser Cys Lys Pro Gly
        435             440             445

Thr Gly Ile Phe Ala Asn Gly Ser Cys Ala Asp Ile Lys Lys Val Glu
    450             455             460

Ala Trp Gln Val Leu Asn His Leu Leu His Leu Lys Phe Thr Asn Ser
465             470             475             480

Met Gly Glu Gln Val Asp Phe Asp Asp Gln Gly Asp Leu Lys Gly Asn
                485             490             495

Tyr Thr Ile Ile Asn Trp Gln Leu Ser Ala Glu Asp Glu Ser Val Leu
            500             505             510

Phe His Glu Val Gly Asn Tyr Asn Ala Tyr Ala Lys Pro Ser Asp Arg
        515             520             525

Leu Asn Ile Asn Glu Lys Lys Ile Leu Trp Ser Gly Phe Ser Lys Val
530             535             540

Val Pro Phe Ser Asn Cys Ser Arg Asp Cys Val Pro Gly Thr Arg Lys
545             550             555             560

Gly Ile Ile Glu Gly Glu Pro Thr Cys Cys Phe Glu Cys Met Ala Cys
                565             570             575

Ala Glu Gly Glu Phe Ser Asp Glu Asn Asp Ala Ser Ala Cys Thr Lys
            580             585             590

Cys Pro Asn Asp Phe Trp Ser Asn Glu Asn His Thr Ser Cys Ile Ala
        595             600             605

Lys Glu Ile Glu Tyr Leu Ser Trp Thr Glu Pro Phe Gly Ile Ala Leu
610             615             620

Thr Ile Phe Ala Val Leu Gly Ile Leu Ile Thr Ser Phe Val Leu Gly
625             630             635             640

Val Phe Ile Lys Phe Arg Asn Thr Pro Ile Val Lys Ala Thr Asn Arg
                645             650             655

Glu Leu Ser Tyr Leu Leu Leu Phe Ser Leu Ile Cys Cys Phe Ser Ser
            660             665             670

Ser Leu Ile Phe Ile Gly Glu Pro Arg Asp Trp Thr Cys Arg Leu Arg
        675             680             685

Gln Pro Ala Phe Gly Ile Ser Phe Val Leu Cys Ile Ser Cys Ile Leu
690             695             700

Val Lys Thr Asn Arg Val Leu Leu Val Phe Glu Ala Lys Ile Pro Thr
705             710             715             720

Ser Leu His Arg Lys Trp Val Gly Leu Asn Leu Gln Phe Leu Leu Val
                725             730             735

Phe Leu Cys Ile Leu Val Gln Ile Val Thr Cys Ile Ile Trp Leu Tyr
            740             745             750

Thr Ala Pro Pro Ser Ser Tyr Arg Asn His Glu Leu Glu Asp Glu Val
        755             760             765

Ile Phe Ile Thr Cys Asp Glu Gly Ser Leu Met Ala Leu Gly Phe Leu
770             775             780

Ile Gly Tyr Thr Cys Leu Leu Ala Ala Ile Cys Phe Phe Phe Ala Phe

-continued

```
                785                 790                 795                 800
Lys Ser Arg Lys Leu Pro Glu Asn Phe Asn Glu Ala Lys Phe Ile Thr
                805                 810                 815
Phe Ser Met Leu Ile Phe Phe Ile Val Trp Ile Ser Phe Ile Pro Ala
                820                 825                 830
Tyr Val Ser Thr Tyr Gly Lys Phe Val Ser Ala Val Glu Val Ile Ala
                835                 840                 845
Ile Leu Ala Ser Ser Phe Gly Leu Leu Gly Cys Ile Tyr Phe Asn Lys
    850                 855                 860
Cys Tyr Ile Ile Leu Phe Lys Pro Cys Arg Asn Thr Ile Glu Glu Val
865                 870                 875                 880
Arg Cys Ser Thr Ala Ala His Ala Phe Lys Val Ala Ala Arg Ala Thr
                885                 890                 895
Leu Arg Arg Ser Ala Ala Ser Arg Lys Arg Ser Ser Ser Leu Cys Gly
                900                 905                 910
Ser Thr Ile Ser Ser Pro Ala Ser Thr Cys Gly Pro Gly Leu Thr
                915                 920                 925
Met Glu Met Gln Arg Cys Ser Thr Gln Lys Val Ser Phe Gly Ser Gly
    930                 935                 940
Thr Val Thr Leu Ser Leu Ser Phe Glu Glu Thr Gly Arg Tyr Ala Thr
945                 950                 955                 960
Leu Ser Arg Thr Ala Arg Ser Arg Asn Ser Ala Asp Gly Arg Ser Gly
                965                 970                 975
Asp Asp Leu Pro Ser Arg His His Asp Gln Gly Pro Pro Gln Lys Cys
                980                 985                 990
Glu Pro Gln Pro Ala Asn Asp Ala Arg Tyr Lys Ala Ala Pro Thr Lys
                995                 1000                1005
Gly Thr Leu Glu Ser Pro Gly Gly Ser Lys Glu Arg Pro Thr Thr Met
        1010                1015                1020
Glu Glu Thr
1025

<210> SEQ ID NO 3
<211> LENGTH: 784
<212> TYPE: DNA
<213> ORGANISM: squalus acanthias
<220> FEATURE:
<221> NAME/KEY: CDS
<222> LOCATION: (1)...(784)

<400> SEQUENCE: 3 cta cta gtc ata tgg att gcg gcg gay gay gat tat ggc cgc cca ggg     48
Leu Leu Val Ile Trp Ile Ala Ala Asp Asp Asp Tyr Gly Arg Pro Gly
1               5                   10                  15 ata gat aag ttt cga gaa gaa gct gaa gag agg gac atc tgc ata gat    96
Ile Asp Lys Phe Arg Glu Glu Ala Glu Glu Arg Asp Ile Cys Ile Asp
            20                  25                  30 ttc aat gag atg att tct cag tac tat aca caa aaa gag ctg gag ttt   144
Phe Asn Glu Met Ile Ser Gln Tyr Tyr Thr Gln Lys Glu Leu Glu Phe
        35                  40                  45 att gca gat act att cag aat tcc tca gcc aaa gtg att gty gtc ttc   192
Ile Ala Asp Thr Ile Gln Asn Ser Ser Ala Lys Val Ile Xaa Val Phe
    50                  55                  60 tca aat ggc cct gac ttg gaa cca cta ata caa gag ata gtt cga cgg   240
Ser Asn Gly Pro Asp Leu Glu Pro Leu Ile Gln Glu Ile Val Arg Arg
65                  70                  75                  80 aac ata act gat aga ata tgg cta gca agt gaa gcg tgg gct agt tcc   288
```

```
Asn Ile Thr Asp Arg Ile Trp Leu Ala Ser Glu Ala Trp Ala Ser Ser
            85                  90                  95 tca ctg ata gcc aaa cca gaa tac ttc cat gtt gtt ggt gga acc att    336
Ser Leu Ile Ala Lys Pro Glu Tyr Phe His Val Val Gly Gly Thr Ile
            100                 105                 110 gga ttt gca cta aga gca gga cgc atc cca gga ttc cat gag ttt tta    384
Gly Phe Ala Leu Arg Ala Gly Arg Ile Pro Gly Phe His Glu Phe Leu
            115                 120                 125 aaa aag gtc cat ccc agc agg tcc tcc cac aat ggc ttt gtc aag gaa    432
Lys Lys Val His Pro Ser Arg Ser Ser His Asn Gly Phe Val Lys Glu
        130                 135                 140 ttc tgg gaa gaa aca ttt aat tgt tat ttc act gaa gaa tcc cta aca    480
Phe Trp Glu Glu Thr Phe Asn Cys Tyr Phe Thr Glu Glu Ser Leu Thr
145                 150                 155                 160 caa cta aag aat tgc aaa aca cca acc cat gga tta gca atg cac aat    528
Gln Leu Lys Asn Cys Lys Thr Pro Thr His Gly Leu Ala Met His Asn
            165                 170                 175 gac agt gcg aaa atg ggg cat tcc aca agg aca acg tta cga cct cca    576
Asp Ser Ala Lys Met Gly His Ser Thr Arg Thr Thr Leu Arg Pro Pro
            180                 185                 190 tgc act gga gaa gag aat atc acg agt gtg gag acc cct tac ctg gat    624
Cys Thr Gly Glu Glu Asn Ile Thr Ser Val Glu Thr Pro Tyr Leu Asp
            195                 200                 205 tat act cac ctc cgt att tca tat aat gtg tat gtg gca gtg tat tcg    672
Tyr Thr His Leu Arg Ile Ser Tyr Asn Val Tyr Val Ala Val Tyr Ser
            210                 215                 220 att gct cac gct ctg cag gac atc tat gcc tgc aca cct ggg aag ggg    720
Ile Ala His Ala Leu Gln Asp Ile Tyr Ala Cys Thr Pro Gly Lys Gly
225                 230                 235                 240 att ttt gcg aac gga tca tgt gcc gat atc aaa aaa gtc gaa gcc tgg    768
Ile Phe Ala Asn Gly Ser Cys Ala Asp Ile Lys Lys Val Glu Ala Trp
            245                 250                 255 aat cca tat gac tag t                                              784
Asn Pro Tyr Asp  *
            260

<210> SEQ ID NO 4
<211> LENGTH: 260
<212> TYPE: PRT
<213> ORGANISM: squalus acanthias

<400> SEQUENCE: 4

Leu Leu Val Ile Trp Ile Ala Ala Asp Asp Tyr Gly Arg Pro Gly
 1               5                  10                  15

Ile Asp Lys Phe Arg Glu Glu Ala Glu Glu Arg Asp Ile Cys Ile Asp
            20                  25                  30

Phe Asn Glu Met Ile Ser Gln Tyr Tyr Thr Gln Lys Glu Leu Glu Phe
        35                  40                  45

Ile Ala Asp Thr Ile Gln Asn Ser Ser Ala Lys Val Ile Val Val Phe
    50                  55                  60

Ser Asn Gly Pro Asp Leu Glu Pro Leu Ile Gln Glu Ile Val Arg Arg
65                  70                  75                  80

Asn Ile Thr Asp Arg Ile Trp Leu Ala Ser Glu Ala Trp Ala Ser Ser
            85                  90                  95

Ser Leu Ile Ala Lys Pro Glu Tyr Phe His Val Val Gly Gly Thr Ile
            100                 105                 110

Gly Phe Ala Leu Arg Ala Gly Arg Ile Pro Gly Phe His Glu Phe Leu
            115                 120                 125
```

-continued

```
Lys Lys Val His Pro Ser Arg Ser Ser His Asn Gly Phe Val Lys Glu
130                 135                 140

Phe Trp Glu Glu Thr Phe Asn Cys Tyr Phe Thr Glu Ser Leu Thr
145                 150                 155                 160

Gln Leu Lys Asn Cys Lys Thr Pro Thr His Gly Leu Ala Met His Asn
                165                 170                 175

Asp Ser Ala Lys Met Gly His Ser Thr Arg Thr Thr Leu Arg Pro Pro
                180                 185                 190

Cys Thr Gly Glu Glu Asn Ile Thr Ser Val Glu Thr Pro Tyr Leu Asp
                195                 200                 205

Tyr Thr His Leu Arg Ile Ser Tyr Asn Val Tyr Val Ala Val Tyr Ser
210                 215                 220

Ile Ala His Ala Leu Gln Asp Ile Tyr Ala Cys Thr Pro Gly Lys Gly
225                 230                 235                 240

Ile Phe Ala Asn Gly Ser Cys Ala Asp Ile Lys Lys Val Glu Ala Trp
                245                 250                 255

Asn Pro Tyr Asp
                260
```

<210> SEQ ID NO 5
<211> LENGTH: 598
<212> TYPE: DNA
<213> ORGANISM: squalus acanthias
<220> FEATURE:
<221> NAME/KEY: CDS
<222> LOCATION: (3)...(598)

<400> SEQUENCE: 5

```
tt ctg aca ata ttt gct gtg cta gga ata ctg atc act tcc ttt gtt        47
   Leu Thr Ile Phe Ala Val Leu Gly Ile Leu Ile Thr Ser Phe Val
   1               5                   10                  15 ttg gga gta ttc att aag ttc aga aat act cct att gtg aaa gcc act        95
Leu Gly Val Phe Ile Lys Phe Arg Asn Thr Pro Ile Val Lys Ala Thr
            20                  25                  30 aac aga gaa ctc tcc tat ctc ctc ctc ttc tcc tta atc tgc tgt ttc       143
Asn Arg Glu Leu Ser Tyr Leu Leu Leu Phe Ser Leu Ile Cys Cys Phe
        35                  40                  45 tcc agc tca ttg atc ttc att gga gaa ccc aaa gat tgg acc tgc aga       191
Ser Ser Ser Leu Ile Phe Ile Gly Glu Pro Lys Asp Trp Thr Cys Arg
    50                  55                  60 ctg cgt caa cct gca ttt gga atc agc ttt gtg ctg tgc att tct tgc       239
Leu Arg Gln Pro Ala Phe Gly Ile Ser Phe Val Leu Cys Ile Ser Cys
65                  70                  75 att ctg gtg aaa act aat cgt gtg cta ttg gtc ttt gag gcc aag atc       287
Ile Leu Val Lys Thr Asn Arg Val Leu Leu Val Phe Glu Ala Lys Ile
80                  85                  90                  95 cca act agc ctc cat cga aag tgg gtg ggc ctc aat ttg caa ttc tta       335
Pro Thr Ser Leu His Arg Lys Trp Val Gly Leu Asn Leu Gln Phe Leu
            100                 105                 110 ctg gtt ttc ctc tgt att ctt gtg caa att gtt act tgt gtc atc tgg       383
Leu Val Phe Leu Cys Ile Leu Val Gln Ile Val Thr Cys Val Ile Trp
        115                 120                 125 ctt tac aca gca ccc cct tcg agc tac aga aat cat gaa cta gaa gat       431
Leu Tyr Thr Ala Pro Pro Ser Ser Tyr Arg Asn His Glu Leu Glu Asp
    130                 135                 140 gaa atc att ttt att aca tgt gat gaa ggt tcc tta atg gca ctt ggt       479
Glu Ile Ile Phe Ile Thr Cys Asp Glu Gly Ser Leu Met Ala Leu Gly
145                 150                 155 ttt ctc att ggt tac aca tgc ctc ctt gct gcc att tgc ttc ttt ttt       527
```

-continued

```
Phe Leu Ile Gly Tyr Thr Cys Leu Leu Ala Ala Ile Cys Phe Phe Phe
160                 165                 170                 175 gcc ttt aag tct cgc aaa ctc cca gag aac ttc aat gag gcc aaa ttt     575
Ala Phe Lys Ser Arg Lys Leu Pro Glu Asn Phe Asn Glu Ala Lys Phe
                180                 185                 190 att acc ttc agc atg ctg ata tt                                      598
Ile Thr Phe Ser Met Leu Ile
            195
```

<210> SEQ ID NO 6
<211> LENGTH: 198
<212> TYPE: PRT
<213> ORGANISM: squalus acanthias

<400> SEQUENCE: 6

```
Leu Thr Ile Phe Ala Val Leu Gly Ile Leu Ile Thr Ser Phe Val Leu
1               5                   10                  15

Gly Val Phe Ile Lys Phe Arg Asn Thr Pro Ile Val Lys Ala Thr Asn
                20                  25                  30

Arg Glu Leu Ser Tyr Leu Leu Leu Phe Ser Leu Ile Cys Cys Phe Ser
            35                  40                  45

Ser Ser Leu Ile Phe Ile Gly Glu Pro Lys Asp Trp Thr Cys Arg Leu
        50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Val Gly Leu Asn Leu Gln Phe Leu Leu
            100                 105                 110

Val Phe Leu Cys Ile Leu Val Gln Ile Val Thr Cys Val Ile Trp Leu
        115                 120                 125

Tyr Thr Ala Pro Pro Ser Ser Tyr Arg Asn His Glu Leu Glu Asp Glu
130                 135                 140

Ile Ile Phe Ile Thr Cys Asp Glu Gly Ser Leu Met Ala Leu Gly Phe
145                 150                 155                 160

Leu Ile Gly Tyr Thr Cys Leu Leu Ala Ala Ile Cys Phe Phe Phe Ala
                165                 170                 175

Phe Lys Ser Arg Lys Leu Pro Glu Asn Phe Asn Glu Ala Lys Phe Ile
            180                 185                 190

Thr Phe Ser Met Leu Ile
        195
```

<210> SEQ ID NO 7
<211> LENGTH: 594
<212> TYPE: DNA
<213> ORGANISM: psuedupleuronecies americanus
<220> FEATURE:
<221> NAME/KEY: CDS
<222> LOCATION: (2)...(592)

<400> SEQUENCE: 7

```
g ttg acc ata tgt gca gtg ctg ggt gtt gcc ytg acg ggc ttc gtg atg    49
  Leu Thr Ile Cys Ala Val Leu Gly Val Ala Xaa Thr Gly Phe Val Met
  1               5                   10                  15 gcc gtc ttt gtc cga ttc cgc aac acc cca ata gtg aaa gcc acg aac     97
Ala Val Phe Val Arg Phe Arg Asn Thr Pro Ile Val Lys Ala Thr Asn
                20                  25                  30 cga gaa ctg tcc tac gtc ctc ctg ttc tct ctc atc tgt tgc ttc tcc    145
Arg Glu Leu Ser Tyr Val Leu Leu Phe Ser Leu Ile Cys Cys Phe Ser
```

-continued

```
                35                  40                  45
agc tcc ctc atc ttc ata gga gag ccg cag gat tgg atg tgc cgc tta        193
Ser Ser Leu Ile Phe Ile Gly Glu Pro Gln Asp Trp Met Cys Arg Leu
     50                  55                  60 cgc caa ccg gcc ttt ggg atc agt ttt gtt ctc tgt atc tcg tgc atc        241
Arg Gln Pro Ala Phe Gly Ile Ser Phe Val Leu Cys Ile Ser Cys Ile
65                  70                  75                  80 ctt gtg aaa aca aac cka gtc ctc ttg gtg ttt gaa gcc aag atc ccg        289
Leu Val Lys Thr Asn Xaa Val Leu Leu Val Phe Glu Ala Lys Ile Pro
                 85                  90                  95 aca agt ctc cat cgt aaa tgg tgg ggg tta aac cta cag ttc ctg ctg        337
Thr Ser Leu His Arg Lys Trp Trp Gly Leu Asn Leu Gln Phe Leu Leu
            100                 105                 110 gtg ttt ctg tgc aca ttt gtc caa gtc atg ata tgt gtg gtc tgg ctg        385
Val Phe Leu Cys Thr Phe Val Gln Val Met Ile Cys Val Val Trp Leu
        115                 120                 125 tac aac gcc cca cct tcc agt tac agg aat tat gac ata gat gag atg        433
Tyr Asn Ala Pro Pro Ser Ser Tyr Arg Asn Tyr Asp Ile Asp Glu Met
    130                 135                 140 att ttt atc aca tgt aat gaa ggc tct gta atg gct ctt ggg ttt ctt        481
Ile Phe Ile Thr Cys Asn Glu Gly Ser Val Met Ala Leu Gly Phe Leu
145                 150                 155                 160 att ggc tat aca tgc ctg ctg gcc gct ata tgt ttc ttc ttt gca ttc        529
Ile Gly Tyr Thr Cys Leu Leu Ala Ala Ile Cys Phe Phe Phe Ala Phe
                165                 170                 175 aaa tca cgg aaa ctt cca gaa aac ttc acc gag gct aag ttc atc act        577
Lys Ser Arg Lys Leu Pro Glu Asn Phe Thr Glu Ala Lys Phe Ile Thr
            180                 185                 190 ttt agt atg ctc ata tt                                                 594
Phe Ser Met Leu Ile
        195
```

<210> SEQ ID NO 8
<211> LENGTH: 197
<212> TYPE: PRT
<213> ORGANISM: psuedupleuronecies americanus
<220> FEATURE:
<221> NAME/KEY: VARIANT
<222> LOCATION: (1)...(197)
<223> OTHER INFORMATION: Xaa = Any Amino Acid

<400> SEQUENCE: 8

```
Leu Thr Ile Cys Ala Val Leu Gly Val Ala Leu Thr Gly Phe Val Met
1               5                   10                  15

Ala Val Phe Val Arg Phe Arg Asn Thr Pro Ile Val Lys Ala Thr Asn
                20                  25                  30

Arg Glu Leu Ser Tyr Val Leu Leu Phe Ser Leu Ile Cys Cys Phe Ser
            35                  40                  45

Ser Ser Leu Ile Phe Ile Gly Glu Pro Gln Asp Trp Met Cys Arg Leu
     50                  55                  60

Arg Gln Pro Ala Phe Gly Ile Ser Phe Val Leu Cys Ile Ser Cys Ile
65                  70                  75                  80

Leu Val Lys Thr Asn Xaa Val Leu Leu Val Phe Glu Ala Lys Ile Pro
                 85                  90                  95

Thr Ser Leu His Arg Lys Trp Trp Gly Leu Asn Leu Gln Phe Leu Leu
            100                 105                 110

Val Phe Leu Cys Thr Phe Val Gln Val Met Ile Cys Val Val Trp Leu
        115                 120                 125

Tyr Asn Ala Pro Pro Ser Ser Tyr Arg Asn Tyr Asp Ile Asp Glu Met
```

-continued

```
                130                 135                 140
Ile Phe Ile Thr Cys Asn Glu Gly Ser Val Met Ala Leu Gly Phe Leu
145                 150                 155                 160

Ile Gly Tyr Thr Cys Leu Leu Ala Ala Ile Cys Phe Phe Ala Phe
                165                 170                 175

Lys Ser Arg Lys Leu Pro Glu Asn Phe Thr Glu Ala Lys Phe Ile Thr
                180                 185                 190

Phe Ser Met Leu Ile
        195

<210> SEQ ID NO 9
<211> LENGTH: 475
<212> TYPE: DNA
<213> ORGANISM: paralichthus dentalus
<220> FEATURE:
<221> NAME/KEY: CDS
<222> LOCATION: (3)...(473)

<400> SEQUENCE: 9 tg tcg tgg acg gag ccc ttt ggg atc gcg ttg gcc ata tgt gca gcg        47
   Ser Trp Thr Glu Pro Phe Gly Ile Ala Leu Ala Ile Cys Ala Ala
     1               5                  10                  15 ctg ggt gtt gcc ttg acg ggc ttc gtg atg gcc gtc ttt atc aga ttc       95
Leu Gly Val Ala Leu Thr Gly Phe Val Met Ala Val Phe Ile Arg Phe
             20                  25                  30 cgc aac acc cca ata gtg aag gcc acg aac cga gaa ctg tcc tat gtc      143
Arg Asn Thr Pro Ile Val Lys Ala Thr Asn Arg Glu Leu Ser Tyr Val
         35                  40                  45 ctc ctg ttc tct ctc atc tgt tgc ttc tcc agt tcc ctc atc ttt att      191
Leu Leu Phe Ser Leu Ile Cys Cys Phe Ser Ser Ser Leu Ile Phe Ile
     50                  55                  60 gga gag ccg cag gat tgg atg tgt cgt tta cgc caa cct gcc ttt ggg      239
Gly Glu Pro Gln Asp Trp Met Cys Arg Leu Arg Gln Pro Ala Phe Gly
 65                  70                  75 atc agt ttt gtt ctc tgt atc tcc tgc atc ctt gtg aaa act aat aga      287
Ile Ser Phe Val Leu Cys Ile Ser Cys Ile Leu Val Lys Thr Asn Arg
 80                  85                  90                  95 gta ctc tta gta ttt gaa gcc aag atc ccc aca agt ctc cat cgt aaa      335
Val Leu Leu Val Phe Glu Ala Lys Ile Pro Thr Ser Leu His Arg Lys
             100                 105                 110 tgg tgg ggg tta aac ctt cag ttt ttg ctg gtg ttt ctg tgc aca ttt      383
Trp Trp Gly Leu Asn Leu Gln Phe Leu Leu Val Phe Leu Cys Thr Phe
         115                 120                 125 gtc caa gtc atg atc tgt gtt gtc tgg ctg tac aat gcc cct ccc tcc      431
Val Gln Val Met Ile Cys Val Val Trp Leu Tyr Asn Ala Pro Pro Ser
     130                 135                 140 agt tac agg aat tat gac ata gat gag atg att ttt atc aca              473
Ser Tyr Arg Asn Tyr Asp Ile Asp Glu Met Ile Phe Ile Thr
 145                 150                 155 tg                                                                    475

<210> SEQ ID NO 10
<211> LENGTH: 157
<212> TYPE: PRT
<213> ORGANISM: paralichthus dentalus

<400> SEQUENCE: 10

Ser Trp Thr Glu Pro Phe Gly Ile Ala Leu Ala Ile Cys Ala Ala Leu
  1               5                  10                  15

Gly Val Ala Leu Thr Gly Phe Val Met Ala Val Phe Ile Arg Phe Arg
```

```
                    20                  25                  30
Asn Thr Pro Ile Val Lys Ala Thr Asn Arg Glu Leu Ser Tyr Val Leu
            35                  40                  45

Leu Phe Ser Leu Ile Cys Cys Phe Ser Ser Leu Ile Phe Ile Gly
    50                  55                  60

Glu Pro Gln Asp Trp Met Cys Arg Leu Arg Gln Pro Ala Phe Gly Ile
65                  70                  75                  80

Ser Phe Val Leu Cys Ile Ser Cys Ile Leu Val Lys Thr Asn Arg Val
                85                  90                  95

Leu Leu Val Phe Glu Ala Lys Ile Pro Thr Ser Leu His Arg Lys Trp
            100                 105                 110

Trp Gly Leu Asn Leu Gln Phe Leu Val Phe Leu Cys Thr Phe Val
        115                 120                 125

Gln Val Met Ile Cys Val Val Trp Leu Tyr Asn Ala Pro Pro Ser Ser
130                 135                 140

Tyr Arg Asn Tyr Asp Ile Asp Glu Met Ile Phe Ile Thr
145                 150                 155

<210> SEQ ID NO 11
<211> LENGTH: 1308
<212> TYPE: DNA
<213> ORGANISM: cyclopterus lumpus
<220> FEATURE:
<221> NAME/KEY: CDS
<222> LOCATION: (2)...(1306)

<400> SEQUENCE: 11 a cgc cca ggg att gaa aaa ttt gag aag gag atg gag gag cga gac atc     49
  Arg Pro Gly Ile Glu Lys Phe Glu Lys Glu Met Glu Glu Arg Asp Ile
  1               5                   10                  15 tgc att cac ctt aat gaa ctt atc tct cag tat ttt gag gay cat gaa       97
Cys Ile His Leu Asn Glu Leu Ile Ser Gln Tyr Phe Glu Asp His Glu
            20                  25                  30 atc caa gcg ctg gct gac agg att gag aac tcc aca gct aaa gtc atc      145
Ile Gln Ala Leu Ala Asp Arg Ile Glu Asn Ser Thr Ala Lys Val Ile
        35                  40                  45 gta gtg ttt gcc agc ggc cca gat atc gag cct tta atc aaa gag atg      193
Val Val Phe Ala Ser Gly Pro Asp Ile Glu Pro Leu Ile Lys Glu Met
    50                  55                  60 gtg agg aga aac atc aca gac cgt atc tgg tta gcc agt gaa gcg tgg      241
Val Arg Arg Asn Ile Thr Asp Arg Ile Trp Leu Ala Ser Glu Ala Trp
65                  70                  75                  80 gct agc tcc tct ctt ata gct aaa cca gag tat ctt gat gtt gtg gct      289
Ala Ser Ser Ser Leu Ile Ala Lys Pro Glu Tyr Leu Asp Val Val Ala
                85                  90                  95 ggg act atc ggc ttt gct ctc aag gca ggg cat att cct ggc tta aga      337
Gly Thr Ile Gly Phe Ala Leu Lys Ala Gly His Ile Pro Gly Leu Arg
            100                 105                 110 gag ttc cta cag caa gtg caa cca aag aga gac agt cat aat gaa ttt      385
Glu Phe Leu Gln Gln Val Gln Pro Lys Arg Asp Ser His Asn Glu Phe
        115                 120                 125 gtc agg gag ttt tgg gaa gaa acc ttc aac tgt tat ctg gaa gac agc      433
Val Arg Glu Phe Trp Glu Glu Thr Phe Asn Cys Tyr Leu Glu Asp Ser
    130                 135                 140 cag aga cag cag gaa agt gag aat ggc agc aca agt ttc agg cct ttg      481
Gln Arg Gln Gln Glu Ser Glu Asn Gly Ser Thr Ser Phe Arg Pro Leu
145                 150                 155                 160 tgt act ggt gag gaa gac atc aca agt gtt gag acc ccg tac ttg gac      529
Cys Thr Gly Glu Glu Asp Ile Thr Ser Val Glu Thr Pro Tyr Leu Asp
```

-continued

```
                        165                 170                 175
tac aca cac ttt cgt atc tcc tat aac gtg tat gtt gca gtt tat tcc      577
Tyr Thr His Phe Arg Ile Ser Tyr Asn Val Tyr Val Ala Val Tyr Ser
                    180                 185                 190 att gca cag gcc ctg cag gac ata ctc acc tgc aca cct gga cat gga      625
Ile Ala Gln Ala Leu Gln Asp Ile Leu Thr Cys Thr Pro Gly His Gly
                195                 200                 205 ctc ttt gcc aac aat tcc tgt gcc gat ata aag aaa atg gaa gca tgg      673
Leu Phe Ala Asn Asn Ser Cys Ala Asp Ile Lys Lys Met Glu Ala Trp
            210                 215                 220 cag gcc ctg aag cag ctt aga cat ttg aac tac acc aac agc atg ggg      721
Gln Ala Leu Lys Gln Leu Arg His Leu Asn Tyr Thr Asn Ser Met Gly
225                 230                 235                 240 gaa aag atg cac ttt gat gag aac tca gac atg gca tca aac tac acc      769
Glu Lys Met His Phe Asp Glu Asn Ser Asp Met Ala Ser Asn Tyr Thr
                245                 250                 255 att ata aac tgg cac cgg tct gct gag gat ggc tct gtg gtg ttt gag      817
Ile Ile Asn Trp His Arg Ser Ala Glu Asp Gly Ser Val Val Phe Glu
            260                 265                 270 gac gtg gga tac tac agc atg cac gtc aag aga gga gcc aaa ctg ttc      865
Asp Val Gly Tyr Tyr Ser Met His Val Lys Arg Gly Ala Lys Leu Phe
        275                 280                 285 att gac aag aca aag att ttg tgg aat gga tac agt tcg gag gcg cca      913
Ile Asp Lys Thr Lys Ile Leu Trp Asn Gly Tyr Ser Ser Glu Ala Pro
    290                 295                 300 ttc tct aat tgc agt gag gac tgt gaa cct ggt aca agg aag ggg atc      961
Phe Ser Asn Cys Ser Glu Asp Cys Glu Pro Gly Thr Arg Lys Gly Ile
305                 310                 315                 320 att gac agt atg ccc aca tgt tgc ttt gaa tgc act gag tgt tca gat     1009
Ile Asp Ser Met Pro Thr Cys Cys Phe Glu Cys Thr Glu Cys Ser Asp
                325                 330                 335 gga gag tac agt aat cat aaa gat gcc agt gtt tgc acc aag tgt cca     1057
Gly Glu Tyr Ser Asn His Lys Asp Ala Ser Val Cys Thr Lys Cys Pro
            340                 345                 350 tat aac tct tgg tcc aat ggg aat cac aca ttc tgc ttc ctg aag gaa     1105
Tyr Asn Ser Trp Ser Asn Gly Asn His Thr Phe Cys Phe Leu Lys Glu
        355                 360                 365 atc gag ttt ctc tcc tgg aca gaa cca ttc ggg ata gct ttg gcc ata     1153
Ile Glu Phe Leu Ser Trp Thr Glu Pro Phe Gly Ile Ala Leu Ala Ile
    370                 375                 380 tgt gca gta ctg ggt gtg ctc ttg aca gct ttt gtg atc gga gtc ttt     1201
Cys Ala Val Leu Gly Val Leu Leu Thr Ala Phe Val Ile Gly Val Phe
385                 390                 395                 400 gtc aga ttc cgc aac acc cca ata gtg aag gcc aca aac cga gaa ctg     1249
Val Arg Phe Arg Asn Thr Pro Ile Val Lys Ala Thr Asn Arg Glu Leu
                405                 410                 415 tcc tac gtt ctc ctg twc tca ctt atc tgt tgc ttc tca agc tcc ctc     1297
Ser Tyr Val Leu Leu Xaa Ser Leu Ile Cys Cys Phe Ser Ser Ser Leu
            420                 425                 430 akc ttc atc gg                                                       1308
Xaa Phe Ile
        435

<210> SEQ ID NO 12
<211> LENGTH: 435
<212> TYPE: PRT
<213> ORGANISM: cyclopterus lumpus
<220> FEATURE:
<221> NAME/KEY: VARIANT
<222> LOCATION: (1)...(435)
<223> OTHER INFORMATION: Xaa = Any Amino Acid
```

```
<400> SEQUENCE: 12

Arg Pro Gly Ile Glu Lys Phe Glu Lys Glu Met Glu Glu Arg Asp Ile
 1               5                  10                  15

Cys Ile His Leu Asn Glu Leu Ile Ser Gln Tyr Phe Glu Asp His Glu
             20                  25                  30

Ile Gln Ala Leu Ala Asp Arg Ile Glu Asn Ser Thr Ala Lys Val Ile
         35                  40                  45

Val Val Phe Ala Ser Gly Pro Asp Ile Glu Pro Leu Ile Lys Glu Met
 50                  55                  60

Val Arg Arg Asn Ile Thr Asp Arg Ile Trp Leu Ala Ser Glu Ala Trp
 65                  70                  75                  80

Ala Ser Ser Leu Ile Ala Lys Pro Glu Tyr Leu Asp Val Val Ala
             85                  90                  95

Gly Thr Ile Gly Phe Ala Leu Lys Ala Gly His Ile Pro Gly Leu Arg
             100                 105                 110

Glu Phe Leu Gln Gln Val Gln Pro Lys Arg Asp Ser His Asn Glu Phe
             115                 120                 125

Val Arg Glu Phe Trp Glu Glu Thr Phe Asn Cys Tyr Leu Glu Asp Ser
 130                 135                 140

Gln Arg Gln Gln Glu Ser Glu Asn Gly Ser Thr Ser Phe Arg Pro Leu
 145                 150                 155                 160

Cys Thr Gly Glu Glu Asp Ile Thr Ser Val Glu Thr Pro Tyr Leu Asp
             165                 170                 175

Tyr Thr His Phe Arg Ile Ser Tyr Asn Val Tyr Val Ala Val Tyr Ser
             180                 185                 190

Ile Ala Gln Ala Leu Gln Asp Ile Leu Thr Cys Thr Pro Gly His Gly
         195                 200                 205

Leu Phe Ala Asn Asn Ser Cys Ala Asp Ile Lys Lys Met Glu Ala Trp
 210                 215                 220

Gln Ala Leu Lys Gln Leu Arg His Leu Asn Tyr Thr Asn Ser Met Gly
 225                 230                 235                 240

Glu Lys Met His Phe Asp Glu Asn Ser Asp Met Ala Ser Asn Tyr Thr
             245                 250                 255

Ile Ile Asn Trp His Arg Ser Ala Glu Asp Gly Ser Val Val Phe Glu
             260                 265                 270

Asp Val Gly Tyr Tyr Ser Met His Val Lys Arg Gly Ala Lys Leu Phe
 275                 280                 285

Ile Asp Lys Thr Lys Ile Leu Trp Asn Gly Tyr Ser Ser Glu Ala Pro
 290                 295                 300

Phe Ser Asn Cys Ser Glu Asp Cys Glu Pro Gly Thr Arg Lys Gly Ile
 305                 310                 315                 320

Ile Asp Ser Met Pro Thr Cys Cys Phe Glu Cys Thr Glu Cys Ser Asp
             325                 330                 335

Gly Glu Tyr Ser Asn His Lys Asp Ala Ser Val Cys Thr Lys Cys Pro
             340                 345                 350

Tyr Asn Ser Trp Ser Asn Gly Asn His Thr Phe Cys Phe Leu Lys Glu
             355                 360                 365

Ile Glu Phe Leu Ser Trp Thr Glu Pro Phe Gly Ile Ala Leu Ala Ile
         370                 375                 380

Cys Ala Val Leu Gly Val Leu Thr Ala Phe Val Ile Gly Val Phe
 385                 390                 395                 400

Val Arg Phe Arg Asn Thr Pro Ile Val Lys Ala Thr Asn Arg Glu Leu
```

```
                  405                 410                 415
Ser Tyr Val Leu Leu Xaa Ser Leu Ile Cys Cys Phe Ser Ser Leu
            420                 425                 430

Xaa Phe Ile
        435

<210> SEQ ID NO 13
<211> LENGTH: 23
<212> TYPE: PRT
<213> ORGANISM: Artificial Sequence
<220> FEATURE:
<223> OTHER INFORMATION: primer

<400> SEQUENCE: 13

Asp Asp Asp Tyr Gly Arg Pro Gly Ile Glu Lys Phe Arg Glu Glu Ala
 1               5                  10                  15

Glu Glu Arg Asp Ile Cys Ile
            20

<210> SEQ ID NO 14
<211> LENGTH: 17
<212> TYPE: PRT
<213> ORGANISM: Artificial Sequence
<220> FEATURE:
<223> OTHER INFORMATION: primer

<400> SEQUENCE: 14

Ala Arg Ser Arg Asn Ser Ala Asp Gly Arg Ser Gly Asp Asp Leu Pro
 1               5                  10                  15

Cys

<210> SEQ ID NO 15
<211> LENGTH: 20
<212> TYPE: DNA
<213> ORGANISM: a primer
<220> FEATURE:
<221> NAME/KEY: unsure
<222> LOCATION: (3)...(3)
<223> OTHER INFORMATION: N = deoxyinosine
<220> FEATURE:
<221> NAME/KEY: unsure
<222> LOCATION: (9)...(9)
<223> OTHER INFORMATION: Y = C+T
<220> FEATURE:
<221> NAME/KEY: unsure
<222> LOCATION: (12)...(12)
<223> OTHER INFORMATION: Y = C+T
<220> FEATURE:
<221> NAME/KEY: unsure
<222> LOCATION: (15)...(15)
<223> OTHER INFORMATION: Y = C+T
<220> FEATURE:
<221> NAME/KEY: unsure
<222> LOCATION: (18)...(18)
<223> OTHER INFORMATION: Y = C+T

<400> SEQUENCE: 15
gcngctgayg aygaytaygg                                          20

<210> SEQ ID NO 16
<211> LENGTH: 24
<212> TYPE: DNA
<213> ORGANISM: a primer
<220> FEATURE:
<221> NAME/KEY: unsure
<222> LOCATION: (4)...(4)
<223> OTHER INFORMATION: N=deoxyinosine
<220> FEATURE:
```

```
<221> NAME/KEY: unsure
<222> LOCATION: (7)...(7)
<223> OTHER INFORMATION: Y=C+T
<220> FEATURE:
<221> NAME/KEY: unsure
<222> LOCATION: (10)...(10)
<223> OTHER INFORMATION: N=deoxyinosine
<220> FEATURE:
<221> NAME/KEY: unsure
<222> LOCATION: (13)...(13)
<223> OTHER INFORMATION: Y=C+T
<220> FEATURE:
<221> NAME/KEY: unsure
<222> LOCATION: (16)...(16)
<223> OTHER INFORMATION: Y=C+T
<220> FEATURE:
<221> NAME/KEY: unsure
<222> LOCATION: (22)...(22)
<223> OTHER INFORMATION: R=A+G

<400> SEQUENCE: 16
ccangcytcn agyttyttda trtc                                         24

<210> SEQ ID NO 17
<211> LENGTH: 28
<212> TYPE: DNA
<213> ORGANISM: a primer
<220> FEATURE:
<221> NAME/KEY: unsure
<222> LOCATION: (5)...(5)
<223> OTHER INFORMATION: K=T+G
<220> FEATURE:
<221> NAME/KEY: unsure
<222> LOCATION: (20)...(20)
<223> OTHER INFORMATION: Y=C+T
<220> FEATURE:
<221> NAME/KEY: unsure
<222> LOCATION: (23)...(23)
<223> OTHER INFORMATION: R=A+G

<400> SEQUENCE: 17
tgtcktggac ggagccctty ggratcgc                                     28

<210> SEQ ID NO 18
<211> LENGTH: 34
<212> TYPE: DNA
<213> ORGANISM: a primer
<220> FEATURE:
<221> NAME/KEY: unsure
<222> LOCATION: (7)...(7)
<223> OTHER INFORMATION: K=T+G
<220> FEATURE:
<221> NAME/KEY: unsure
<222> LOCATION: (10)...(10)
<223> OTHER INFORMATION: R=A+G
<220> FEATURE:
<221> NAME/KEY: unsure
<222> LOCATION: (16)...(16)
<223> OTHER INFORMATION: R=A+G
<220> FEATURE:
<221> NAME/KEY: unsure
<222> LOCATION: (19)...(19)
<223> OTHER INFORMATION: K=T+G
<220> FEATURE:
<221> NAME/KEY: unsure
<222> LOCATION: (25)...(25)
<223> OTHER INFORMATION: R=A+G
<220> FEATURE:
<221> NAME/KEY: unsure
<222> LOCATION: (28)...(28)
<223> OTHER INFORMATION: R=A+G

<400> SEQUENCE: 18
ataggckggr atgaargaka tccaracrat gaag                              34
```

```
<210> SEQ ID NO 19
<211> LENGTH: 31
<212> TYPE: DNA
<213> ORGANISM: a primer
<220> FEATURE:
<221> NAME/KEY: unsure
<222> LOCATION: (4)...(4)
<223> OTHER INFORMATION: K=T+G
<220> FEATURE:
<221> NAME/KEY: unsure
<222> LOCATION: (7)...(7)
<223> OTHER INFORMATION: R=A+G
<220> FEATURE:
<221> NAME/KEY: unsure
<222> LOCATION: (13)...(13)
<223> OTHER INFORMATION: R=A+G
<220> FEATURE:
<221> NAME/KEY: unsure
<222> LOCATION: (16)...(16)
<223> OTHER INFORMATION: K=T+G
<220> FEATURE:
<221> NAME/KEY: unsure
<222> LOCATION: (22)...(22)
<223> OTHER INFORMATION: R=A+G
<220> FEATURE:
<221> NAME/KEY: unsure
<222> LOCATION: (25)...(25)
<223> OTHER INFORMATION: R=A+G

<400> SEQUENCE: 19
ggckggratg aargakatcc aracratgaa g                              31
```

The inventiion claimed is:

1. An isolated polypeptide molecule having at least about 80% identity with
    a) SEQ ID NO: 2; or
    b) an amino acid sequence encoded by the nucleic acid sequence of SEQ ID NO: 1;
    wherein the isolated polypeptide molecule allows fish to sense $Ca^{2+}$, $Mg^{2+}$, or $Na^+$ ion concentrations.

2. An isolated polypeptide molecule having at least about 90% identity with
    a) SEQ ID NO: 2; or
    b) an amino acid sequence encoded by the nucleic acid sequence of SEQ ID NO: 1;
    wherein the isolated polypeptide molecule allows fish to sense $Ca^{2+}$, $Mg^{2+}$, or $Na^+$ ion concentrations.

3. An isolated polypeptide molecule having at least about 80% identity with
    a) SEQ ID NO: 2; or
    b) an amino acid sequence encoded by the nucleic acid sequence of SEQ ID NO: 1;
    wherein the isolated polypeptide molecule assists fish in adapting to changing $Ca^{2+}$, $Mg^{2+}$, or $Na^+$ ion concentrations by altering water intake, water absorption or urine output.

4. An isolated polypeptide molecule having at least about 90% identity with
    a) SEQ ID NO: 2; or
    b) an amino acid sequence encoded by the nucleic acid sequence of SEQ ID NO: 1;
    wherein the isolated polypeptide molecule assists fish in adapting to changing $Ca^{2+}$, $Mg^{2+}$, or $Na^+$ ion concentrations by altering water intake, water absorption or urine output.

5. An isolated polypeptide molecule having at least about 80% identity with
    a) SEQ ID NO: 2; or
    b) an amino acid sequence encoded by the nucleic acid sequence of SEQ ID NO: 1;
    wherein the isolated polypeptide molecule allows a fish to modulate the percentage of total fat, protein and moisture of muscle and allows fish to sense or adapt to $Ca^{2+}$, $Mg^{2+}$, or $Na^+$ ion concentrations.

6. An isolated polypeptide molecule having at least about 90% identity with
    a) SEQ ID NO: 2; or
    b) an amino acid sequence encoded by the nucleic acid sequence of SEQ LID NO: 1;
    wherein the isolated polypeptide molecule allows a fish to modulate the percentage of total fat, protein and moisture of muscle and allows fish to sense or adapt to $Ca^{2+}$, $Mg^{2+}$, or $Na^+$ ion concentrations.

7. An isolated polypeptide molecule having an amino acid sequence that comprises:
    a) SEQ ID NO: 2; or
    b) an amino acid sequence encoded by the nucleic acid sequence of SEQ ID NO: 1
    wherein the isolated polvpeptide molecule allows fish to sense or adapt to $Ca^{2+}$, $Mg^{2+}$, or $Na^+$ ion concentrations.

8. An isolated polypeptide encoded by a nucleic acid sequence of a clone deposited under ATCC No.: 209602, wherein the isolated polypeptide molecule allows fish to sense or adapt to $Ca^{2+}$, $Mg^{2+}$, or $Na^+$ ion concentrations.

* * * * *